US012606587B2

(12) United States Patent
Mulard et al.

(10) Patent No.: US 12,606,587 B2
(45) **Date of Patent: *Apr. 21, 2026**

(54) **PROTECTED TETRASACCHARIDES, THEIR PROCESS OF PREPARATION AND THEIR USE AS TRANSGLUCOSYLASE ACCEPTOR SUBSTRATES IN THE CHEMO-ENZYMATIC SYNTHESIS OF *SHIGELLA FLEXNERI* SPECIFIC OLIGOSACCHARIDES**

(71) Applicants: INSTITUT PASTEUR, Paris (FR); Institut national de recherche pour l'agriculture, l'alimentation et l'environnement, Paris (FR); INSTITUT NATIONAL DES SCIENCES APPLIQUEES DE TOULOUSE, Toulouse Cedex (FR); CENTRE NATIONAL DE LA RECHERCHE SCIENTIFIQUE, Paris (FR)

(72) Inventors: Laurence Mulard, Le Kremlin Bicetre (FR); Guillaume Le Heiget, Paris (FR); Zhaohu Hu, Wuhan (CN); Louis-Antoine Barel, Royat (FR); Isabelle Andre, Toulouse (FR); Claire Moulis, Vieillevigne (FR); Magali Remaud-Simeon, Ramonville (FR); Sophie Barbe, Goyrans (FR); Mounir Benkoulouche, Villenave d'Ornon (FR); Akli Ben Imeddourene, Toulouse (FR)

(73) Assignees: INSTITUT PASTEUR, Paris (FR); Institut national de recherche pour l'agriculture, l'alimentation et l'environnement, Paris (FR); INSTITUT NATIONAL DES SCIENCES APPLIQUEES DE TOULOUSE, Toulouse Cedex (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/463,658

(22) Filed: Sep. 8, 2023

(65) Prior Publication Data

US 2024/0002423 A1 Jan. 4, 2024

Related U.S. Application Data

(62) Division of application No. 16/627,729, filed as application No. PCT/EP2018/068013 on Jul. 3, 2018, now Pat. No. 11,834,468.

(Continued)

(51) Int. Cl.
*C07H 15/18* (2006.01)
*C07H 13/04* (2006.01)

(Continued)

(52) U.S. Cl.
CPC ............ *C07H 15/18* (2013.01); *C07H 13/04* (2013.01); *C07H 15/10* (2013.01); *C07H 15/203* (2013.01);

(Continued)

(58) Field of Classification Search
None
See application file for complete search history.

(56) References Cited

U.S. PATENT DOCUMENTS

| | | | | |
|---|---|---|---|---|
| 8,815,239 B2 * | 8/2014 | Mulard | .................. | A61P 37/04 536/123.13 |
| 11,834,468 B2 * | 12/2023 | Mulard | .................. | C07H 13/04 |
| 2015/0050282 A1 | 2/2015 | Mulard et al. | | |

FOREIGN PATENT DOCUMENTS

| | | | | |
|---|---|---|---|---|
| EP | 2386563 A1 * | 11/2011 | ....... | G01N 33/56916 |
| WO | 2008155487 A2 | 12/2008 | | |

OTHER PUBLICATIONS

Artner et al., "Conformationally Constrained Lipid A Mimetics for Exploration of Structural Basis of TLR4/MD-2 Activation by Lipopolysaccharide" ACS Chemical Biology vol. 8 pp. 2423-2432, DOI: 10.1021/cb4003199 (Year: 2013).*

(Continued)

*Primary Examiner* — Andrea Olson
(74) *Attorney, Agent, or Firm* — Arrigo, Lee, Guttman & Mouta-Bellum LLP

(57) ABSTRACT

The present invention provides protected tetrasaccharides, their process of preparation and their use in the synthesis of (Continued)

Figure 1A:
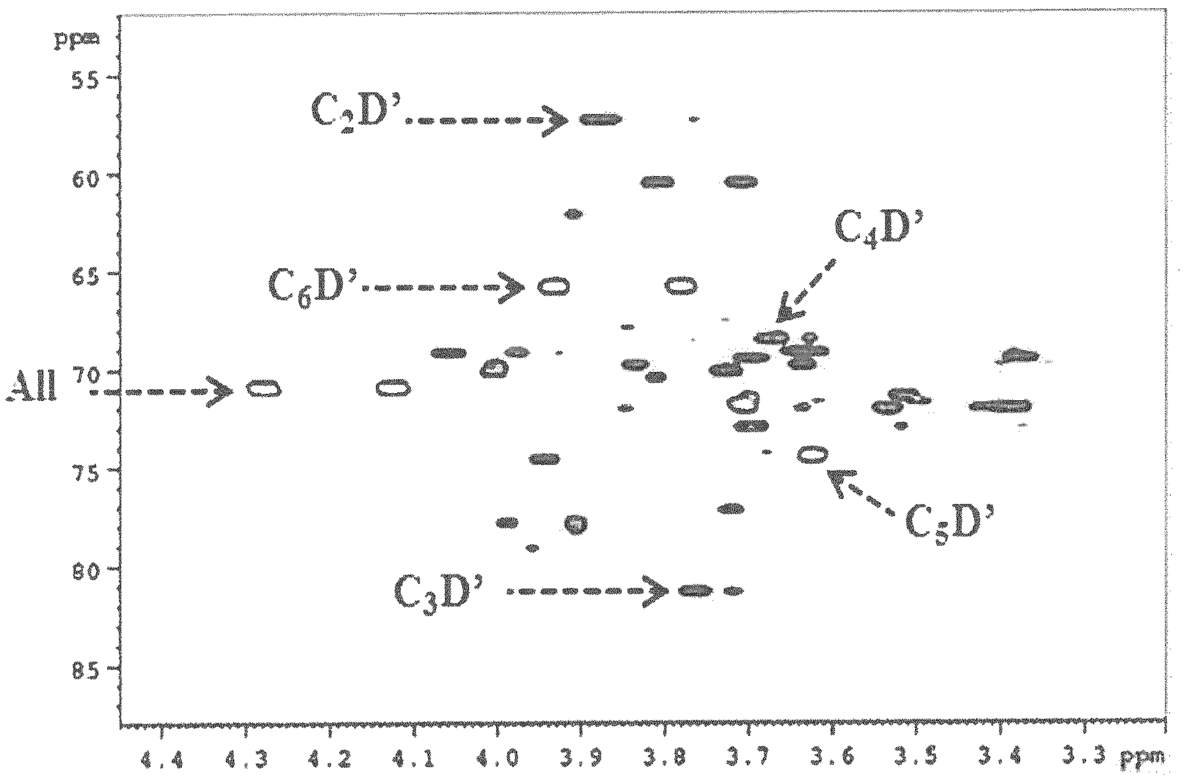

oligosaccharides, in particular fragments of O-antigens from *Shigella flexneri*, for example of serotype 1a, 1b, 2a, 2b, 3a, X, 4a, 4b, 5a, 5b, 7a or 7b.

1 Claim, 2 Drawing Sheets

Related U.S. Application Data

(60) Provisional application No. 62/528,277, filed on Jul. 3, 2017.

(51) Int. Cl.

| | |
|---|---|
| ***C07H 15/10*** | (2006.01) |
| ***C07H 15/203*** | (2006.01) |
| ***C12P 19/04*** | (2006.01) |
| ***C12P 19/14*** | (2006.01) |
| ***C12P 19/18*** | (2006.01) |
| ***C12P 19/28*** | (2006.01) |

(52) U.S. Cl.
CPC ............... *C12P 19/04* (2013.01); *C12P 19/14* (2013.01); *C12P 19/18* (2013.01); *C12P 19/28* (2013.01)

(56) References Cited

OTHER PUBLICATIONS

Shimoyama et al., "Chemical Synthesis of Helicobacter pylori Lipopolysaccharide Partial Structures and their Selective Proinflammatory Responses" Chemistry a European Journal vol. 17 pp. 14464-14474, DOI: 10.1002/chem.201003581 (Year: 2011).*

Enugala et al., "Stereoselective Glycosylation of Glucosamine: The Role of the N-Protecting Group" Chemistry an Asian Journal vol. 7 pp. 2482-2501, DOI: 10.1002/asia.201200338 (Year: 2012).*

Salamone, et al., "Investigation on the Synthesis of Shigella flexneri Specific Oligosaccharides Using Disaccharides as Potential Transglucosylase Acceptor Substrates," Journal of Biological Chemistry, 2015, 80(22), 11237-11257.

Boutet, et al., "Detailed Investigation of the Immunodominant Role of O-Antigen Stoichiometric O-Acetylation as Revealed by Chemical Synthesis, Immunochemistry, Solution Conformation and STD-NMR Spectroscopy for Shigella flexneri 3a," Chemistry—a European Journal, 2016, 22(31), 10892-10911.

Josephson et al., "Artificial carbohydrate antigens: the synthesis of the tetrasaccharide repeating unit of Shigella flexneri O antigen," Canadian Journal of Chemistry, 1979, 57, 3073-3079.

Bundle et al., "Artificial Carbohydrate Antigens: the Synthesis of a Tetrasaccharide Hapten, A Shigella u flexneri O-Antigen Repeating Un It" Carbohydrate Research, 1980, 80, 75-85.

Boutet et al., "Synthesis of Two Tetra- and Four Pentasaccharide Fragments of Shigella flexneri Serotypes 3a and X O-Antigens from a Common Tetrasaccharide Intermediate," Eur J Org Chem, 2008, 5526-5542.

Gauthier et al., "Non-stoichiometric O-acetylation of Shigella flexneri 2a O-specific polysaccharide: synthesis and antigenicity," Organic and Biomolecular Chemistry, 2014, 12, 4218-4232.

Hu et al., "Efficient Iterative Synthesis of O-Acetylated Tri- to Pentadecasaccharides Related to the Lipopolysaccharide of Shigella X flexneri Type 3a through Di- and Trisaccharide Glycosyl Donors," Chemistry: an Asian Journal, 2017, 12, 419-439.

Agoston et al., "A new set of orthogonal protecting groups on a monosaccharide scaffold," Tetrahedron Letters, 2015, 56, 5010-5012.

Wong et al., "Assembly of Oligosaccharide Libraries with a Designed Building Block and an Efficient Orthogonal Protection-Deprotection Strategy," J Am Chem Soc, 1998, 120, 7137-7138.

Valdor et al., "A new set of orthogonal protecting groups on a monosaccharide scaffold" Progress in Biotechnology, 1996, 14, 645-650.

* cited by examiner

PROTECTED TETRASACCHARIDES, THEIR PROCESS OF PREPARATION AND THEIR USE AS TRANSGLUCOSYLASE ACCEPTOR SUBSTRATES IN THE CHEMO-ENZYMATIC SYNTHESIS OF *SHIGELLA FLEXNERI* SPECIFIC OLIGOSACCHARIDES

CROSS REFERENCE TO RELATED APPLICATIONS

This application is a divisional of U.S. application Ser. No. 16/627,729, filed Dec. 30, 2019, which is the U.S. Natl. Stage of International Appln. PCT/EP2018/068013, filed Jul. 3, 2018, which claims the benefit of U.S. Provisional Appln. 62/528,277 filed Jul. 3, 2017, all of which are herein incorporated by reference in their entirety.

FIELD OF THE INVENTION

The present invention provides protected tetrasaccharides, their process of preparation and their use in the synthesis of oligosaccharides, in particular fragments of O-antigens from *Shigella flexneri*, for example of serotype 1a, 1b, 2a, 2b, 3a, X, 4a, 4b, 5a, 5b, 7a or 7b.

Carbohydrates displayed at the surface of cells and pathogens are of great therapeutic potential. On the one hand, the human glycome is being scrutinized in detail, on the other hand increasing knowledge on microbial carbohydrates and carbohydrate binding proteins offers new openings for therapeutic and prophylactic interventions. Among a large diversity of applications, carbohydrates are actively investigated as vaccine components. In this context, synthetic carbohydrates represent an attractive alternative to carbohydrate antigens of biological origin. The licensing of QuimiHib®, over a decade ago, demonstrated feasibility. Other vaccine candidates derived from synthetic oligosaccharides are under development whether targeting infectious diseases or non-transmittable diseases such as cancer.

Owing to an increasing interest in well-defined carbohydrates, progress in synthetic methodologies to complex oligosaccharides evolve rapidly. Reports on the use of scaffolds compatible with customized modifications opening the way to a diversity of targets have emerged, especially related to the synthesis of highly diverse complex N-glycans. Chemo-enzymatic strategies, mostly relying on the use of glycosyltransferases at the latest stages of the synthesis, are highly attractive. These two approaches were successfully combined to deliver a small library of N-glycans (*Science* (2013) 341 (6144), 379-83). Similarly, glycorandomization/glycodiversification find wide applications. Yet, drawbacks in the use of glycosyltransferases include enzyme availability, added to cost and availability of the sugar-nucleotide donors.

An alternative strategy consists in the use of “engineered transglycosidase/low cost donor” systems adapted to the customization of non-natural acceptors for the chemo-enzymatic synthesis of carbohydrates and glycoconjugates (*Cell. Mol. Life Sci.* (2016) 73, 2661-79). This strategy involves mono- and disaccharide acceptors, demonstrating feasibility for simple non-natural acceptors (*J. Am. Chem. Soc.* (2009) 131, 7379-89, *Chem. Commun.* (2015) 51, 2581-4). However, this method provides an access to a limited number of targets only, due to its partially divergent character.

Accordingly, it is an object of the present invention to provide versatile core precursors, able to yield a great number of oligosaccharides in a highly efficient divergent manner.

Another aim of the present invention is to provide a way to a large variety of selected targets in the context of vaccine development against shigellosis. Most of the known 15 *S. flexneri* serotypes are pathogenic for human and a multivalent vaccine providing broad serotype coverage is required (*Clin. Infect. Dis.* (2014) 59, 933). Additional *S. flexneri* O-antigen diversity has been described (*Biochemistry* (*Moscow*) (2015) 80, 901-14).

Inventors have for the first time demonstrated that enzymes are being able to perform the in vitro α-D-glucosylation of the ABCD and DABC tetrasaccharides, corresponding to the backbone repeating unit, and frame-shift thereof, respectively, of *S. flexneri* O-antigens (*Biochemistry* (*Moscow*) (2015) 80, 901-14). Surprisingly, branching sucrases, and more generally glucansucrases, can in particular glucosylate the non-natural $AB_{ClAc}C_{Cl3Ac}D$-All tetrasaccharide acceptor, to access *S. flexneri* specifically α-D-glucosylated pentasaccharides.

Most of the known *S. flexneri* O-antigens are defined by a repeating unit encompassing a common $(ABCD)_n$ tetrasaccharide backbone. This feature offers major opportunities for the development of a broad serotype coverage vaccine against *S. flexneri* by use of synthetic carbohydrate haptens.

In contrast to other strategies whereby the design of a n-valent polysaccharide-based vaccine requires the independent preparation of n monovalent polysaccharide antigens and their conversion into immunogens (see for example Prevnar®, Synflorix®, and other licensed polysaccharide-protein conjugate vaccines), synthesis opens the way to a divergent strategy to the target carbohydrate haptens built on a single versatile core precursor inspired from the tetrasaccharide backbone repeat of the O-antigens of interest.

Thus, in one aspect, the present invention relates to a compound of following formula ($I_0$):

$$(_TD)_xAB_ZC(_TD)_y\text{-}R \qquad (I_0)$$

wherein:

x and y are 0 or 1, providing x+y=1;

A is 2)-α-L-Rhap-(1→;

B is 2)-α-L-Rhap-(1→;

C is 3)-α-L-Rhap-(1→;

D is 3)-α-D-GlcpN-(1→;

Z is ClAc, BrAc, Ac or Ø;

T is a protecting group capable of anchimeric assistance and being orthogonal to Z, when Z is ClAc, BrAc or Ac, or is azide ($N_3$);

R is a protecting group compatible with chain elongation into O-antigen fragments, and being orthogonal to T and Z, when Z is ClAc, BrAc or Ac;

ClAc is $ClCH_2$—C(O)—;

BrAc is $BrCH_2$—C(O)—.

In one aspect, the present invention relates to a compound of following formula ($I_0$):

$$(_TD)_xAB_ZC(_TD)_y\text{-}R \qquad (I_0)$$

wherein:

x and y are 0 or 1, providing x+y=1;

A is 2)-α-L-Rhap-(1→;

B is 2)-α-L-Rhap-(1→;

C is 3)-α-L-Rhap-(1→;

D is 3)-α-D-GlcpN-(1→ or 3)-β-D-GlcpN-(1→;

Z is ClAc, BrAc, Ac or Ø;

T is a protecting group capable of anchimeric assistance and being preferentially orthogonal to Z, in particular when Z is Ac, or is azide ($N_3$);

R is a protecting group compatible with chain elongation into O-antigen fragments, and being orthogonal to T and Z, when Z is ClAc, BrAc or Ac;

ClAc is $ClCH_2$—C(O)—;

BrAc is $BrCH_2$—C(O)—.

In a particular embodiment:

when x=0 and y=1, D is 3)-α-D-GlcpN-(1→ or 3)-β-D-GlcpN-(1→;

when x=1 and y=0, D is 3)-β-D-GlcpN-(1→; Regarding formulae ($I_0$) and (I), D is in particular 3)-β-D-GlcpN-(1→;

In a particular embodiment, ${}_TD$ means that T is in position $2_D$.

In a particular embodiment, zC means that Z is in position $2_C$.

Orthogonality and orthogonal protecting groups in carbohydrate chemistry are well known from the skilled in the art, and are in particular described in Agoston et al. (Tetrahedron: Asymmetry 27 (2016) 707-728).

R is in particular chosen from allyl (All), para-methoxyphenyl (PMP), pentenyl (Pent), phenyl (Ph), triisopropylsilyl (TIPS) or tert-butyldiphenylsilyl (TBDPS) group.

R is in particular on the O in position $1_C$, when x=1, or on the O in position $1_D$, when y=1.

When R is Ph, the atom in position $1_C$, when x=1, and in position $1_D$, when y=1, is in fact a S.

T is in particular chosen from trichloroacetyl (Cl3Ac), 2,2,2-trichloroethoxycarbonyl (Troc) or allyloxycarbonyl (Alloc).

In another aspect, the present invention relates to a compound of following formula (I):

$$({}_{Cl3Ac}D)_xAB_ZC({}_{Cl3Ac}D)_y\text{-All} \quad (I)$$

wherein:

x and y are 0 or 1, providing x+y=1;

A is 2)-α-L-Rhap-(1→;

B is 2)-α-L-Rhap-(1→;

C is 3)-α-L-Rhap-(1→;

D is 3)-α-D-GlcpN-(1→;

Z is ClAc, BrAc, Ac or Ø;

All is allyl;

Cl3Ac is $Cl_3C$—C(O)—;

ClAc is $ClCH_2$—C(O)—;

BrAc is $BrCH_2$—C(O)—.

In another aspect, the present invention relates to a compound of following formula (I):

$$({}_{Cl3Ac}D)_xAB_ZC({}_{Cl3Ac}D)_y\text{-All} \quad (I)$$

wherein:

x and y are 0 or 1, providing x+y=1;

A is 2)-α-L-Rhap-(1→;

B is 2)-α-L-Rhap-(1→;

C is 3)-α-L-Rhap-(1→;

D is 3)-α-D-GlcpN-(1→ or 3)-β-D-GlcpN-(1→;

Z is ClAc, BrAc, Ac or Ø;

All is allyl;

Cl3Ac is $Cl_3C$—C(O)—;

ClAc is $ClCH_2$—C(O)—;

BrAc is $BrCH_2$—C(O)—.

In a particular embodiment:

when x=0 and y=1, D is 3)-α-D-GlcpN-(1→ or 3)-β-D-GlcpN-(1→;

when x=1 and y=0, D is 3)-β-D-GlcpN-(1→;

Compounds of formula (I) offer compatibility with chain elongation into O-antigen fragments, which may require a protecting group able to ensure anchimeric assistance at position 2 of the reducing residue.

The orthogonal protecting group in position 2c enables the $2_C$-O-acetylation pattern of importance for some serotypes.

Lastly, orthogonal protection at the anomeric position of the reducing residue enables to avoid α/β mixtures while facilitating subsequent chemical modification and in particular chain elongation into O-antigen fragments.

In a particular embodiment, the present invention relates to a compound of formula (I), wherein:

Cl3Ac is in position $2_D$,

Z is in position $2_C$, and/or

All is in position $1_C$, when x=1, or in position $1_D$, when y=1.

In a particular embodiment, Z is ClAc, corresponding to a compound of formula $({}_{Cl3Ac}D)_xAB_{ClAc}C({}_{Cl3Ac}D)_y$-All.

In a particular embodiment, Z is BrAc, corresponding to a compound of formula $({}_{Cl3Ac}D)_xAB_{BrAc}C({}_{Cl3Ac}D)_y$-All.

In a particular embodiment, Z is Ac, corresponding to a compound of formula $({}_{Cl3Ac}D)_xAB_{Ac}C({}_{Cl3Ac}D)_y$-All.

In a particular embodiment, Z is Ø, corresponding to a compound of formula $({}_{Cl3Ac}D)_xABC({}_{Cl3Ac}D)_y$-All.

In a particular embodiment, the present invention relates to a compound of formula (I), wherein x is 0 and y is 1, corresponding to the following formula (Ia):

$$AB_ZC_{Cl3Ac}D\text{-All} \quad (Ia).$$

In a particular embodiment, said compound is of formula $AB_{ClAc}C_{Cl3Ac}D$-All, $AB_{BrAc}C_{Cl3Ac}D$-All, $AB_{Ac}C_{Cl3Ac}D$-All or $ABC_{Cl3Ac}D$-All.

The compound of formula (I) is in particular of the following formula:

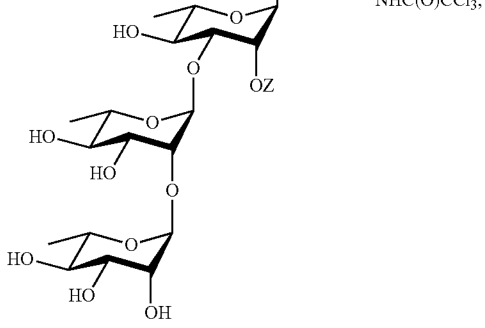

more particularly with Z=H or Z=ClAc as in the following:

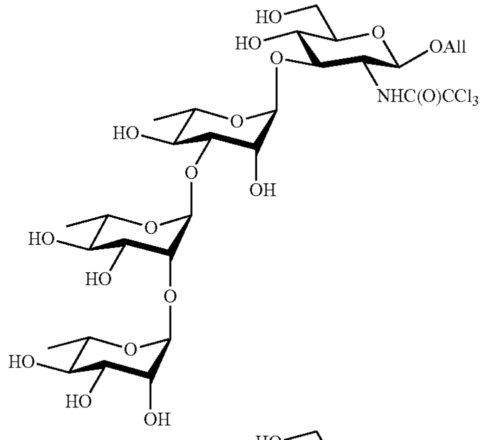

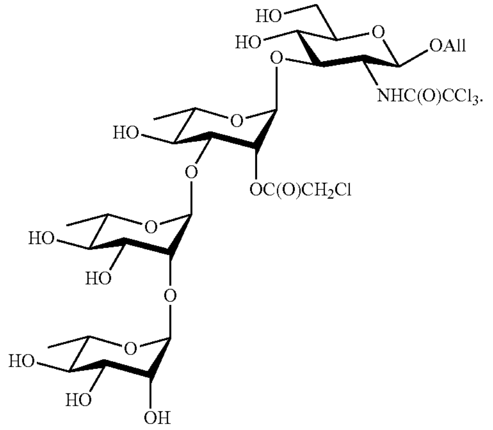

In a particular embodiment, the present invention relates to a compound of formula (I), wherein x is 1 and y is 0, corresponding to the following formula (Ib):

$_{Cl3Ac}DAB_{Z}C$-All (Ib).

In a particular embodiment, said compound is of formula $_{Cl3Ac}DAB_{ClAc}C$-All, $_{Cl3Ac}DAB_{BrAc}C$-All, $_{Cl3Ac}DAB_{Ac}C$-All or $_{Cl3Ac}DAB_{ClAc}$-All.

The compound of formula (I) is in particular of the following formula:

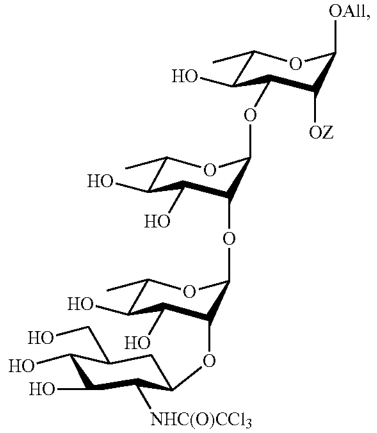

more particularly with Z=H or Z=ClAc as in the following:

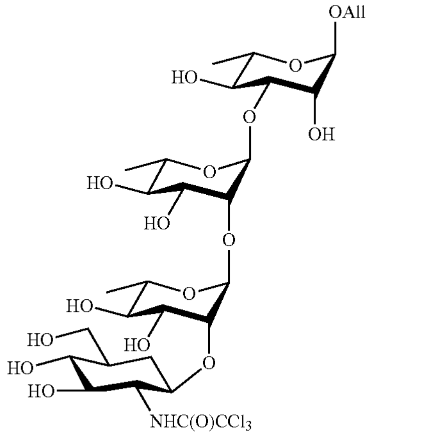

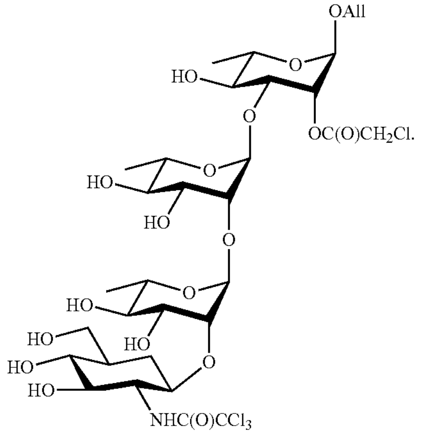

In another aspect, the present invention relates to a process of preparation of a compound of formula ($I_0$) as defined above, comprising the following steps:

(i) a step of contacting a protected $AB_ZC$-triosyl donor with a protected $_TD$-R acceptor to yield a protected $AB_ZC_TD$-R compound;

(ii) one or more steps of deprotection of the protected compound obtained in step (i) to give a compound of formula $AB_ZC_TD$-R.

In another aspect, the present invention relates to a process of preparation of a compound of formula (I) as defined above, comprising the following steps:

(i) a step of contacting a protected $AB_ZC$-triosyl donor with a protected $_{Cl3Ac}D$-All acceptor to yield a protected $AB_ZC_{Cl3Ac}D$-All compound;

(ii) one or more steps of deprotection of the protected compound obtained in step (i) to give a compound of formula $AB_ZC_{Cl3Ac}D$-All.

In a particular embodiment, the $AB_ZC$-triosyl donor is of formula $AB_ZC$—Z', wherein Z' is PTFA or TCA, PTFA representing N-phenyltrifluoroacetimidoyl and TCA representing trichloroacetimidoyl, Z' being more particularly TCA.

In a particular embodiment, the protected $AB_ZC$-triosyl donor is of one of the following formulae:

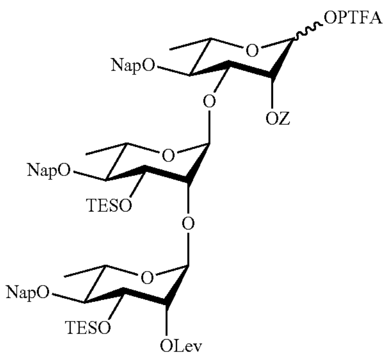
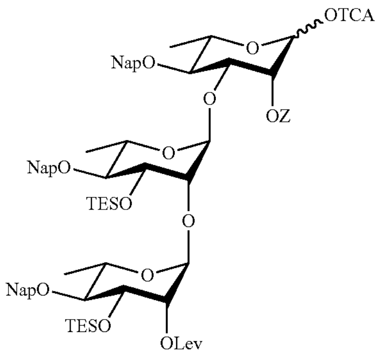
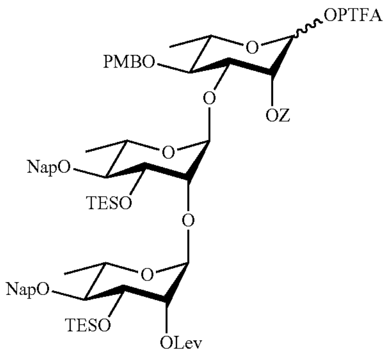
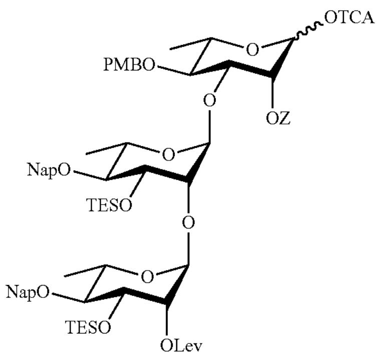
-continued
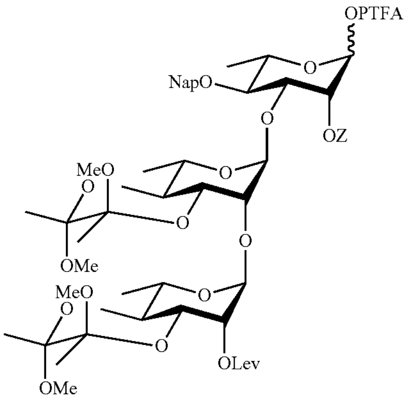
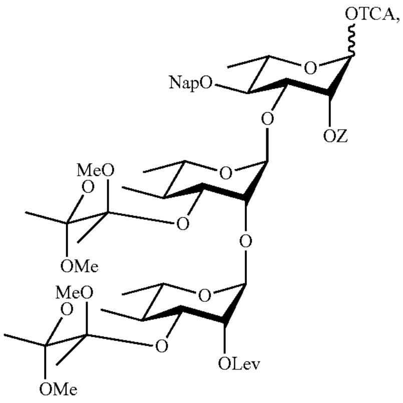
, and notably
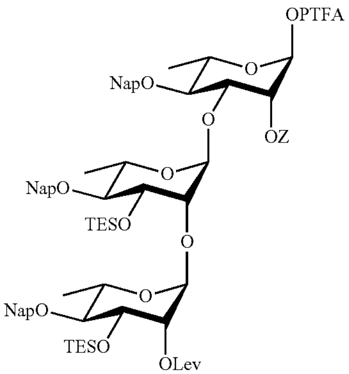
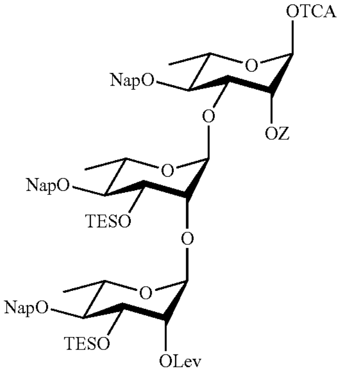

-continued

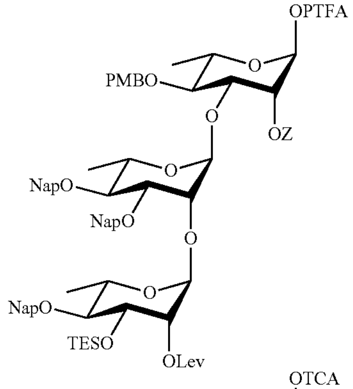

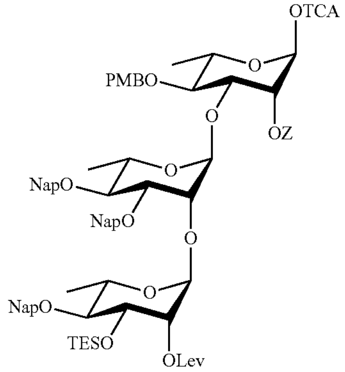

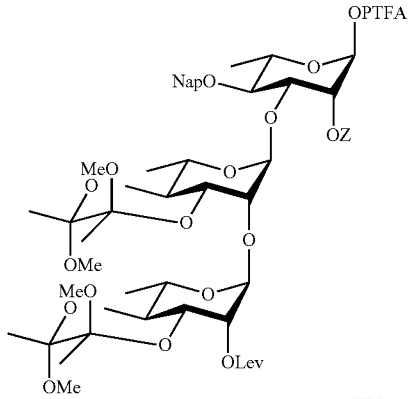

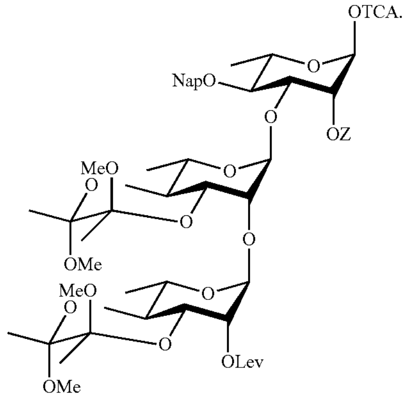

wherein:

TES is triethylsilyl;

Lev is levulinyl;

Nap is 2-naphytlmethyl;

PMB is para-methoxybenzyl.

By levulinyl (or levulinoyl) is meant the group $CH_3$—CO—$CH_2$—$CH_2$—CO—.

In the whole description, a wavy bond such as

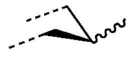

indicates that the corresponding substituent is in axial and/or in equatorial position.

Thus, a compound containing such a wavy bond exist as a mixture of the alpha and beta anomers, or only as the alpha or beta anomer.

In a particular embodiment, the protected $AB_ZC$-triosyl donor is of one of the above-mentioned formulae, wherein at least one of the TES groups or each TES group is independently replaced by a group chosen from TBS (tert-butyldimethylsilyl), TIPS (triisopropylsilyl), PMB, Nap or Lev.

In a particular embodiment, the protected $AB_ZC$-triosyl donor is of one of the above-mentioned formulae, wherein at least one of the BDA groups or each BDA (butane 2,3-diacetal) group is independently replaced by a group chosen from the 1,2-diacetal family, and in particular by CDA (cyclohexane-1,2-diacetal). The CDA group is for example described in Chem. Rev. (2001) 101, 53-80.

In a particular embodiment, the protected $AB_ZC$-triosyl donor is of one of the above-mentioned formulae, wherein at least one of the Nap groups or each Nap group is independently replaced by a group chosen from TBS, TIPS or PMB.

In a particular embodiment, the protected ${}_{Cl3Ac}$D-All acceptor is of following formula:

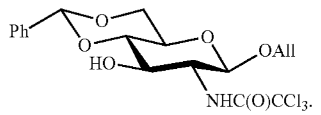

In a particular embodiment, the protected $AB_ZC_{Cl3Ac}$D-All compound is of one of the following formulae:

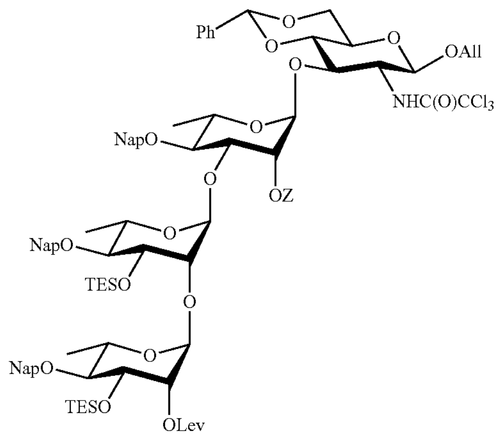

-continued

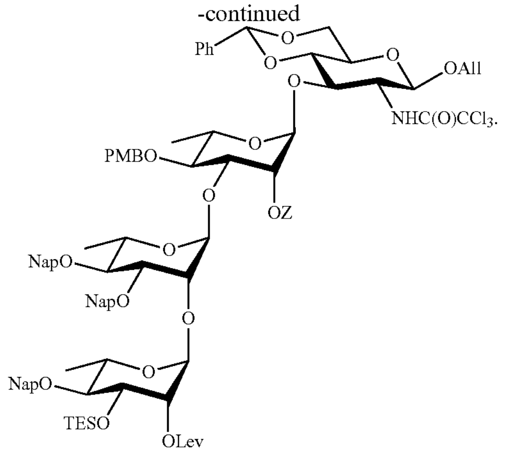

In a particular embodiment, the protected $AB_ZC_{Cl3Ac}D$-All compound is of one of the above-mentioned formulae, wherein at least one of the TES groups or each TES group is independently replaced by a group chosen from TBS, TIPS, PMB, Nap or Lev.

In a particular embodiment, the protected $AB_ZC_{Cl3Ac}D$-All compound is of one of the above-mentioned formulae, wherein at least one of the vicinal Nap/TES pairs or each vicinal Nap/TES pair is independently replaced by a group chosen from BDA or CDA.

By Nap/TES pair, is in particular meant a Nap that is vicinal to a Nap or TES group, as following:

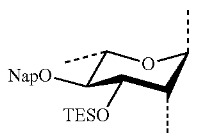

or

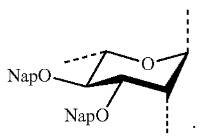

In a particular embodiment, the protected $AB_ZC_{Cl3Ac}D$-All compound is of one of the above-mentioned formulae, wherein at least one of the Nap groups or each Nap group is independently replaced by a group chosen from TBS, TIPS or PMB.

In another aspect, the present invention relates to a process of preparation of a compound of formula ($I_0$) as defined above, comprising the following steps:

(i) a step of contacting a protected $AB_ZC$-R acceptor with a protected $_TD$ donor to yield a protected $_TDAB_ZC$-R compound;

(ii) one or more steps of deprotection of the protected compound obtained in step (i) to give a compound of formula $_TDAB_ZC$-R.

In another aspect, the present invention relates to a process of preparation of a compound of formula (I) as defined above, comprising the following steps:

(i) a step of contacting a protected $AB_ZC$-All acceptor with a protected $_{Cl3Ac}D$ donor to yield a protected $_{Cl3Ac}DAB_ZC$-All compound;

(ii) one or more steps of deprotection of the protected compound obtained in step (i) to give a compound of formula $_{Cl3Ac}DAB_ZC$-All.

In particular, the $AB_ZC$-All acceptor is of one of the following formulae:

(a)

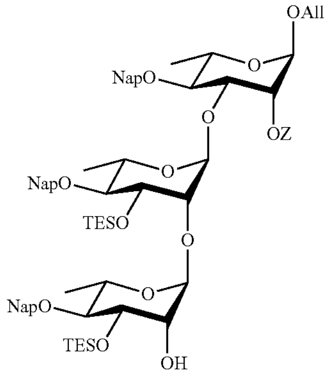

(b)

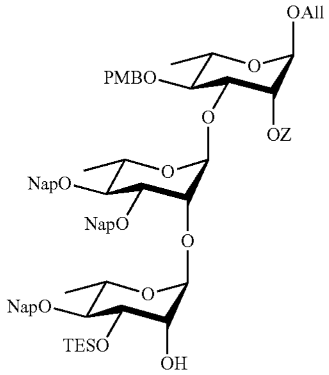

wherein:

TES is triethylsilyl;

Lev is levulinyl;

Nap is 2-naphtylmethyl;

PMB is para-methoxybenzyl.

In a particular embodiment, the $AB_ZC$-All acceptor compound is of one of the above-mentioned formulae, wherein at least one of the TES groups or each TES group is independently replaced by a group chosen from TBS, TIPS, PMB or Nap.

In a particular embodiment, the protected $AB_ZC_{Cl3Ac}D$-All compound is of one of the above-mentioned formulae, wherein at least one of the Nap groups or each Nap group is independently replaced by a group chosen from TBS, TIPS or PMB.

In a particular embodiment, the protected $AB_ZC$-All acceptor is of one of the above-mentioned formulae, wherein at least one of the vicinal Nap/TES pairs or each vicinal Nap/TES pair is independently replaced by a group chosen from BDA or CDA.

In particular, the $_{Cl3Ac}D$ donor is of formula $_{Cl3Ac}D$-Z', wherein Z' is PTFA or TCA, N-phenyltrifluoroacetimidoyl and TCA representing trichloroacetimidoyl.

In particular, the protected $_{Cl3Ac}D$ donor is of one of the following formulae or the corresponding oxazolines:

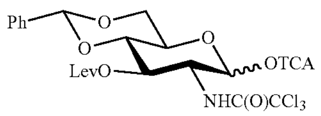

-continued
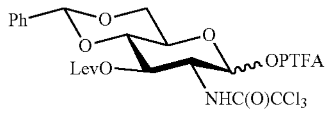
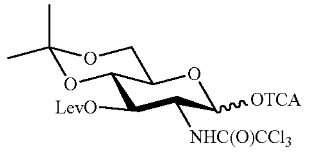
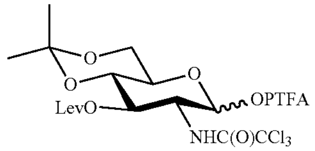
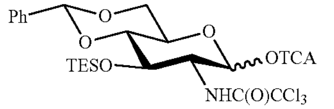
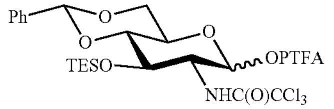
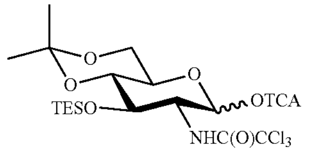
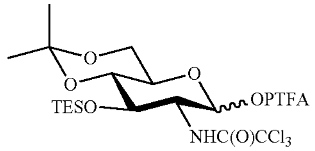
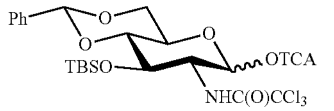
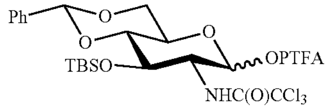
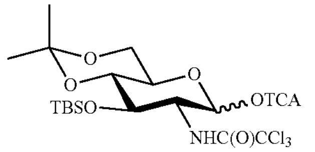
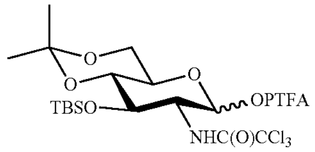
and notably:
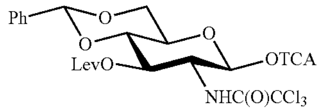
-continued
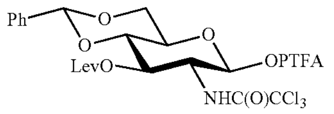
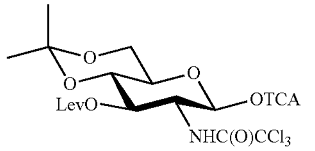
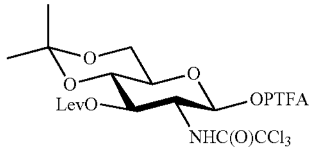
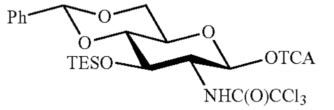
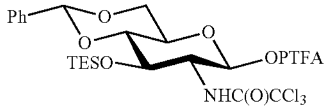
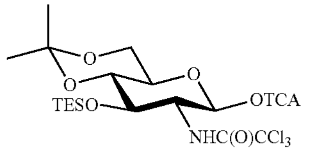
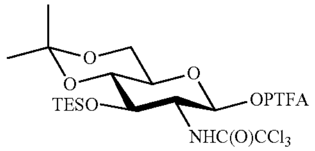
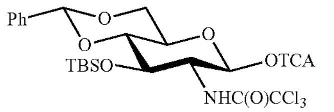
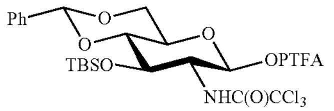
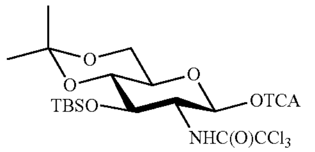
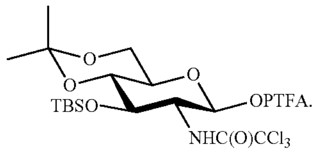

By "corresponding oxazoline" is meant a group as following:

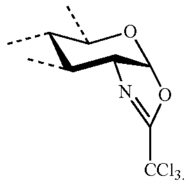

The 1,2-oxazoline may result from intramolecular cyclisation and loss of leaving group at position 1.

In a particular embodiment, the $_{Cl3Ac}$D donor compound is of one of the above-mentioned formulae, wherein the TES group is independently replaced by a group chosen from TIPS, PMB or Nap.

When the AB$_Z$C-All acceptor is of formula (a) and the $_{Cl3Ac}$D donor bears a TES protecting group in position $3_D$, there is in particular one step (ii) of deprotection only. In the other cases, there may be two steps of deprotection.

In a particular embodiment, the protected $_{Cl3Ac}$DAB$_Z$C-All compound is of one of the following formulae:

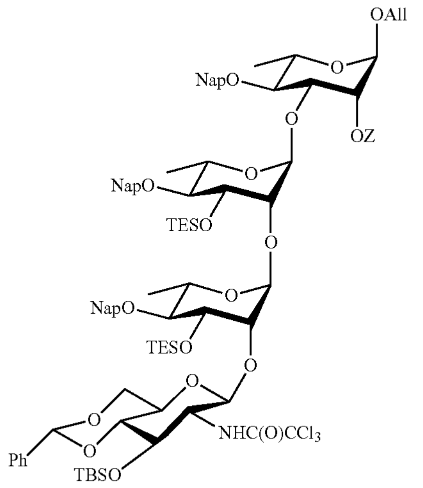

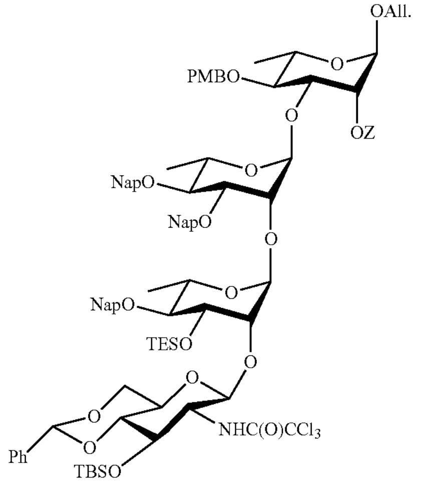

In a particular embodiment, the protected $_{Cl3Ac}$DAB$_Z$C-All compound is of one of the above-mentioned formulae, wherein at least one of the TES groups or each TES group is independently replaced by a group chosen from TBS, TIPS, PMB or Nap.

In a particular embodiment, the protected $_{Cl3Ac}$DAB$_Z$C-All compound is of one of the above-mentioned formulae, wherein at least one of the vicinal Nap/TES pairs or each vicinal Nap/TES pair is independently replaced by a group chosen from BDA or CDA.

In a particular embodiment, the protected $_{Cl3Ac}$DAB$_Z$C-All compound is of one of the above-mentioned formulae, wherein at least one of the TBS groups or each TBS group is replaced by a group chosen from PMB, Nap, Lev, TIPS or Lev.

In a particular embodiment, the protected $_{Cl3Ac}$DAB$_Z$C-All compound is of one of the above-mentioned formulae, wherein the 4,6-O-benzylidene acetal is replaced by an 4,6-O-isopropylidene acetal.

In another aspect, the present invention relates to a compound as defined by the following formulae, wherein Z is ClAc, BrAc or Ac:

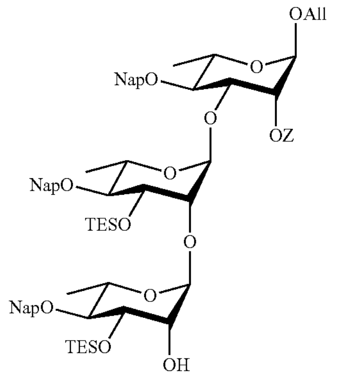

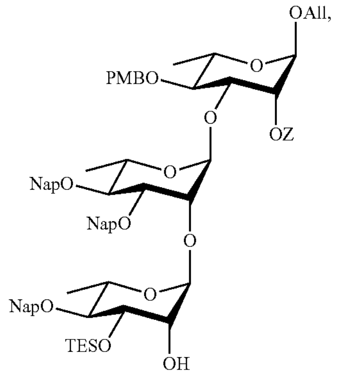

notably

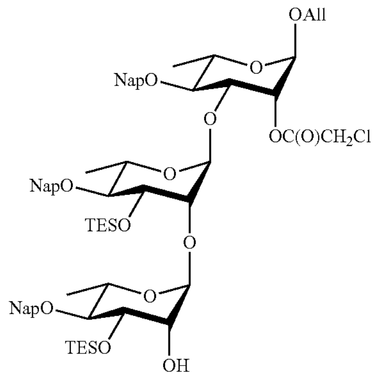

-continued

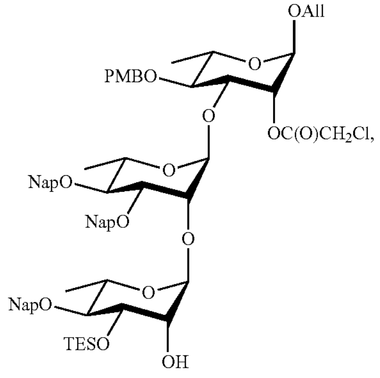

and

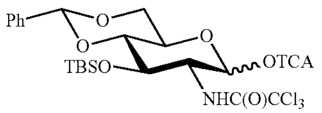

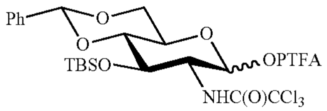

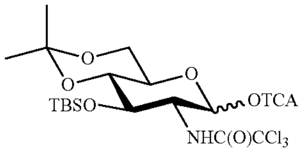

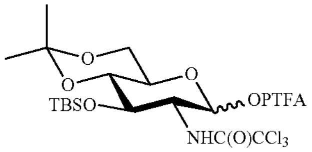

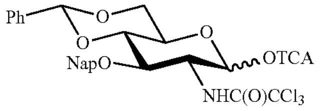

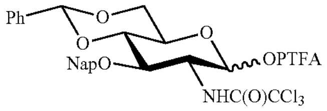

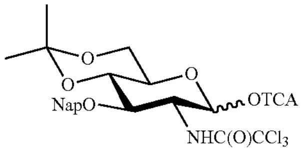

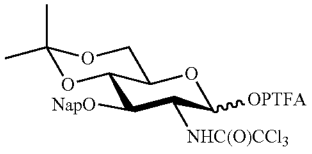

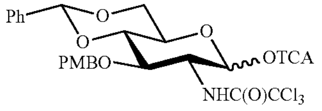

-continued

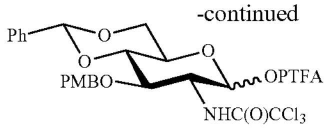

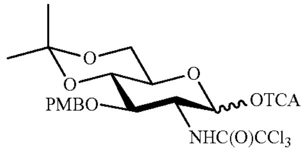

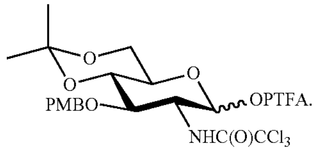

In a particular embodiment, the compound is of one of the above-mentioned formulae, wherein at least one of the vicinal Nap/TES pairs or each vicinal Nap/TES pair is independently replaced by a group chosen from BDA or CDA.

In another aspect, the present invention relates to a method of preparation of a saccharide comprising the following steps:

(i) a step of α-D-glucosylation of a compound of formula ($I_0$) as defined above by a sucrose-active enzyme selected from the group consisting of the enzymes of the GH13 family, the enzymes of the GH70 family, their variants, peptide fragments of said enzymes or variants, and modified enzymes/peptides derived from said enzymes, variants or fragments, to obtained a α-D-glucosylated $(_T D)_x AB_Z C(_T D)_y$-R compound;

(ii) optionally, and in particular when y is 1, a step of acetylation of the $3_A$ position and/or the $6_D$ position to obtained a $3_A$- and/or $6_D$-O-acetylated compound;

(iii) optionally, a step of cleavage of the ClAc or BrAc protecting group borne by C to obtain a $2_C$-hydroxylated compound;

(iv) optionally, a step of (a) conversion of the ClAc or BrAc protecting group borne by C into an acetyl group (Ac), (b) conversion of the Cl3Ac masking group borne by D into an acetyl group (Ac), (c) conversion of the allyl protecting group borne by D into a propyl (Pr) moiety followed if needed by the de-O-acylation of the $2_C$ position to obtained either a $2_C$-acylated or $2_C$-hydroxylated compound;

(v) optionally, a step of chain elongation at one or both of the ends of the compound resulting from the enzymatic α-D-glucosylation of the compound of formula (I) as defined above.

In another aspect, the present invention relates to a method of preparation of a saccharide comprising the following steps:

(i) a step of α-D-glucosylation of a compound of formula (I) as defined above by a sucrose-active enzyme selected from the group consisting of the enzymes of the GH13 family, the enzymes of the GH70 family, their variants, peptide fragments of said enzymes or variants, and modified enzymes/peptides derived from said enzymes, variants or fragments, to obtained a α-D-glucosylated $(_{Cl3Ac}D)_x AB_Z C(_{Cl3Ac}D)_y$-All compound;

(ii) optionally, and in particular when y is 1, a step of acetylation of the $3_A$ position and/or the $6_D$ position to obtained a $3_A$- and/or $6_D$-O-acetylated compound;

(iii) optionally, a step of cleavage of the ClAc or BrAc protecting group borne by C to obtain a $2_C$-hydroxylated compound;

(iv) optionally, a step of (a) conversion of the ClAc or BrAc protecting group borne by C into an acetyl group (Ac), (b) conversion of the Cl3Ac masking group borne by D into an acetyl group (Ac), (c) conversion of the allyl protecting group borne by D into a propyl (Pr) moiety followed if needed by the de-O-acylation of the $2_C$ position to obtained either a $2_C$-acylated or $2_C$-hydroxylated compound;

(v) optionally, a step of chain elongation at one or both of the ends of the compound resulting from the enzymatic α-D-glucosylation of the compound of formula (I) as defined above.

For example, step (ii) is a regioselective O-acylation at a primary hydroxyl group as well as at the equatorial hydroxyl group of 1,2-cis diol systems, which has been for instance described for polyols including carbohydrates by means of a borinic-acid catalyzed regioselective step (*J. Am. Chem. Soc.* (2011) 133, 3724-7). Alternatively, methods selective for the O-acylation of primary hydroxyl groups have been described including enzymatic O-acylation (Tetrahedron: Asymm. (2000) 11, 3647-51). Such transformations could also be in particular envisioned using an α-D-glucosylated $AB_{Ac}C_{Ac}D$-Pr substrate (wherein Pr=propyl, Ac=acetyl), as discussed below, or an α-D-glucosylated $ABC_{Ac}D$-Pr substrate.

Step (iii) may be achieved using thiourea (*Carbohydr. Res.* (2012) 356, 115-31).

About step (iv), the transformation of an α-D-glucosylated $(_{Cl3Ac}D)_xAB_ZC(_{Cl3Ac}D)_y$-All compound into the corresponding $(_{Ac}D)_xAB_{Ac}C(_{Ac}D_y)$-Pr (Pr=propyl, Ac=acetyl) may be achieved by Pd/C- or $Pd(OH)_2$-mediated hydrogenation (*Chem. Asian J.* (2017) 12, 419-39), while the subsequent de-O-acetylation at position $2_C$ is easily achievable by conventional transesterification, for example by use of a methanolic solution of sodium methoxide (*Chem. Eur. J.* (2016) 22, 10892-911).

About step (v), and, for example, taking advantage of the cis-vicinal diol in residue A (not applicable in the case enzymatic α-D-glucosylation would occur at position $3_A$ as in the *S. flexneri* 3a O-antigen), the $2_A$ and $3_A$ hydroxyl groups may be masked as an isopropylidene acetal either directly or post selective masking of the primary hydroxyl groups (*J. Org. Chem.* (2015) 80, 11237-57). Following the unmasking of the primary alcohols if needed, the remaining hydroxyl groups may then be masked with permanent protecting groups, preferentially benzyl ethers (*J. Org. Chem.* (2015) 80, 11237-57). Removal of the isopropylidene group under acid hydrolysis conditions, followed by selective masking of the $3_A$-OH by use of a protecting group orthogonal to all those in place (PMB or a silyl ether such as TES for example) may provide a pentasaccharide acceptor compatible with chain elongation at the $2_A$-OH. Alternatively, levulinylation of the hydroxyl group at position $2_A$ may provide a fully orthogonally protected pentasaccharide building block, which may be converted into a donor by selective removal of the allyl ether followed by activation of the obtained hemiacetal into an imidate donor (anomeric OPTFA or OTCA substitution) (*J. Org. Chem.* (2015) 80, 11237-57).

Herein, a chemo-enzymatic strategy to customized glycobricks suitable for the efficient synthesis of fragments of a diversity of *S. flexneri* O-antigens is disclosed. These glycobricks could be assembled into homo-oligomers, therefore providing a novel route to *S. flexneri* type-specific haptens, in particular through step (v) of chain elongation.

Homo-oligomers correspond to fragments encompassing n repeating units of the O-antigen from a selected *S. flexneri* serotype. Such a 15 mer hapten, corresponding to a three repeating unit fragment of the O-antigen, was for example identified for *S. flexneri* 2a (*J. Immunol.* (2009) 182, 2241-7, *Bioconjugate Chem.* (2016) 27, 883-92). Besides, available data suggest that at least a 15 mer, most probably a 20 mer, corresponding to three and four repeating unit fragments of the O-antigen would act as a suitable *S. flexneri* 3a hapten.

Glycoside hydrolases EC 3.2.1. and EC 2.4.1 are a widespread group of enzymes that hydrolyze the glycosidic bond between two or more carbohydrates, or between a carbohydrate and a non-carbohydrate moiety. A classification system for glycoside hydrolases, based on sequence similarity, has led to the definition of >100 different families. This classification is well known for the skilled in the art and is in particular available on the CAZy (http://www.cazy.org) web site.

By enzymes of the GH13 family is meant enzymes of glycoside hydrolase family 13 active on sucrose, that is a family of glycoside hydrolases, in particular amylosucrases (subfamily), which are also included in the «glucansucrase» family. This classification is well known for the skilled in the art and is in particular available on the CAZy (GH13.4 http://www.cazy.org/GH13_4.html) web site.

By enzymes of the GH13 family is meant in particular a wild type glycoside hydrolase, more particularly a transglucosylase, even more particularly an amylosucrase (EC 2.4.1.4) or a sucrose hydrolase (EC 3.2.1.-), as described in the patent application EP 2 100 966, even more particularly an amylosucrase from *Neisseria polysaccharea*, preferably selected from the group consisting of 1G5A, 1ZS2, 1 MVY, 1MW0, 1546, 1JGI, 1MW2, 1MW3, 1MW1 and 1JG9 proteins as found in the Protein Data Base (PDB, https://www.rcsb.org/) and as described in the patent application EP 2 100 966, or a mutant of the protein, as described in the patent application EP 2 100 966.

By enzymes of the GH70 family is meant transglucosylases produced by lactic acid bacteria from, e.g., *Streptococcus, Leuconostoc, Weisella* or *Lactobacillus* genera. This classification is well known for the skilled in the art and is in particular available on the CAZy (http://www.cazy.org/GH70.html) web site. In particular the enzymes of the GH70 family are branching sucrases and glucansucrases (EC 2.4.1). An enzyme of the GH70 family that can be used in the framework of this invention is an alternansucrase from *Leuconostoc citreum*, more particularly of strain NRRL B-1355.

In particular, said enzyme is selected from the group consisting of the BRS-B, BRS-B-D1, BRS-B-D2, BRS-C, BRS-A, BRS-D, BRS-E, GBD-CD2, GBD-CD2 W2135V, GBD-CD2 W2135C-F2136I, GBD-CD2 W2135S-F2136L, GBD-CD2 W2135I-F2136C, GBD-CD2 W2135N-F2136Y, GBD-CD2 W2135N, GBD-CD2 W2135I-F2136Y, GBD-CD2 W2135L, GBD-CD2 W2135C, GBD-CD2 W2135N-F2136H, GBD-CD2 W2135L-F2136L, GBD-CD2 W2135F-F2136I, GBD-CD2 W2135C-F2136N, GBD-CD2 W2135G, GBD-CD2 W2135F, GBD-CD2 F2163G, GBD-CD2 L2166I, GBD-CD2 F2163H, GBD-CD2 F2163G L2166I, GBD-CD2 A2162E F2163L, GBD-CD2 F2163L, GBD-CD2 F2163I-D2164E-L2166I enzymes.

In particular, said enzyme is selected from the group consisting of the BRS-B, BRS-B-D1, BRS-B-D2, BRS-C, BRS-A, BRS-D, BRS-E, GBD-CD2, GBD-CD2 W2135V, GBD-CD2 W2135C-F2136I, GBD-CD2 W2135S-F2136L, GBD-CD2 W2135I-F2136C, GBD-CD2 W2135C, GBD-CD2 W2135L-F2136L, GBD-CD2 W2135F-F2136I, GBD-CD2 W2135C-F2136N, GBD-CD2 W2135G, GBD-CD2 W2135F, GBD-CD2 F2163G, GBD-CD2 L2166I, GBD-CD2 F2163G L2166I, GBD-CD2 A2162E F2163L, GBD-CD2 F2163L, GBD-CD2 F2163I-D2164E-L2166I enzymes.

These enzymes are described in the art, as mentioned below in the examples.

In particular, said enzyme is a mutant of the BRS-B-D2 enzyme (SEQ ID NO: 4), as defined in the following table:

wherein:

L is E1→3 or Ac in position $3_A$;

M is E1→6 or Ac in position $6_D$;

a is 0 or 1, a' is:

0 or 1 when a is 1;

0 when a is 0;

e is 0 or 1;

c' is 0 or 1;

d and d' are 0 or 1, providing d+d'=0 or 1;

| Mutant | Mutations |
|---|---|
| M6 | W445A-L474I-E475K-F476V-A522G-I523L-S524A-R581I-K585L-K639L-D640L-I641L-Q642V |
| M14 | W445M-F446M-L474V-E475K-L477M-A522G-I523M-S524W-F525L-R581V-K585L-K639L-D640N-I641L-Q642V |
| M18 | W445L-L474I-E475R-F476Y-I523P-S524D-F525W-R581I-K585L-K639I-D640N-I641V-Q642L-I646I |
| M21 | W445L-I523I-S524D-P561D-R581W-D582L-K639L-I641I-D643E-I646V-M660W-S661T |
| M23 | W445P-S524M-P561D-R581L-D582L-Q642L-D643E-I646T-M660D-S661T |
| M28 | W445E-S524D-P561S-R581I-D582L-K639L-Q642W-D643E-I646W-M660Y-S661S |
| M30 | W445L-F525W-P561L-R581M-D582Q-K639V-Q642V-D643E-I646T-M660M-S661T |
| M31 | W445L-F525W-P561L-R581M-D582E-K639I-Q642I-D643L-I646W-M660V-S661T |
| M34 | W445L-F525W-P561L-R581M-D582A-K639V-Q642L-D643E-I646V-M660P-S661T |
| M35 | W445A-L477M-K639A-I641V-D643V-H647G-I648T-M660H-S661T |
| M40 | W445D-L478M-K639V-I641I-Q642T-D643I-I646V-H647S-I648L-M660S-S661T |
| M41 | W445L-F446M-K639L-I641L-Q642E-I646V-H647S-I648L-S661T |

In particular, said enzyme is BRS-B.

In particular, said enzyme is BRS-B-D2.

In particular, said enzyme is GBD-CD2 F2163G.

In particular, said enzyme is GBD-CD2 W2135I-F2136C or GBD-CD2 W2135L-F2136L or GBD-CD2 W2135S-F2136L.

In particular, said saccharide is a fragment of O-antigens from *S. flexneri*, in particular of serotype 1a, 1b, 2a, 2b, 3a, X, 4a, 4b, 5a, 5b, 7a or 7b.

In particular, said saccharide comprises the following fragment:

$$-[((E1\rightarrow 2)_{a'}(E1\rightarrow 4)_{a}(M)_{b\ Ac}D)_{x}(L)_{c}A(E1\rightarrow 3)_{d}B(E1\rightarrow 4)_{e(Ac)z}C((E1\rightarrow 2)_{a'}(E1\rightarrow 4)_{a}(M)_{b\ Ac}D)_{y}]_{n}-$$

wherein:

L is E1→3 or Ac in position $3_A$;

M is E1→6 or Ac in position $6_D$;

a and b is 0 or 1, providing a+b=0 or 1;

a' is:

0 or 1 when a is 1;

0 when a is 0;

c, d and e are 0 or 1;

a, b, c, d and e being in particular such as a+b+c+d+e=1 or 2;

z is at each occurrence independently 0 or 1, z being in particular at all occurrences 0 or 1;

E represents a residue α-D-Glcp-;

n is an integer superior or equal to 1, in particular comprised between 1 and 10.

In particular, said saccharide comprises the following fragment:

$$-[((E1\rightarrow 2)_{a'}(E1\rightarrow 4)_{a}(M)_{b\ Ac}D)_{x}(L)_{c}(E1\rightarrow 4)_{c'}A(E1\rightarrow 3)_{d}(E1\rightarrow 4)_{d'}B(E1\rightarrow 4)_{e(Ac)z}C((E1\rightarrow 2)_{a'}(E1\rightarrow 4)_{a}(M)_{b\ Ac}D)_{y}]_{n}-$$

when L is Ac, c is at each occurrence independently 0 or 1, c being in particular at all occurrences 0 or 1, providing c+c'=0 or 1;

when L is E1→3, c is 0 or 1, providing c+c'=0 or 1;

when M is Ac, b is at each occurrence independently 0 or 1, b being in particular at all occurrences 0 or 1, providing a+b=0 or 1;

when M is E1→6, b is 0 or 1, providing a+b=0 or 1;

a, b, c, c', d, d' and e being in particular such as a+b+c+c'+d+d'+e=1, 2 or 3.

z is at each occurrence independently 0 or 1, z being in particular at all occurrences 0 or 1;

E represents a residue α-D-Glcp-;

n is an integer superior or equal to 1, in particular comprised between 1 and 10.

In the above and below paragraphs, L and/or M are in particular Ac at at least one occurrence, more particularly at all occurrences.

In the above and below paragraphs, L and/or M are in particular E1→3 and E1→6 respectively, at all occurrences.

In particular, said saccharide comprises the following fragment:

$$-[((E1\rightarrow 2)_{a'}(E1\rightarrow 4)_{a}(M)_{b\ Ac}D)_{x}(L)_{c}A(E1\rightarrow 3)_{d}B(E1\rightarrow 4)_{e(Ac)z}C((E1\rightarrow 2)_{a'}(E1\rightarrow 4)_{a}(M)_{b\ Ac}D)_{y}]_{n}-$$

All wherein:

L is E1→3 or Ac in position $3_A$;

M is E1→6 or Ac in position $6_D$;

a and b is 0 or 1, providing a+b=0 or 1;

a' is:

0 or 1 when a is 1;

0 when a is 0;

c, d and e are 0 or 1;

a, b, c, d and e being in particular such as a+b+c+d+e=1 or 2;

z is at each occurrence independently 0 or 1, z being in particular at all occurrences 0 or 1;

E represents a residue α-D-Glcp-;

n is an integer superior or equal to 1, in particular comprised between 1 and 10.

In particular, said saccharide comprises the following fragment:

$$\text{-}[((E1\rightarrow2)_{a'}(E1\rightarrow4)_a(M)_{b\ Ac}D)_x(L)_c(E1\rightarrow4)_{c'}A(E1\rightarrow3)_d(E1\rightarrow4)_{d'}B(E1\rightarrow4)_{e(Ac)z}C((E1\rightarrow2)_{a'}(E1\rightarrow4)_a(M)_{b\ Ac}D)_y]_n\text{-All}$$

wherein:

L is E1→3 or Ac in position $3_A$;

M is E1→6 or Ac in position $6_D$;

a is 0 or 1, a' is:

0 or 1 when a is 1;

0 when a is 0;

e is 0 or 1;

c' is 0 or 1;

d and d' are 0 or 1, providing d+d'=0 or 1;

when L is Ac, c is at each occurrence independently 0 or 1, c being in particular at all occurrences 0 or 1, providing c+c'=0 or 1;

when L is E1→3, c is 0 or 1, providing c+c'=0 or 1;

when M is Ac, b is at each occurrence independently 0 or 1, b being in particular at all occurrences 0 or 1, providing a+b=0 or 1;

when M is E1→6, b is 0 or 1, providing a+b=0 or 1;

a, b, c, c', d, d' and e being in particular such as a+b+c+c'+d+d'+e=1, 2 or 3.

In particular, said saccharide comprises the following fragment:

$$\text{-}[((E1\rightarrow2)_{a'}(E1\rightarrow4)_a(M)_{b\ Ac}D)_x(L)_cA(E1\rightarrow3)_dB(E1\rightarrow4)_{e(Ac)z}C((E1\rightarrow2)_{a'}(E1\rightarrow4)_a(M)_{b\ Ac}D)_y]_n\text{-}Pr$$

wherein:

L is E1→3 or Ac in position $3_A$;

M is E1→6 or Ac in position $6_D$;

a and b is 0 or 1, providing a+b=0 or 1;

a' is:

0 or 1 when a is 1;

0 when a is 0;

c, d and e are 0 or 1;

a, b, c, d and e being in particular such as a+b+c+d+e=1 or 2;

z is at each occurrence independently 0 or 1, z being in particular at all occurrences 0 or 1;

E represents a residue α-D-Glcp-;

n is an integer superior or equal to 1, in particular comprised between 1 and 10;

Pr is propyl.

In particular, said saccharide comprises the following fragment:

$$\text{-}[((E1\rightarrow2)_{a'}(E1\rightarrow4)_a(M)_{b\ Ac}D)_x(L)_c(E1\rightarrow4)_{c'}A(E1\rightarrow3)_d(E1\rightarrow4)_{d'}B(E1\rightarrow4)_e(Ac)zC((E1\rightarrow2)_{a'}(E1\rightarrow4)_a(M)_{b\ Ac}D)_y]_n\text{-}Pr$$

wherein:

L is E1→3 or Ac in position $3_A$;

M is E1→6 or Ac in position $6_D$;

a is 0 or 1, a' is:

0 or 1 when a is 1;

0 when a is 0;

e is 0 or 1;

c' is 0 or 1;

d and d' are 0 or 1, providing d+d'=0 or 1;

when L is Ac, c is at each occurrence independently 0 or 1, c being in particular at all occurrences 0 or 1, providing c+c'=0 or 1;

when L is E1→3, c is 0 or 1, providing c+c'=0 or 1;

when M is Ac, b is at each occurrence independently 0 or 1, b being in particular at all occurrences 0 or 1, providing a+b=0 or 1;

when M is E1→6, b is 0 or 1, providing a+b=0 or 1;

a, b, c, c', d, d' and e being in particular such as a+b+c+c'+d+d'+e=1, 2 or 3;

Pr is propyl.

In particular, said saccharide comprises the following fragment:

$$\text{-}[((E1\rightarrow2)_{a'}(E1\rightarrow4)_a(E1\rightarrow6)_{b\ Ac}D)_x(E1\rightarrow3)_cA(E1\rightarrow3)_dB(E1\rightarrow4)_{c(Ac)z}C((E1\rightarrow2)_{a'}(E1\rightarrow4)_a(E1\rightarrow6)_{b\ Ac}D)_y]_n\text{-}$$

wherein:

a and b is 0 or 1, providing a+b=0 or 1;

a' is:

0 or 1, when a is 1;

0 when a is 0;

c, d and e are 0 or 1;

a, b, c, d and e being in particular such as a+b+c+d+e=1 or 2;

z is at each occurrence independently 0 or 1, z being in particular at all occurrences 0 or 1;

E represents a residue α-D-Glcp-;

n is an integer superior or equal to 1, in particular comprised between 1 and 10.

In particular, said saccharide comprises the following fragment:

$$\text{-}[((E1\rightarrow2)_{a'}(E1\rightarrow4)_a(E1\rightarrow6)_{b\ Ac}D)_x(E1\rightarrow3)_c(E1\rightarrow4)_{c'}A(E1\rightarrow3)_d(E1\rightarrow4)_{d'}B(E1\rightarrow4)_{e(Ac)z}C((E1\rightarrow2)_{a'}(E1\rightarrow4)_a(E1\rightarrow6)_bD)_y]_n\text{-}$$

wherein:

a is 0 or 1, a' is:

0 or 1 when a is 1;

0 when a is 0;

e is 0 or 1;

c' is 0 or 1;

d and d' are 0 or 1, providing d+d'=0 or 1;

c is 0 or 1, providing c+c'=0 or 1;

b is 0 or 1, providing a+b=0 or 1;

a, b, c, c', d, d' and e being in particular such as a+b+c+c'+d+d'+e=1, 2 or 3.

In particular, said saccharide comprises the following fragment:

$$\text{-}[((E1\rightarrow2)_{a'}(E1\rightarrow4)_a(Ac1\rightarrow6)_{b\ Ac}D)_x(Ac1\rightarrow3)_c(E1\rightarrow4)_{c'}(E1\rightarrow3)_d(E1\rightarrow4)_{d'}B(E1\rightarrow4)_{e(Ac)z}C((E1\rightarrow2)_{a'}(E1\rightarrow4)_a(E1\rightarrow6)_bD)_y]_n\text{-}$$

wherein:

a is 0 or 1, a' is:

0 or 1 when a is 1;

0 when a is 0;

e is 0 or 1;

c' is 0 or 1;

d and d' are 0 or 1, providing d+d'=0 or 1;

c is at each occurrence independently 0 or 1, c being in particular at all occurrences 0 or 1, providing c+c'=0 or 1;

b is at each occurrence independently 0 or 1, b being in particular at all occurrences 0 or 1, providing a+b=0 or 1;

a, b, c, c', d, d' and e being in particular such as a+b+c+c'+d+d'+e=1, 2 or 3.

In particular, said saccharide comprises the following fragment:

$$-[((E1\rightarrow2)_{a'}(E1\rightarrow4)_{a}(E1\rightarrow6)_{b\ Ac}D)_{x}(Ac1\rightarrow3)_{c}(E1\rightarrow4)_{c'}(E1\rightarrow3)_{d}(E1\rightarrow4)_{d'}B(E1\rightarrow4)_{e(Ac)z}C((E1\rightarrow2)_{a'}(E1\rightarrow4)_{a}(E1\rightarrow6)_{b}D)_{y}]_{n}-$$

wherein:

a is 0 or 1, a' is:

0 or 1 when a is 1;

0 when a is 0;

e is 0 or 1;

c' is 0 or 1;

d and d' are 0 or 1, providing d+d'=0 or 1;

c is at each occurrence independently 0 or 1, c being in particular at all occurrences 0 or 1, providing c+c'=0 or 1;

b is 0 or 1, providing a+b=0 or 1;

a, b, c, c', d, d' and e being in particular such as a+b+c+c'+d+d'+e=1, 2 or 3.

In particular, said saccharide comprises the following fragment:

$$-[((E1\rightarrow2)_{a'}(E1\rightarrow4)_{a}(Ac1\rightarrow6)_{b\ Ac}D)_{x}(E1\rightarrow3)_{c}(E1\rightarrow4)_{c'}A(E1\rightarrow3)_{d}(E1\rightarrow4)_{d'}B(E1\rightarrow4)_{e(Ac)z}C((E1\rightarrow2)_{a'}(E1\rightarrow4)_{a}(E1\rightarrow6)_{b}D)_{y}]_{n}-$$

wherein:

a is 0 or 1, a' is:

0 or 1 when a is 1;

0 when a is 0;

e is 0 or 1;

c' is 0 or 1;

d and d' are 0 or 1, providing d+d'=0 or 1;

, c is 0 or 1, providing c+c'=0 or 1;

b is at each occurrence independently 0 or 1, b being in particular at all occurrences 0 or 1, providing a+b=0 or 1;

a, b, c, c', d, d' and e being in particular such as a+b+c+c'+d+d'+e=1, 2 or 3.

By "z is at each occurrence independently 0 or 1" is meant that for each occurrence of the repeating unit repeated n times, z can be independently 0 or 1. In other terms, for n superior or equal to 2, position $2_C$ can be non-O-acetylated, fully O-acetylated or partially acetylated within said saccharide.

By "when L is Ac, c is at each occurrence independently 0 or 1" is meant that for each occurrence of the repeating unit repeated n times, c can be independently 0 or 1, when L is Ac. In other terms, for n superior or equal to 2, position $3_A$ can be non-O-acetylated, fully O-acetylated or partially acetylated within said saccharide.

By "when M is Ac, b is at each occurrence independently 0 or 1" is meant that for each occurrence of the repeating unit repeated n times, b can be independently 0 or 1, when M is Ac. In other terms, for n superior or equal to 2, position $6_D$ can be non-O-acetylated, fully O-acetylated or partially acetylated within said saccharide.

More particularly, said saccharide comprises the following fragment:

$$[AB_{(Ac)z}C(E1\rightarrow6)_{Ac}D]_{n}-$$

In a particular embodiment, the sucrose-active enzyme is selected from the group consisting of the BRS-B, BRS-B-D2, BRS-C, BRS-A, BRS-D, BRS-E, GBD-CD2, GBD-CD2 W2135V, GBD-CD2 W2135C-F2136I, GBD-CD2 W2135S-F2136L, GBD-CD2 W2135I-F2136C, GBD-CD2 W2135C, GBD-CD2 W2135L-F2136L, GBD-CD2 W2135F-F2136I, GBD-CD2 W2135C-F2136N, GBD-CD2 W2135G, GBD-CD2 W2135F, GBD-CD2 F2163G, GBD-CD2 L2166I, GBD-CD2 F2163G L2166I, GBD-CD2 A2162E F2163L, GBD-CD2 F2163L, GBD-CD2 F2163I-D2164E-L2166I enzymes, and the BRS-B-D2 M6, BRS-B-D2 M21, BRS-B-D2 M23, BRS-B-D2 M28, BRS-B-D2 M30, BRS-B-D2 M31, BRS-B-D2 M34, BRS-B-D2 M35, BRS-B-D2 M40 and BRS-B-D2 M41 enzymes, the enzyme being more particularly BRS-B.

More particularly, said saccharide comprises the following fragment:

$$[(E1\rightarrow3)AB_{(Ac)z}C_{Ac}D]_{n}-$$

In a particular embodiment, the sucrose-active enzyme is selected from the group consisting of the BRS-B, BRS-B-D2, BRS-C, BRS-A, BRS-D, BRS-E, GBD-CD2, GBD-CD2 W2135V, GBD-CD2 W2135C-F2136I, GBD-CD2 W2135S-F2136L, GBD-CD2 W2135I-F2136C, GBD-CD2 W2135N-F2136Y, GBD-CD2 W2135N, GBD-CD2 W2135I-F2136Y, GBD-CD2 W2135L, GBD-CD2 W2135C, GBD-CD2 W2135N-F2136H, GBD-CD2 W2135L-F2136L, GBD-CD2 W2135F-F2136I, GBD-CD2 W2135C-F2136N, GBD-CD2 W2135G, GBD-CD2 W2135F, GBD-CD2 F2163G, GBD-CD2 L2166I, GBD-CD2 F2163H, GBD-CD2 F2163G L2166I, GBD-CD2 A2162E F2163L, GBD-CD2 F2163L, GBD-CD2 F2163I-D2164E-L2166I enzymes, and the BRS-B-D2 M14, BRS-B-D2 M18, BRS-B-D2 M21, BRS-B-D2 M23, BRS-B-D2 M28, BRS-B-D2 M30, BRS-B-D2 M34, BRS-B-D2 M35, BRS-B-D2 M40 and BRS-B-D2 M41 enzymes, the enzyme being more particularly BRS-B, GBD-CD2 W2135G or GBD-CD2 F2163I-D2164E-L2166I.

More particularly, said saccharide comprises the following fragment:

$$[(E1\rightarrow4)AB_{(Ac)z}C_{Ac}D]_{n}-$$

In a particular embodiment, the sucrose-active enzyme is selected from the group consisting of the BRS-B, BRS-B-D2, BRS-C, BRS-A, BRS-D, BRS-E, GBD-CD2, GBD-CD2 W2135V, GBD-CD2 W2135C-F2136I, GBD-CD2 W2135S-F2136L, GBD-CD2 W2135I-F2136C, GBD-CD2 W2135N-F2136Y, GBD-CD2 W2135N, GBD-CD2 W2135I-F2136Y, GBD-CD2 W2135L, GBD-CD2 W2135C, GBD-CD2 W2135N-F2136H, GBD-CD2 W2135L-F2136L, GBD-CD2 W2135F-F2136I, GBD-CD2 W2135C-F2136N, GBD-CD2 W2135G, GBD-CD2 W2135F, GBD-CD2 F2163G, GBD-CD2 L2166I, GBD-CD2 F2163H, GBD-CD2 F2163G L2166I, GBD-CD2 A2162E F2163L, GBD-CD2 F2163L, GBD-CD2 F2163I-D2164E-L2166I enzymes, and the BRS-B-D2 M14, BRS-B-D2 M18, BRS-B-D2 M21, BRS-B-D2 M23, BRS-B-D2 M28, BRS-B-D2 M30, BRS-B-D2 M34, BRS-B-D2 M35, BRS-B-D2 M40 and BRS-B-D2 M41 enzymes, the enzyme being more particularly BRS-B, GBD-CD2 W2135G or GBD-CD2 F2163I-D2164E-L2166I.

More particularly, said saccharide comprises the following fragment:

$$-[A(E1\rightarrow4)B_{(Ac)z}C_{Ac}D]_{n}-$$

In a particular embodiment, the sucrose-active enzyme is selected from the group consisting of the GBD-CD2

W2135S-F2136L, GBD-CD2 W2135I-F2136C, GBD-CD2 W2135L-F2136L enzymes, and the BRS-B-D2 M14, BRS-B-D2 M18, BRS-B-D2 M21, BRS-B-D2 M23, BRS-B-D2 M28, BRS-B-D2 M30, BRS-B-D2 M35, BRS-B-D2 M40 and BRS-B-D2 M41 enzymes.

In another aspect, the present invention relates to a compound of one of the following formulae:

$((E1\rightarrow2)_a(E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ ClAc}C((E1\rightarrow2)_a(E1\rightarrow4)_a(E1\rightarrow6)_{b\ Cl3Ac}D)_y$-All;

$((E1\rightarrow2)_a(E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_eC((E1\rightarrow2)_a(E1\rightarrow4)_a(E1\rightarrow6)_{b\ Cl3Ac}D)_y$-All;

$((E1\rightarrow2)_a(E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ ClAc}C((E1\rightarrow2)_a(E-4)_a(E1\rightarrow6)_{bCl3Ac}D)_y$-All;

$((E1\rightarrow2)_a(E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ Cl3Ac}C((E1\rightarrow2)_a(E-4)_a(E1\rightarrow6)_{b\ Cl3Ac}D)_y$;

$((E1\rightarrow2)_a(E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ ClAc}C((E1\rightarrow2)_a(E1\rightarrow4)_a(E1\rightarrow6)_{b\ Cl3Ac}D)_y$;

$((E1\rightarrow2)_a(E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_eC((E1\rightarrow2)_a(E1\rightarrow4)_a(E1\rightarrow6)_{b\ Cl3Ac}D)_y$;

$((E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ ClAc}C((E1\rightarrow4)_a(E1\rightarrow6b)_{Cl3Ac}D)_y$-All;

$((E1\rightarrow4)_a(E1\rightarrow6)_{b\ Cl3Ac}D)_x(E1\rightarrow3)_c(E1\rightarrow4)_cA(E1\rightarrow3)_d(E1\rightarrow4)_dB(E1\rightarrow4)_eC((E1\rightarrow4)_a(E1\rightarrow6)_{b\ Cl3Ac}D)_y$-All;

$((E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ Ac}C((E1\rightarrow4)_a(E1\rightarrow6)_{b\ Cl3Ac}D)_y$-All;

$((E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ Ac}C((E1\rightarrow4)_a(E1\rightarrow6)_{b\ Cl3Ac}D)_y$;

$((E1\rightarrow4)_a(E1\rightarrow6)_{bCl3Ac}D)_x(E1\rightarrow3)_c(E1\rightarrow4)_cA(E1\rightarrow3)_d(E1\rightarrow4)_dB(E1\rightarrow4)_{e\ Cl3Ac}C((E1\rightarrow4)_a(E1\rightarrow6)_{b\ Cl3Ac}D)_y$;

$((E1\rightarrow4)_a(E1\rightarrow6)_{b\ Cl3Ac}D)_x(E1\rightarrow3)_c(E1\rightarrow4)_cA(E1\rightarrow3)_d(E1\rightarrow4)_dB(E1\rightarrow4)_eC((E1\rightarrow4)_a(E1\rightarrow^{6})_{b\ Cl3Ac}D)_y$;

$((E1\rightarrow4)_a(E1\rightarrow6)_{b\ Cl3Ac}D)_x(E1\rightarrow3)_cA(E1\rightarrow3)_dB(E1\rightarrow4)_{e\ ClAc}C((E1\rightarrow4)_a(E1\rightarrow6)_{b\ Cl3Ac}D)_y$-All;

$((E1\rightarrow4)_a(E1\rightarrow6)_{b\ Cl3Ac}D)_x(E1\rightarrow3)_cA(E1\rightarrow3)_dB(E1\rightarrow4)_eC((E1\rightarrow4)_a(E1\rightarrow6)_{b\ Cl3Ac}D)_y$-All;

$((E1\rightarrow4)_a(E1\rightarrow6)_{bCl3Ac}D)_x(E1\rightarrow3)_cA(E1\rightarrow3)_dB(E1\rightarrow4)_{e\ Ac}C((E1\rightarrow4)_a(E1\rightarrow6)_{b\ Cl3Ac}D)_y$-All;

$((E1\rightarrow4)_a(E1\rightarrow6)_{b\ Cl3Ac}D)_x(E1\rightarrow3)_cA(E1\rightarrow3)_dB(E1\rightarrow4)_{e\ Ac}C((E1\rightarrow4)_a(E1\rightarrow6)_{bCl3Ac}D)_y$;

$((E1\rightarrow4)_a(E1\rightarrow6)_{b\ Cl3Ac}D)_x(E1\rightarrow3)_cA(E1\rightarrow3)_dB(E1\rightarrow4)_{e\ ClAc}C((E1\rightarrow4)_a(E1\rightarrow6)_{b\ Cl3Ac}D)_y$;

$((E1\rightarrow4)_a(E1\rightarrow6)_{b\ Cl3Ac}D)_x(E1\rightarrow3)_cA(E1\rightarrow3)_dB(E1\rightarrow4)_eC((E1\rightarrow4)_a(E1\rightarrow6)_{b\ Cl3Ac}D)_y$;

$AB_{ClAc}C(E1\rightarrow6)_{Cl3Ac}D$-All;

$ABC(E1\rightarrow6)_{Cl3Ac}D$-All;

$AB_{Ac}C(E1\rightarrow6)_{Cl3Ac}D$-All;

$AB_{Ac}C(E1\rightarrow6)_{Cl3Ac}D$;

$AB_{ClAc}C(E1\rightarrow6)_{Cl3Ac}D$;

$ABC(E1\rightarrow6)_{Cl3Ac}D$ $(E1\rightarrow3)AB_{ClAc}C_{Cl3Ac}D$-All;

$(E1\rightarrow3)ABC_{Cl3Ac}D$-All;

$(E1\rightarrow3)AB_{Ac}C_{Cl3Ac}D$-All;

$(E1\rightarrow3)AB_{Ac}C_{Cl3Ac}D$;

$(E1\rightarrow3)AB_{ClAc}C_{Cl3Ac}D$;

$(E1\rightarrow3)ABC_{Cl3Ac}D$;

$(E1\rightarrow4)AB_{ClAc}C_{Cl3Ac}D$-All;

$(E1\rightarrow4)ABC_{Cl3Ac}D$-All;

$(E1\rightarrow4)AB_{Ac}C_{Cl3Ac}D$-All;

$(E1\rightarrow4)AB_{Ac}C_{Cl3Ac}D$;

$(E1\rightarrow4)AB_{ClAc}C_{Cl3Ac}D$;

$(E1\rightarrow4)ABC_{Cl3Ac}D$;

$A(E1\rightarrow4)B_{ClAc}C_{Cl3Ac}D$-All;

$A(E1\rightarrow4)BC_{Cl3Ac}D$-All;

$A(E1\rightarrow4)B_{Ac}C_{Cl3Ac}D$-All;

$A(E1\rightarrow4)B_{Ac}C_{Cl3Ac}D$;

$A(E1\rightarrow4)B_{ClAc}C_{Cl3Ac}D$;

$A(E1\rightarrow4)BC_{Cl3Ac}D$.

In another aspect, the invention concerns an enzyme selected from the group comprising the enzymes BRS-D-2 M6, BRS-D-2 M14, BRS-D-2 M18, BRS-D-2 M21, BRS-D-2 M23, BRS-D-2 M28, BRS-D-2 M30, BRS-D-2 M31, BRS-D-2 M34, BRS-D-2 M35, BRS-D-2 M40, BRS-D-2 M41 as defined above, and their variants.

Synthesis

Compounds of formula I may be obtained thanks to a [3+1] strategy as shown below. For instance, an $AB_{ClAc}C$ rhamnotriosyl donor encompassing protecting groups orthogonal to an allyl ether (All), a N-trichloroacetyl ($Cl_3Ac$) and chloroacetyl moiety (ClAc), was reacted with a D acceptor. A two-step deprotection process gave the $AB_{ClAc}C_{Cl3Ac}D$-All acceptor. Protection and deprotection techniques are for instance described by P. G. M. Wuts and T. W. Greene (Greene's *Protective Groups in Organic Synthesis*, Fourth Edition; Wiley-Interscience, 2006; or Greene's *Protective Groups in Organic Synthesis*, fifth Edition; Wiley-Interscience, 2014).

Advantageously, rhamnoses A, B and C are in particular built from a single precursor.

A suitable synthetic pathway may be the following:

Definitions

The following terms and expressions contained herein are defined as follows:

As used herein, a range of values in the form "x-y" or "x to y", or "x through y", include integers x, y, and the integers there between. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term (E) means that the saccharide following the term (E) bears a residue α-D-Glcp-. For example, A(E)B means that B bears a residue α-D-Glcp-. Furthermore, $(E1\rightarrow6)_{Ac}D$ means that the residue $_{Ac}D$ bears a residue α-D-Glcp- linked at its primary hydroxyl group (position $6_D$-OH).

As used herein, the term "donor" more particularly refers to a mono-, oligo- or polysaccharide bearing a leaving group at the anomeric position.

As used herein, the term "acceptor" more particularly refers to a mono-, oligo- or polysaccharide having at least a free hydroxyl group, in general other than the anomeric hydroxyl, preferably at least the free hydroxyl group corresponding to the elongation site of the growing chain.

A variant is derived from an enzyme of the GH13 or GH70 family, such as amylosucrases in the case of GH13 family, and branching sucrases and glucansucrases in the case of GH70 family, by the introduction of mutations (deletion(s), insertion(s) and/or substitutions(s)) at specific positions in the sequence of said enzyme, while retaining the ability of said enzyme to catalyze α-D-glucosylation.

In particular, the amino acid sequence of said variant has at least 50% identity, or by order of increasing preference at least 40%, 42%, 45%, 47%, 50%, 52%, 55%, 57%, 60%, 62%, 65%, 70%, 72%, 75%, 77%, 80%, 82%, 85%, 87%, 90%, 92%, 95%, 96%, 97%, 98%, 99% or 100% identity, with the amino acid sequence of the corresponding enzyme of the GH13 or GH70 family.

The percent amino acid sequence identity is defined as the percent of amino acid residues in a Compared Sequence that are identical to the Reference Sequence after aligning the sequences and introducing gaps if necessary, to achieve the maximum sequence identity. The Percent identity is then determined according to the following formula: Percent identity=100×[1−(C/R)], wherein C is the number of differences between the Reference Sequence and the Compared sequence over the entire length of the Reference sequence, wherein (i) each amino acid in the Reference Sequence that does not have a corresponding aligned amino acid in the Compared Sequence, (ii) each gap in the Reference Sequence, and (iii) each aligned amino acid in the Reference Sequence that is different from an amino acid in the Compared Sequence constitutes a difference; and R is the number amino acids in the Reference Sequence over the length of the alignment with the Compared Sequence with any gap created in the Reference Sequence also being counted as an amino acid.

Unless otherwise specified, the percent of identity between two protein sequences which are mentioned herein is calculated from the BLAST results performed either at the NCBI (http://blast.ncbi.nlm.nih.gov/Blast.cgi) or at the GRYC (http://gryc.inra.fr/) websites using the BlastP program with the default BLOSUM62 parameters as described in Altschul et al. (1997).

By "ABC-triosyl" is meant an ABC rhamnotriosyl, i.e. an ABC triose group.

FIGURES

FIG. 1A presents the HSQC spectrum corresponding to pentasaccharide 1.

Figure 1B:
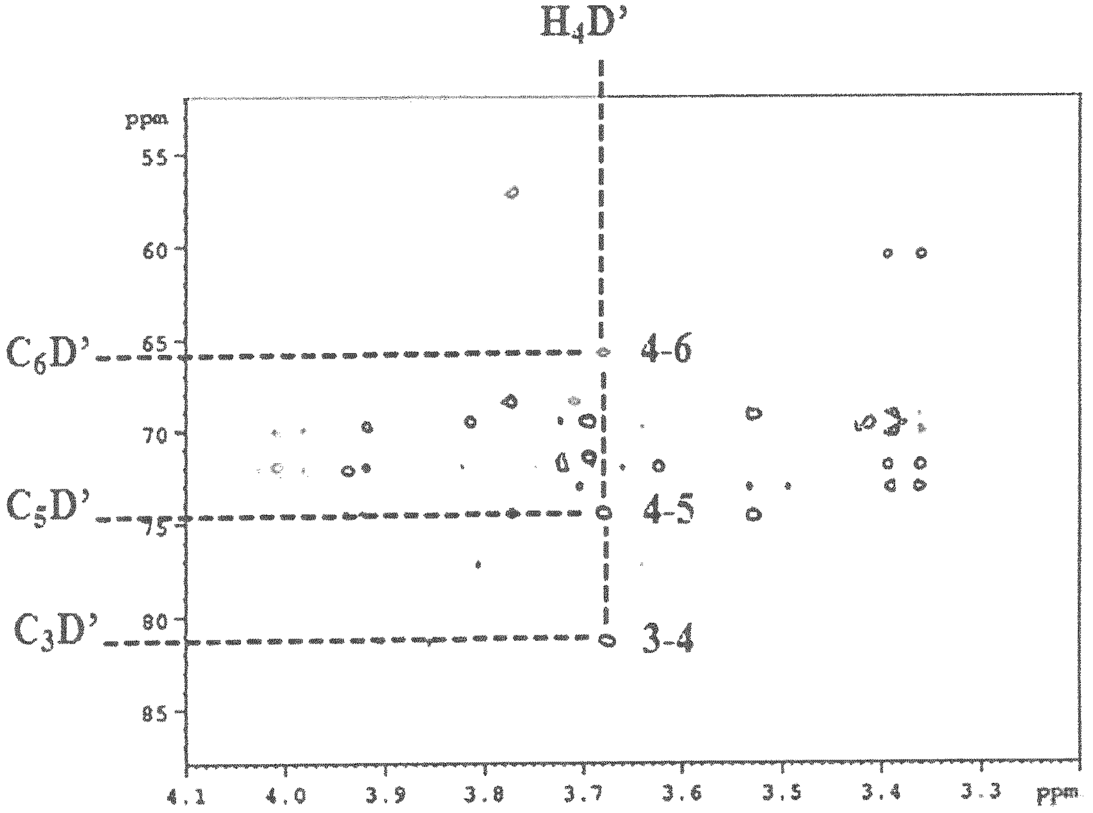

FIG. 1B presents the HMBC spectrum corresponding to pentasaccharide 1.

Figure 2:
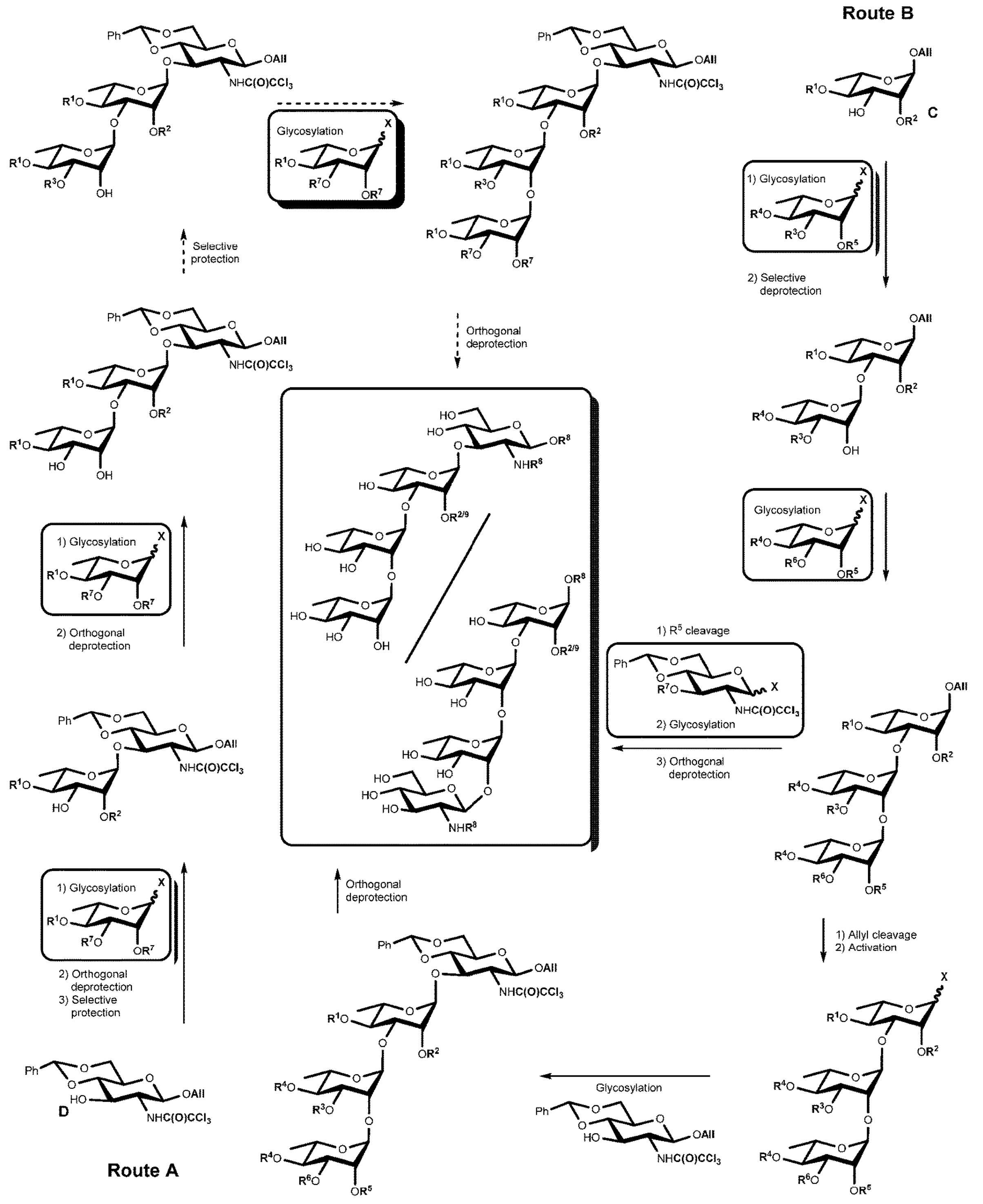

FIG. 2 depicts an overview scheme.

EXAMPLES

Example 1: Synthesis of Compound of Formula (I)

Synthesis of a Common Precursor (1) to Residues A, B and C

Allyl 4-O-(2-naphtylmethyl)-α-L-rhamnopyranoside (1)

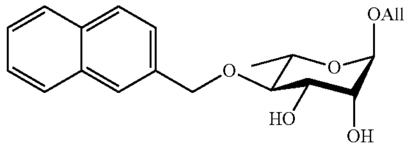

1

Acetyl chloride (50 mL, 0.70 mol, 2.5 equiv.) was added dropwise to allyl alcohol (610 mL) at 0° C., the solution was stirred for 25 min, then L-rhamnose monohydrate (50 g, 277 mmol) was added. The mixture was heated for 2.5 h at 70° C. then for 15 h at 40° C. Follow up by TLC (DCM/MeOH 8:2) indicated the total conversion of the starting hemiacetal (Rf 0.2) into a less polar product (Rf 0.7). The bath temperature was cooled to 0° C. and the solution was neutralized by addition of $NaHCO_3$ (102.5 g). The suspension was filtered over a pad of Celite® and solvents were evaporated and co-evaporated three times with toluene.

The brown oily residue was dissolved in anhydrous acetone (300 mL), then 2,2-dimethoxypropane (100 mL, 0.81 mol, 3.0 equiv.) and PTSA (3.04 g, 16 mmol, 0.05 equiv.) were successively added. The mixture was stirred for 3 h at rt. Follow up by TLC (DCM/MeOH 9:1) indicated the total conversion of the intermediate allyl glycoside (Rf 0.3) into a less polar product (Rf 0.6). The solution was neutralized by adding $Et_3N$ (4 mL), solvents were evaporated under reduced pressure. The residue was dissolved in DCM (600 mL) and washed with $H_2O$ (3×300 mL) and brine (200 mL). The organic layer was dried by passing through phase separator filter and concentrated to dryness.

The residue was dissolved in DMF (800 mL) under Ar, the bath temperature was cooled to −5° C., and NaH (60% oil dispersion, 29.1 g, 0.73 mol, 2.4 equiv.) was added portionwise to this suspension. The mixture was stirred for 2 h at rt, then 2-bromomethylnaphthalene (73.5 g, 0.33 mol, 1.2 equiv.) was added portionwise at −5° C. and the reaction mixture was stirred at rt for 2 h. Follow up by TLC (cyclohexane/EtOAc 7:3) indicated the total conversion of the intermediate alcohol (Rf 0.3) into a less polar product (Rf 0.67). The reaction was quenched at 0° C. by addition of MeOH (50 mL). Solvents were eliminated under reduced pressure and volatiles were co-evaporated with toluene. The residue was taken up in EtOAc (400 mL) and washed with $H_2O$ (3×300 mL) and brine (150 mL). The organic phase was dried over anhydrous $Na_2SO_4$, filtered, and concentrated to dryness.

The residue was dissolved in 80% aq. AcOH (500 mL) and the solution was stirred for 6 h at 80° C. then over the weekend at rt and heating was continued for 5 h at 80° C. Follow up by TLC (cyclohexane/EtOAc 5:5) indicated the total conversion of the intermediate acetal (Rf 1.0) into a more polar product (Rf 0.2). Solvents were removed under vacuum and traces of AcOH were eliminated by co-evaporation with toluene (3×400 mL) to give a brown solid.

Filtration over a pad of silica eluting with a 4:1 mixture of cHex/EtOAc then 1:1 mixture of cyclohexane/EtOAc then recrystallization in hot cyclohexane afforded the expected diol (65.5 g, 69%) as a pale brown solid. Mother liquors were further purified by flash column chromatography (cyclohexane/EtOAc 100:0 to 50:50) to give an additional amount of expected diol (11.6 g). The total yield of diol 1 is 81% over 4 steps.

$^1$H NMR (400 MHz, $CDCl_3$) δ 7.87-7.78 (m, 4H, $H_{ArNap}$), 7.52-7.44 (m, 3H, $H_{ArNap}$), 5.89 (dddd, 1H, J=17.2, 10.4, 6.0, 5.2 Hz, $CH{=}CH_2$), 5.28 ($dq_{app}$, 1H, J=17.2, 1.5 Hz, $CH{=}CH_2$), 5.19 ($dq_{app}$, 1H, J=10.4, 1.5 Hz, $CH{=}CH_2$), 4.95-4.86 (m, 2H, $H_{ArNap}$), 4.81 (d, J=1.4 Hz, 1H, H-1), 4.17 (ddt, 1H, J=12.9, 5.1, 1.5 Hz, 1H, $H_{All}$), 4.02-3.93 (m, 3H, $H_{All}$, H-2, H-3), 3.79 (dq, 1H, J=9.2, 6.3 Hz, H-5), 3.41 ($t_{app}$, 1H, J=9.2 Hz, H-4), 2.45 (brs, 2H, OH), 1.38 (d, 3H, J=6.3 Hz, H-6).

$^{13}$C NMR (100 MHz, $CDCl_3$) δ 133.8 ($CH{=}CH_2$), 128.4 ($C_{IVAr}$), 128.0 ($C_{IVAr}$), 127.7 ($C_{IVAr}$), 126.7-125.8 (7C, $C_{Ar}$), 117.4 ($CH{=}CH_2$), 98.5 (C-1 $^1J_{C,H}$=170.1 Hz), 75.1 ($CH_{2Nap}$), 71.6, 71.3 (2C, C-2, C-3), 68.0 ($C_{All}$), 67.3 (C-5), 18.1 (C-6).

HRMS (ESI$^+$): m/z 362.1985 (calcd for $C_{16}H_{22}O_5Na$ $[M+NH_4]^+$ m/z 362.1967); m/z 367.1576 (calcd for $C_{43}H_{51}ClO_{12}Na$ $[M+Na]^+$ m/z 367.1521).

Synthesis of the Rhamnopyranosyl Donors (5 and 5a) Used as Precursor to Residues A and B

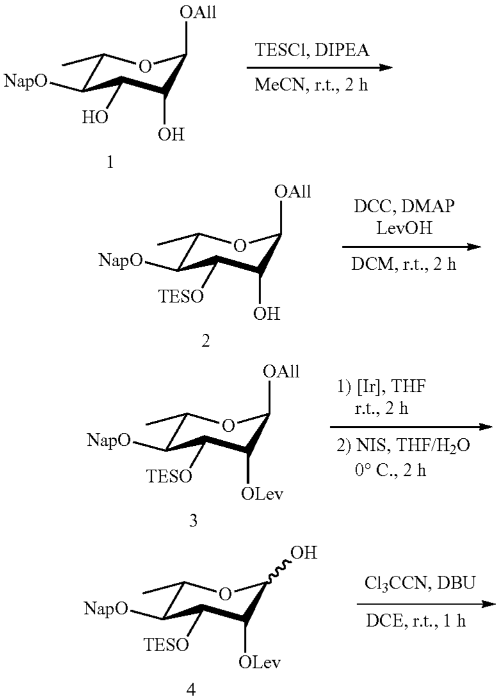

1

2

3

4

-continued

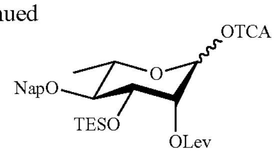

5

[Ir] = $[IrH_2(THF)_2(PPh_2Me)_2]PF_6$

The TES Derivative

Allyl 4-O-(2-naphthylmethyl)-3-O-triethylsilyl-α-L-rhamnopyranoside (2)

To a solution of allyl 4-O-(2-naphthylmethyl)-α-L-rhamnopyranoside (diol 1) (5.0 g, 14.5 mmol) in anhydrous acetonitrile (MeCN, 200 mL) stirred at 0° C. were successively added dropwise chlorotriethylsilane (TESCl 99%, 2.9 mL, 17.4 mmol, 1.2 equiv) and N,N-diisopropylethylamine (DIPEA 99.5%, 3.8 mL, 21.8 mmol, 1.5 equiv). After stirring the reaction mixture for 2 h at room temperature, TLC (cyclohexane/EtOAc 8:2) showed complete consumption of the starting material (Rf=0.13) and the presence of a main product (Rf=0.70). Methanol (1.2 mL, 29.0 mmol, 0.5 equiv) was added, the mixture was stirred for 15 min, and volatiles were evaporated under reduced pressure. Toluene was added and a precipitate appeared. The suspension was filtered and the filtrate was concentrated to dryness under vacuum. The residue was purified by chromatography eluting from a column of $Et_3N$-treated silica gel (toluene/ethyl acetate 95:5) to give compound 2 as a yellow oil (4.9 g, 74%).

Allyl 2-O-levulinyl-4-O-(2-naphthylmethyl)-3-O-triethylsilyl-α-L-rhamnopyranoside (3)

Route 1: To a solution of allyl 4-O-(2-naphthylmethyl)-3-O-triethylsilyl-α-L-rhamnopyranoside (alcohol 2) (5.0 g, 10.9 mmol) in anhydrous dichloromethane (DCM, 65 mL) stirred at room temperature were successively added 1,3-dicyclohexylcarbodiimide (DCC 99%, 7.65 g, 37.1 mmol, 3.4 equiv), 4-dimethylaminopyridine (DMAP, 1.07 g, 8.73 mmol, 0.8 equiv) and levulinic acid (LevOH 98%, 4.69 mL, 45.8 mmol, 4.2 equiv). After stirring the reaction mixture for 2 h at room temperature, TLC (cyclohexane/EtOAc 7:3) showed complete consumption of the starting material (Rf=0.60) and the presence of a more polar compound (Rf=0.53). The reaction mixture was concentrated under reduced pressure. The crude material was taken in EtOAc (50 mL) and the resulting suspension was filtered on a pad of Celite®. Water (30 mL) was added to the filtrate and the organic layer was washed successively with 10% aqueous copper (II) sulfate (30 mL), water (30 mL), saturated aqueous sodium bicarbonate (30 mL) and brine (30 mL). The organic layer was dried by stirring over anhydrous sodium sulfate, filtered and concentrated under vacuum. The residue was purified by eluting from a column of $Et_3N$-treated silica gel (cyclohexane/EtOAc 9:1 to 5:5) to give the fully protected 3 as a yellow oil (4.5 g, 74%).

Route 2: To a solution of allyl 4-O-(2-naphthylmethyl)-α-L-rhamnopyranoside (diol 1) (20.0 g, 58.1 mmol) in anhydrous MeCN (800 mL) stirred at 0° C. were successively added dropwise TESCl (11.70 mL, 69.7 mmol, 1.2 equiv) and DIPEA (15.2 mL, 87.1 mmol, 1.5 equiv). After stirring the reaction mixture for 2 h at room temperature, TLC (cyclohexane/EtOAc 8:2) showed complete consumption of the starting material (Rf=0.13) and the presence of a main product (Rf=0.70). Methanol (1.2 mL, 29.0 mmol, 0.5 equiv) was added, the mixture was stirred for 15 min, and volatiles were evaporated under reduced pressure. Toluene was added and a precipitate appeared. The suspension was filtered and the filtrate was concentrated to dryness under vacuum.

To a solution of the crude alcohol 2 in anhydrous DCM (200 mL) stirred at room temperature were successively added DCC (40.74 g, 197.4 mmol, 3.4 equiv), DMAP (5.7 g, 46.5 mmol, 0.8 equiv) and levulinic acid (23.8 mL, 232.3 mmol, 4.0 equiv). After stirring the reaction mixture for 2 h at room temperature, TLC (cyclohexane/EtOAc 7:3) showed complete consumption of the starting material (Rf=0.60) and the presence of a more polar product (Rf=0.53). The reaction mixture was concentrated under reduced pressure. The crude material was taken in EtOAc (50 mL) and the resulting suspension was filtered on a pad of Celite®. Water (30 mL) was added to the filtrate and the organic layer was washed successively with 10% aqueous copper (II) sulfate (30 mL), water (30 mL), saturated aqueous sodium bicarbonate (30 mL) and brine (30 mL). The organic layer was dried by stirring over anhydrous sodium sulfate, filtered and concentrated under vacuum. The residue was purified by eluting from a column of $Et_3N$-treated silica gel (cyclohexane/ethyl acetate 9:1 to 5:5) to give the fully protected 3 as a yellow oil with (30.7 g, 95%).

2-O-Levulinyl-4-O-(2-naphthylmethyl)-3-O-triethylsilyl-α/β-L-rhamnopyranose (4)

To a solution of allyl 2-O-levulinyl-4-O-(2-naphthylmethyl)-3-O-triethylsilyl-α-L-rhamnopyranoside (allyl glycoside 3) (2.5 g, 4.49 mmol) in anhydrous THF (60 mL) stirred at room temperature was added hydrogen-activated 1,5-cyclooctadienebis-(methyldiphenylphosphine)iridium(I) hexafluorophosphate (76.0 mg, 90 μmol, 0.02 equiv). After stirring the reaction mixture for 2 hours at room temperature, TLC (cyclohexane/EtOAc 7:3) showed complete conversion of the starting material (Rf=0.53) into a less polar product (Rf=0.56). N-Iodosuccinimide (NIS 95%, 1.21 g, 5.39 mmol, 1.2 equiv) in 1:5 water/THF (30 mL) and then distilled water (40 mL) were added to the mixture stirred at 0° C. After stirring the reaction mixture for 2 h at this temperature, TLC (cyclohexane/EtOAc 7:3) showed complete conversion of the intermediate (Rf=0.56) into a more polar product (Rf=0.26). 10% aqueous sodium metabisulfite (50 mL) was added. THF was evaporated under reduced pressure and DCM (50 mL) was added. The aqueous layer was extracted twice with DCM (30 mL) and the combined organic phases were washed with saturated aqueous sodium bicarbonate (30 mL) and then brine (30 mL). The organic layer was dried over anhydrous sodium sulfate, filtered and concentrated under vacuum. The residue was purified by chromatography eluting from a column of $Et_3N$-treated silica gel (cyclohexane/EtOAc 8:2 to 6:4) to give hemiacetal 4 as a yellow oil (2.1 g, 89%, α/β 8:2).

2-O-Levulinyl-4-O-(2-naphthylmethyl)-3-O-triethylsilyl-α/β-L-rhamnopyranosyl trichloroacetimidate (5)

Route 1: To a solution of 2-O-levulinyl-4-O-(2-naphthylmethyl)-3-O-triethylsilyl-L-rhamnopyranose (hemiacetal 4) (2.00 g, 3.87 mmol) in anhydrous 1,2-dichloroethane (DCE, 30 mL) stirred at room temperature were successively added trichloroacetonitrile ($Cl_3CCN$ 98%, 1.16 mL, 11.6 mmol, 3.0 equiv) and 1,8-diazabicyclo[5.4.0]undec-7-ene (DBU 98%, 289 μL, 1.94 mmol, 0.5 equiv). After stirring the reaction mixture for 2 h at room temperature, TLC (cyclohexane/ethyl acetate 7:3) showed complete consumption of the starting material (Rf=0.26) into a less polar product (Rf=0.53). Volatiles were evaporated under reduced pressure. The residue was purified by chromatography eluting from a column of triethylamine-treated silica gel (cyclohexane/ethyl acetate 9:1 to 5:5) to give donor 5 as a whitish crystalline solid (2.3 g, 90%, α/β 95:5).

Route 2: To a solution of allyl 2-O-levulinyl-4-O-(2-naphthylmethyl)-3-O-triethylsilyl-α-L-rhamnopyranoside (allyl glycoside 3) (15.0 g, 26.9 mmol) in anhydrous THF (300 mL) stirred at room temperature was added hydrogen-activated 1,5-cyclooctadienebis-(methyldiphenylphosphine) iridium(I)hexafluorophosphate ([Ir], 456 mg, 540 μmol, 0.02 EtOAc 7:3) showed complete conversion of the starting material (Rf=0.53) into a less polar product (Rf=0.56). NIS (7.27 g, 32.3 mmol, 1.2 equiv) in 1:5 water/THF (150 mL) and then distilled water (250 mL) were added to the mixture stirred at 0° C. After stirring the reaction mixture for 2 h at this temperature, TLC (cyclohexane/EtOAc 7:3) showed complete conversion of the intermediate (Rf=0.56) into a more polar product (Rf=0.26). 10% aqueous sodium metabisulfite (100 mL) was added. THF was evaporated under reduced pressure and DCM (500 mL) was added. The aqueous layer was extracted twice with DCM (300 mL) and the combined organic phases were washed with saturated aqueous sodium bicarbonate (200 mL) and then brine (200 mL). The organic layer was dried over anhydrous sodium sulfate, filtered and concentrated under vacuum (m: 14.3 g).

To a solution of the crude material (13.9 g) in anhydrous DCE (210 mL) stirred at room temperature were successively added $Cl_3CCN$ (8.1 mL, 80.8 mmol, 3.0 equiv) and DBU (2.01 mL, 13.5 mmol, 0.5 equiv). After stirring the reaction mixture for 2 h 50 at room temperature, TLC (cyclohexane/EtOAc 7:3) showed complete consumption of the starting material (Rf=0.26) into a less polar product (Rf=0.53). Volatiles were evaporated under reduced pressure. The residue was purified by chromatography eluting from a column of $Et_3N$-treated silica gel (cyclohexane/EtOAc 9:1 to 5:5) to give donor 5 as a whitish crystalline solid (15.04 g, 84%, α/β 95:5).

The BDA Derivative

L-rhamnose monohydrate

1. AllOH, AcCl, 70° C.

2. Butan-2,3-dione $BF_3•Et_2O$, $CH(OMe)_3$ MeOH, reflux

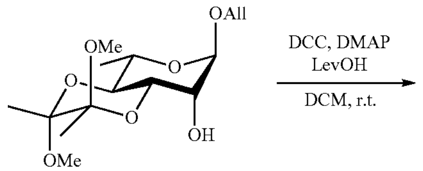

2a

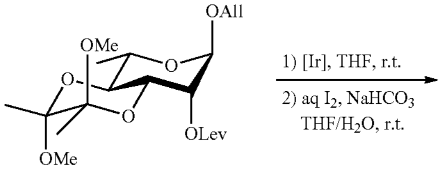

3a

-continued

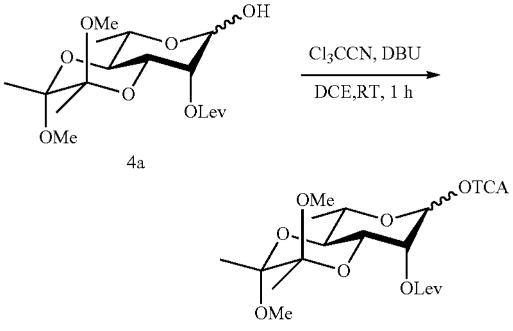

4a

5a $[Ir] = [IrH_2(THF)_2(PPh_2Me)_2]PF_6$

Allyl 3,4-O-(2',3'-dimethoxybutan-2',3'-diyl)-α-L-rhamnopyranoside (2a)

Acetyl chloride (34 mL, 475 mmol, 2.5 equiv) was added dropwise to allyl alcohol (420 mL) at 0° C. The solution was stirred for 25 min and L-rhamnose monohydrate (34.3 g, 190 mmol) was added. The mixture was heated for 2.5 h at 70° C. then for 15 h at 40° C. Follow up by TLC (DCM/MeOH 8:2) indicated the total conversion of L-rhamnose (Rf=0.2) into a less polar product (Rf 0.7). The bath temperature was cooled to 0° C. and the solution was neutralized by addition of solid $NaHCO_3$ (102.5 g). The suspension was filtered off a pad of Celite® and solvents were evaporated and co-evaporated three times with toluene.

To a solution of crude allyl rhamnoside (190 mmol) in anhydrous methanol (1.0 L) stirred at room temperature were successively added butan-2,3-dione (18.3 mL, 0.21 mol, 1.1 equiv), trimethyl orthoformate (83 mL, 0.76 mol, 4.0 equiv) and boron trifluoride etherate (11.7 mL, 95 mmol, 0.5 equiv). After stirring the reaction mixture for 1.5 h under reflux, a TLC follow up (DCM/MeOH 95:5) showed complete consumption of the starting material (Rf=0.3) and the presence of a main product (Rf=0.5). $Et_3N$ was slowly added to the reaction mixture at 0° C. until neutralization and volatiles were evaporated under reduced pressure. The residue was purified by chromatography eluting from a column of silica gel (cyclohexane/EtOAc 8:2 to 6:4) to give compound 2a as a brown oil (57.8 g, 96%, 2 isomers 9:1).

Allyl 2-O-levulinyl-3,4-O-(2',3'-dimethoxybutan-2',3'-diyl)-α-L-rhamnopyranoside (3a)

To a solution alcohol 2a (27.0 g, 84.8 mmol) in anhydrous dichloromethane (650 mL) stirred at rt were successively added DCC (59.5 g, 0.29 mol, 3.4 equiv.), DMAP (8.29 g, 67.9 mmol, 0.8 equiv.) and levulinic acid (36.5 mL, 0.36 mol, 4.2 equiv.). After stirring the reaction mixture at rt for 2 h, a TLC follow up (DCM/MeOH 98:2) showed complete consumption of the starting material (Rf=0.25) and the presence of two less polar compounds (Rf=0.6, 0.65). The reaction mixture was concentrated under reduced pressure. Saturated aqueous $NaHCO_3$ (300 mL) was added to the reaction mixture. The aqueous layer was extracted once with DCM (300 mL) and the combine organic phases were washed twice with brine (150 mL). The organic layer was dried by stirring over anhydrous sodium sulfate, filtered and concentrated under vacuum. The residue was purified by chromatography eluting from a column of silica gel (DCM/MeOH 1:0 to 9:1) to give the fully protected 3a as a brown oil (37.5 g, 95%, 2 isomers 9:1).

2-O-Levulinyl-3,4-O-(2',3'-dimethoxybutan-2',3'-diyl)-α-L-rhamnopyranosyl trichloroacetimidate (5a)

To a solution of rhamnoside 3a (37.5 g, 90.0 mmol) in anhyd. tetrahydrofuran (THF, 500 mL) stirred at rt was added hydrogen-activated 1,5-cyclooctadienebis(methyldiphenylphosphine)iridium(I) hexafluorophosphate (1.5 g, 1.80 mmol, 0.02 equiv.). After stirring the reaction mixture at room temperature for 2 h, TLC (cyclohexane/EtOAc 5:5) showed complete conversion of the starting material (Rf=0.8, 0.85) into two closely eluting products (Rf=0.8, 0.9). N-iodosuccinimide (NIS, 24.3 g, 108 mmol, 1.2 equiv.) in water/THF (1:5, 250 mL) and then additional water (370 mL) were added to the mixture stirred at 0° C. After stirring the reaction mixture for 2 h at this temperature, TLC (cyclohexane/EtOAc 5:5) showed complete conversion of the intermediate into two more polar products (Rf=0.45, 0.5). Saturated aqueous sodium metabisulfite (500 mL) and then ethyl acetate (500 mL) were added. The aq. layer was extracted twice with ethyl acetate (300 mL) and the combined organic phases were washed with saturated aqueous $NaHCO_3$ (300 mL) and then brine (300 mL). The organic layer was dried over anhyd. sodium sulfate, filtered and concentrated under vacuum.

To a solution of crude hemiacetal 4a (90.0 mmol) in anhydrous DCE (500 mL) stirred at rt were successively added trichloroacetonitrile (27.1 mL, 0.27 mol, 3.0 equiv.) and DCC (6.7 mL, 45.0 mmol, 0.5 equiv.). After stirring the reaction mixture for 2.5 h at room temperature, TLC (cyclohexane/EtOAc 7:3) showed complete consumption of the starting material (Rf=0.45, 0.5) into two less polar product (Rf=0.75, 0.5). Volatiles were evaporated under reduced pressure. The residue was purified by chromatography eluting from a column of $Et_3N$-treated silica gel (cyclohexane/EtOAc 8:2 to 6:4) to give donor 5a as a yellow to brownish oil (38.6 g, 82%, a only, 2 isomers 9:1).

Synthesis of the Glucosamine D Acceptor

The known glucosamine D acceptor was obtained following the procedure below, through route A or the improved route B (*Carbohydrate Chemistry: Proven Synthetic Methods*, Eds P. Murphy and C. Vogel, 2017, vol. 4, chap. 39, in press).

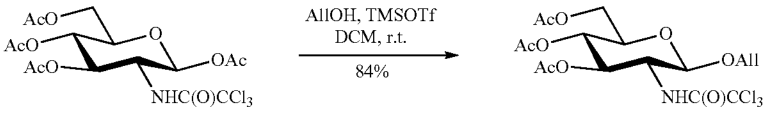

7

8

Route A

-continued

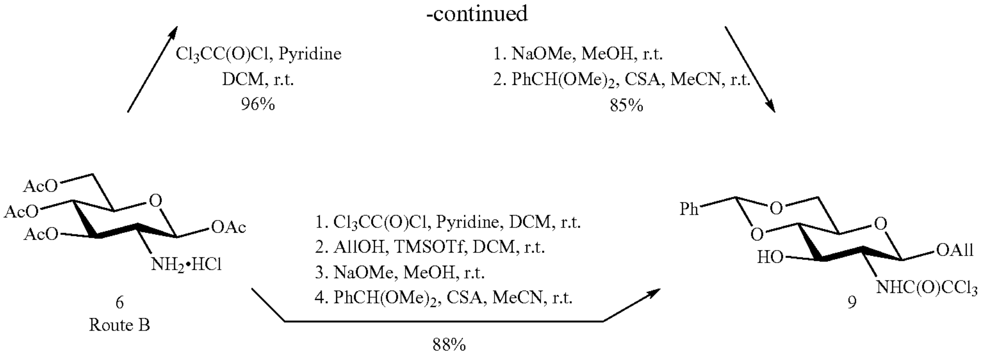

6
Route B
9

Synthesis of the Glucosamine D Donor.

The known glucosamine D donor 12 was obtained as published (*Tetrahedron Lett.* (2008) 49, 5339-42). Alternatively, the analogue of donor 12, equipped with a 4,6-O-benzylidene acetal instead of a 4,6-O-isopropylidene acetal could be obtained from the D acceptor 9 according to the procedure described for the conversion of alcohol 10 into donor 12.

It is noteworthy that alcohol 10 can also serve as a suitable acceptor in the synthesis of compounds of the formula (Ia).

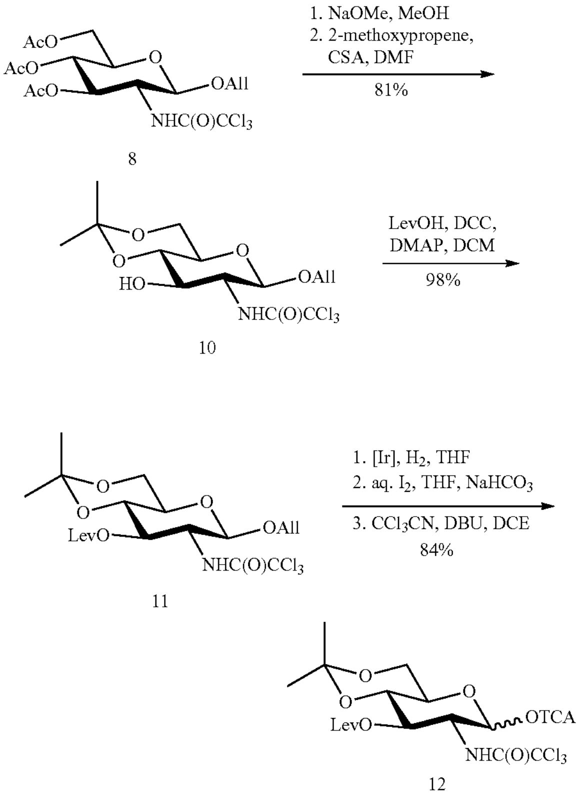

8
10
11
12

$[Ir] = [Ir(COD)_2(PPh_2Me)_2]PF_6$

A synthesis of donor 12a, which encompasses a 4,6-O-benzylidene acetal and a TBS ether in place of the 4,6-O-isopropylidene acetal and the Lev group, respectively, is exemplified in the following.

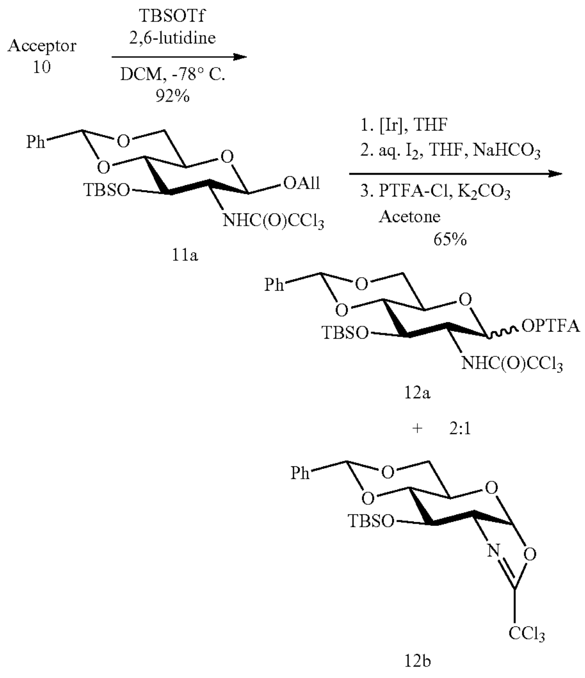

11a
12a
12b $[Ir] = [IrH_2(THF)_2(PPh_2Me)_2]PF_6$

Allyl 4,6-O-benzylidene-3-O-tert-butyldimethylsilyl-2-deoxy-2-trichloroacetamido-β-D-glucopyranoside (11a)

To a solution of allyl 4,6-O-benzylidene-2-deoxy-2-trichloroacetamido-3-D-glucopyranoside (10) (2.0 g, 4.42 mmol) in anhydrous dichloromethane (40 mL), stirred at −78° C., were successively added 2,6-lutidine (2.06 mL, 17.7 mmol, 4.0 equiv) and tert-butyldimethylsilyl trifluoromethanesulfonate (2.54 mL, 11.05 mmol, 2.5 equiv). After stirring the reaction mixture overnight at room temperature, a TLC follow up (toluene/ethyl acetate 8:2) showed complete consumption of the starting material (Rf=0.25) and the presence of a less polar product (Rf=0.7). Distilled water (50 mL) and ethyl acetate (200 mL) were added. The aqueous layer was extracted with ethyl acetate (100 mL) and the combined organic phases were washed with water (50 mL), 10% aq. citric acid (50 mL) and then water (50 mL). The organic layer was dried over anhydrous sodium sulfate, filtered and concentrated under vacuum. The residue was purified by chromatography eluting from a column of silica gel (toluene/ethyl acetate 95:5 to 9:1) to give the fully protected 11a as a white powder (2.32 g, 92%).

4,6-O-Benzylidene-3-O-tert-butyldimethylsilyl-2-deoxy-2-trichloroacetamido-a/β-D-glucopyranosyl N-(phenyl)trifluoroacetimidate (12a)

To a solution of glucosaminide 11a (2.27 g, 4.0 mmol) in anhydrous THF (200 mL) stirred at room temperature was added hydrogen-activated 1,5-cyclooctadienebis(methyldiphenylphosphine)iridium(I)hexafluorophosphate (170 mg, 0.20 mmol, 0.05 equiv). After stirring the reaction mixture for 4 hours at room temperature, a TLC follow up (toluene/ethyl acetate 9:1) showed complete conversion of the starting material (Rf=0.6) into a less polar product (Rf=0.6). N-Iodosuccinimide (1.35 g, 6.0 mmol, 1.5 equiv) in 1:5 water/THF (56 mL) was then added to the mixture stirred at room temperature. After stirring for 2 h at this temperature, a TLC follow up (toluene/EtOAc 9:1) showed complete conversion of the intermediate into a more polar product (Rf=0.2). Saturated aqueous sodium metabisulfite (200 mL) and then ethyl acetate (500 mL) were added. The aqueous layer was extracted twice with ethyl acetate (250 mL) and the combined organic phases were washed with saturated aqueous $NaHCO_3$ (200 mL) and then brine (200 mL). The organic layer was dried over anhydrous sodium sulfate, filtered and concentrated under vacuum.

To a solution of crude hemiacetal (4.42 mmol) in anhydrous acetone (36 mL), stirred at room temperature, were successively added N-(phenyl)trifluoroacetimidoyl chloride (1.80 mL, 6.63 mmol, 1.5 equiv) and potassium carbonate (1.53 g, 11.05 mmol, 2.5 equiv). After stirring the reaction mixture for 3 hours at room temperature, TLC (toluene/EtOAc 8:2) showed complete consumption of the starting material (Rf=0.2) and the presence of a mixture of less polar products (Rf=0.75 and 0.8). The mixture was filtered off a pad of Celite® and the filtrate was concentrated under reduced pressure. The residue was purified by chromatography eluting from a column of silica gel (toluene/EtOAc 95:5 to 9:1) to give a 2:1 mixture of the N-(phenyl)trifluoroacetimidate donor 12a and oxazoline 12b as a brown oil (2.57 g, 65% over two steps).

Synthesis of the $AB_{ClAc}C$—Z'

Selected Examples

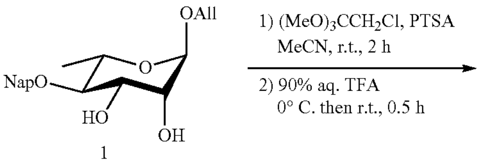

1

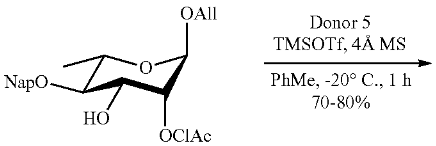

13

-continued

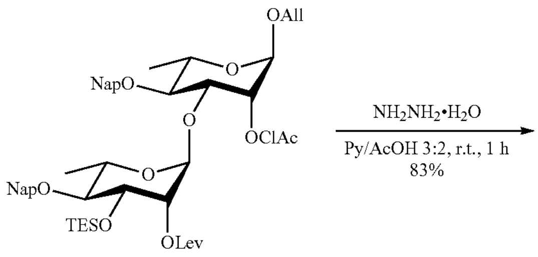

14

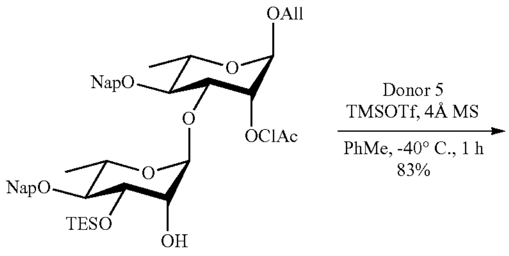

15

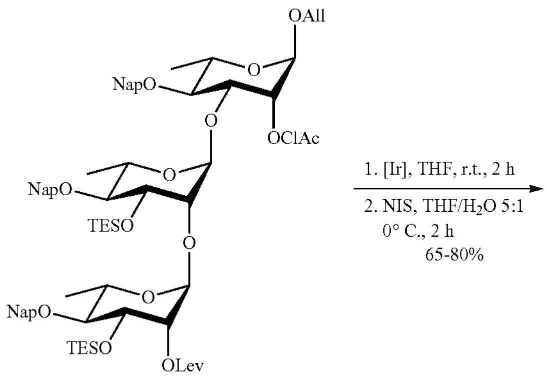

16

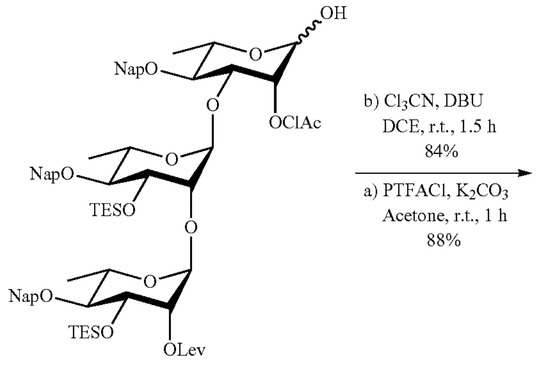

17

-continued

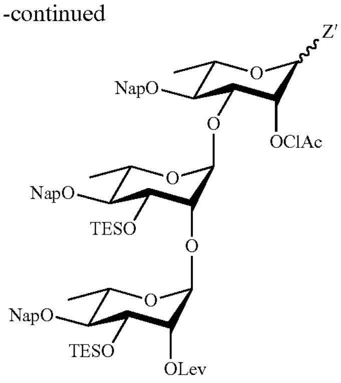

18 Z' = OTCA, route b
19 Z' = OPTFA, route a

[Ir] = $[IrH_2(THF)_2(PPh_2Me)_2]PF_6$

Allyl 2-O-chloroacetyl-4-O-(2-naphtylmethyl)-α-L-rhamnopyranoside (13)

Diol 1 (2.0 g, 6.0 mmol) was solubilized in anhydrous MeCN (5.0 mL). To the solution was added trimethylchloroorthoacetate (2.35 mL, 3.0 equiv) and PTSA (90 mg, 0.08 equiv). The solution was stirred at room temperature for 1 hour (reaction followed by TLC Toluene/EtOAc 7:3). To the reaction medium cooled to 0° C. was added a 90% aqueous TFA (3.0 mL) and the reaction mixture was stirred at room temperature for 15 min. Water (20 mL) was added. The product was extracted with DCM (2×40 mL). The organic phase was washed with saturated aqueous $NaHCO_3$ (2×25 mL) and brine (25 mL). The aqueous phase was extracted with DCM (2×25 mL). The combined organic phases were dried over $Na_2SO_4$, filtered, evaporated and finally co-evaporated with toluene to yield the crude alcohol 13 as a 92:8 mixture of regioisomers.

Allyl 2-O-levulinyl-4-O-(2-naphtylmethyl)-3-O-triethylsilyl-α-L-rhamnopyranosyl-(1→3)-2-O-chloroacetyl-4-O-(2-naphtylmethyl)-α-L-rhamnopyranoside (14)

A solution of trichloroacetimidate 5 (5.84 g, 8.83 mmol) and crude acceptor 13 (4.09 g, 1.1 equiv) in toluene (88 mL) containing 4 Å-MS (1.25 g) was stirred at room temperature for 15 min, then at −60° C. for 15 min. tert-Butyldimethylsilyl trifluoromethanesulfonate (TBSOTf, 100 μL, 0.05 equiv) was added to reaction mixture stirred at −60° C. and the bath was left to reach −40° C. After stirring for 1 h, $Et_3N$ was added to the suspension at −35° C., the mixture was filtered through a pad of Celite®, and the filtrate was concentrated to dryness. Rapid filtration of the residue over silica gel and crystallization in EtOAc/pentane 5:1 (400 mL) gave the fully protected 14 (3.83 g, 72%).

Allyl 2-O-levulinyl-4-O-(2-naphtylmethyl)-3-O-triethylsilyl-α-L-rhamnopyranosyl-(1→2)-4-O-(2-naphtylmethyl)-3-O-triethylsilyl-α-L-rhamnopyranosyl-(1→3)-2-O-chloroacetyl-4-O-(2-naphtylmethyl)-α-L-rhamnopyranoside (16)

A solution of trichloroacetimidate 5 (1.04 g, 1.24 equiv) and alcohol 15 (1.0 g, 1.22 mmol) in toluene (30 mL) containing 4 Å-MS (1.38 g) was stirred at room temperature for 15 min, then at −20° C. for 15 min. TMSOTf (11 μL, 0.05 equiv) was added to reaction mixture stirred at −20° C. and the bath was left to reach −10° C. After stirring for 1 h at this temperature, stirring is pursued for 1 h while the bath slowly reached room temperature. $Et_3N$ was added to the suspension, the mixture was filtered through a pad of Celite®, and the filtrate was concentrated to dryness. Column chromatography gave the fully protected $AB_{ClAc}C$ trisaccharide 16 (1.36 g, 85%).

HRMS (ESI+): m/z 1336.6191 (calcd for $C_{73}H_{99}Cl_4NO_{16}Si_2$ $[M+NH_4]^+$) found m/z 1336.6171.

2-O-Levulinyl-4-O-(2-naphtylmethyl)-3-O-triethylsilyl-α-L-rhamnopyranosyl-(1→2)-4-O-(2-naphtylmethyl)-3-O-triethylsilyl-α-L-rhamnopyranosyl-(1→3)-2-O-chloroacetyl-4-O-(2-naphtylmethyl)-α/β-L-rhamnopyranose (17)

To a solution of the fully protected $AB_{ClAc}C$ (1.04 g, 7.6 mmol) in anhydrous THF (35 mL) stirred at room temperature was added hydrogen-activated [Ir] (13.0 mg, 0.02 equiv). After stirring the reaction mixture for 45 min at room temperature, TLC (toluene/EtOAc 9:1) showed complete conversion of the starting material into a less polar product. The reaction mixture was cooled to 0° C., NIS (205 mg, 1.2 equiv) in 1:5 water/THF (17.5 mL) and then distilled water (25 mL) were added to the mixture stirred at 0° C. After stirring the reaction mixture for 1.5 h at this temperature, TLC (toluene/ethyl acetate 9:1) showed complete conversion of the intermediate into a more polar product. 10% aqueous sodium metabisulfite (50 mL) was added. THF was evaporated under reduced pressure and DCM (100 mL) was added. The aqueous layer was extracted twice with DCM (50 mL) and the combined organic phases were washed with saturated aqueous sodium bicarbonate (50 mL) and then brine (50 mL). The organic layer was dried over anhydrous sodium sulfate, filtered and concentrated under vacuum. The residue was purified by chromatography eluting from a column of $Et_3N$-treated silica gel (toluene/ethyl acetate 85:15 to 0:100) to give hemiacetal 17 (825 mg, 85%).

HRMS (ESI+): m/z 1296.5878 (calcd for $C_{70}H_{95}Cl_4NO_{16}Si_2$ $[M+NH_4]^+$) found m/z 1296.5922.

2-O-Levulinyl-4-O-(2-naphtylmethyl)-3-O-triethylsilyl-α-L-rhamnopyranosyl-(1→2)-4-O-(2-naphtylmethyl)-3-O-triethylsilyl-α-L-rhamnopyranosyl-(1→3)-2-O-chloroacetyl-4-O-(2-naphtylmethyl)-α/β-L-rhamnopyranosyl trichloroacetimidate (18)

To a solution of the $AB_{ClAc}C$ triose 17 (700 mg, 550 μmol) in anhydrous DCE (5.0 mL) stirred at room temperature were successively added $Cl_3CCN$ (165 μL, 3.0 equiv) and DBU (40 μL, 0.5 equiv). After stirring the reaction mixture for 45 min at room temperature, the same amounts of $CCl_3CN$ and DBU were added and the reaction was stirred for 1 h more at room temperature. Volatiles were evaporated under reduced pressure. The residue was purified by chromatography eluting from a column of $Et_3N$-treated silica gel (toluene/EtOAc 8:2 containing 3% $Et_3N$) to give donor 18 (830 mg, 84%).

HRMS (ESI+): m/z 1439.4974 (calcd for $C_{72}H_{95}Cl_4N_2O_{16}Si_2$ $[M+NH_4]^+$) found m/z 1439.4912.

2-O-Levulinyl-4-O-(2-naphtylmethyl)-3-O-triethylsilyl-α-L-rhamnopyranosyl-(1→2)-4-O-(2-naphtylmethyl)-3-O-triethylsilyl-α-L-rhamnopyranosyl-(1→3)-2-O-chloroacetyl-4-O-(2-naphtylmethyl)-α/β-L-rhamnopyranosyl N-phenyltrifluoroacetimidate (19)

To a solution of the $AB_{ClAc}C$ triose 17 (1.56 g, 1.22 mmol) in acetone (24.4 mL) stirred at room temperature were successively added $K_2CO_3$ (337 mL, 2.0 equiv) and N-phenyltrifluoroacetimidoyl chloride (PTFACl, 290 μL, 1.5 equiv). After stirring the reaction mixture overnight at room temperature, a TLC (cyclohexane/EtOAc 2:8) indicated that that the starting 17 had been converted to a less polar product. The suspension was filtered over a pad of Celite® and volatiles were evaporated under reduced pressure. The residue was purified by column chromatography to give donor 19 (1.56 g, 88%).

$AB_{ClAc}C_{Cl3Ac}D$-All may also be obtained through the alternative route B as defined below, whereby the protecting group differs from that shown above and are: $R^1$=Nap, $R^3$, $R^4$=$R^6$, $R^4$=BDA, $R^2$=ClAc, $R^5$=Lev, $R^8$=All, $R^9$=Cl3Ac).

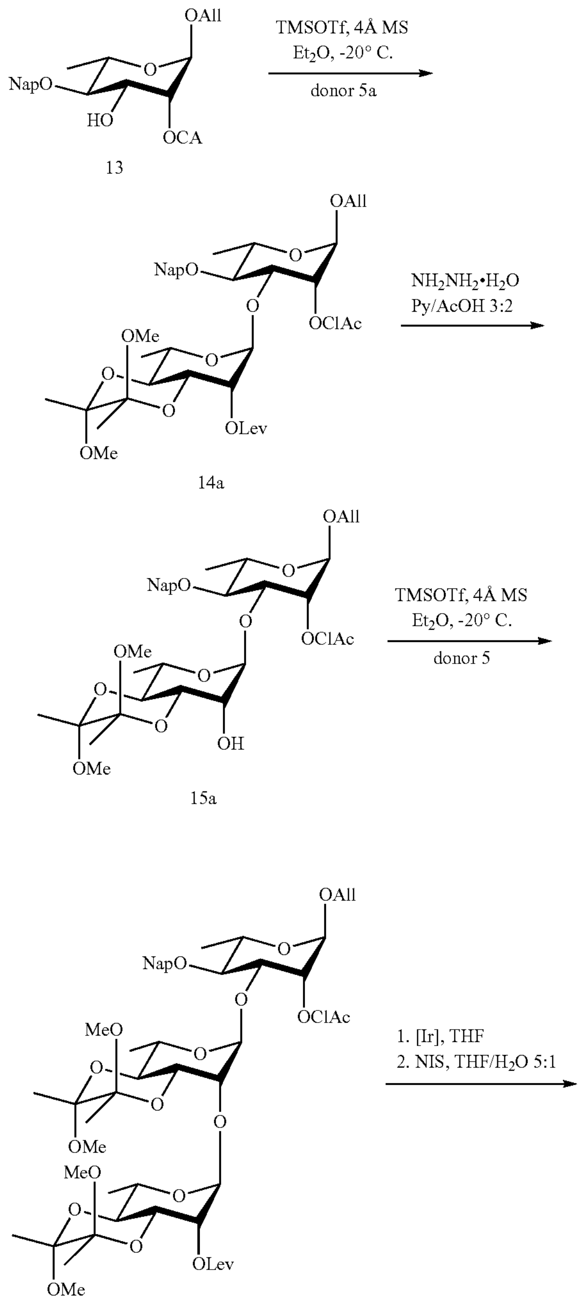

13

14a

15a

16a

-continued

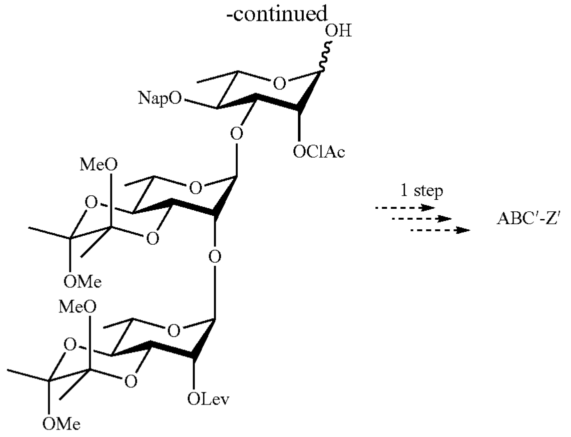

17a

[Ir] = $[IrH_2(THF)_2(PPh_2Me)_2]PF_6$

SELECTED EXAMPLES

Allyl 2-O-levulinyl-3,4-O-(2',3'-dimethoxybutan-2',3'-diyl)-α-L-rhamnopyranosyl-(1→3)-2-O-chloroacetyl-4-O-(2-naphtylmethyl)-α-L-rhamnopyranoside (14a)

To a solution of crude allyl 2-O-chloroacetyl-4-O-(2-methylnaphthyl)-α-L-rhamnopyranoside (5, 6.91 mmol, 1.2 equiv.) in anhyd. diethyl ether (60 mL), stirred at rt, were successively added donor 5a (3.0 g, 5.76 mmol) and activated 4 Å molecular sieves (3.0 g). After stirring for 15 min at rt, the reaction mixture was cooled down to −20° C. and stirred for an additional 15 min at this temperature. Trimethylsilyl trifluoromethanesulfonate (TMSOTf, 0.18 mL, 1.15 mmol, 0.2 equiv.) was then slowly added. After stirring the reaction mixture for 1 h at −20° C., TLC (toluene/ethyl acetate 7:3) showed complete consumption of the donor 5a (Rf=0.4) and the presence of a less polar product (Rf=0.6). Triethylamine was then added until neutralization. The reaction mixture was stirred for 15 min at −20° C. and then filtered off a pad of Celite®. The filtrate was concentrated under reduced pressure. The residue was purified by chromatography eluting from a column of silica gel (cyclohexane/ethyl acetate 97:3 to 7:3) to give disaccharide 14a as a yellow oil (3.1 g, 69%).

Allyl 3,4-O-(2',3'-dimethoxybutan-2',3'-diyl)-α-L-rhamnopyranosyl-(143)-2-O-chloroacetyl-4-O-(2-naphtylmethyl)-α-L-rhamnopyranoside (15a)

To a solution of disaccharide 14a (1.0 g, 1.28 mmol) in pyridine/acetic acid (3:2, 13 mL), stirred at room temperature, was added hydrazine monohydrate (125 μL, 2.57 mmol, 2.0 equiv.). After stirring the reaction mixture at room temperature for 1 h, a TLC follow up (toluene/ethyl acetate 7:3) showed complete consumption of the starting material (Rf=0.6) and the presence of a closely eluting product (Rf=0.6). Saturated aqueous $NaHCO_3$ (15 mL) was added and the aqueous layer was extracted twice with dichloromethane (15 mL) and the combine organic phases were washed once with brine (15 mL). The organic layer was dried over anhydrous sodium sulfate, filtered and concentrated under vacuum. The residue was purified by chromatography eluting from a column of silica gel (toluene/ethyl acetate 9:1 to 7:3) to give disaccharide 15a as a yellow oil (0.63 g, 72%).

Allyl 3,4-O-(2',3'-dimethoxybutan-2',3'-diyl)-2-O-levulinyl-α-L-rhamnopyranosyl-(1→2)-3,4-O-(2',3'-dimethoxybutan-2',3'-diyl)-α-L-rhamnopyranosyl-(1→3)-2-O-chloroacetyl-4-O-(2-naphtylmethyl)-α-L-rhamnopyranoside (16a)

To a solution of alcohol 15a (300 mg, 0.44 mmol) in anhyd. diethyl ether (4.0 mL), stirred at rt, were successively added donor 5 (252 mg, 0.48 mmol, 1.1 equiv.) and activated 4 Å MS (0.3 g). After stirring the reaction mixture for 15 min at rt, the reaction mixture was cooled down to −20° C. and stirred for an additional 15 min at this temperature. Trimethylsilyl trifluoromethanesulfonate (6.8 μL, 44 μmol, 0.1 equiv.) was then slowly added. After stirring the reaction mixture for 2 h at −20° C., TLC (toluene/diethyl ether/ethyl acetate 5:4:1) showed complete consumption of disaccharide 7 (Rf=0.65) and the presence of a less polar product (Rf=0.7). Triethylamine was then added until neutralization. The reaction mixture was stirred for 15 minutes at −20° C. and then filtered off a pad of Celite®. The filtrate was concentrated under reduced pressure. The residue was purified by chromatography eluting from a column of silica gel (toluene/ethyl acetate 9:1 to 7:3) to give trisaccharide 16a as a yellow to brown oil (370 mg, 81%).

Synthesis of $AB_{ClAc}C_{Cl3Ac}D$-All $AB_{ClAc}C_{Cl3Ac}D$-All (ABC'D', 21) was obtained following the generic route B (the first steps of route B up to the triosyl donor 18 being in particular described above) as defined below. The activation glycosylation and a final two-step orthogonal deprotection of route B are in particular performed with a rhamnotriosyl donor and a monosaccharide D acceptor 9 as shown in the more detailed scheme, which just follows. In the exemplified synthesis ($R^1$=$R^4$=Nap, $R^3$=$R^6$=TES, $R^2$=ClAc, $R^5$=Lev, $R^8$=All, $R^9$=Cl3Ac).

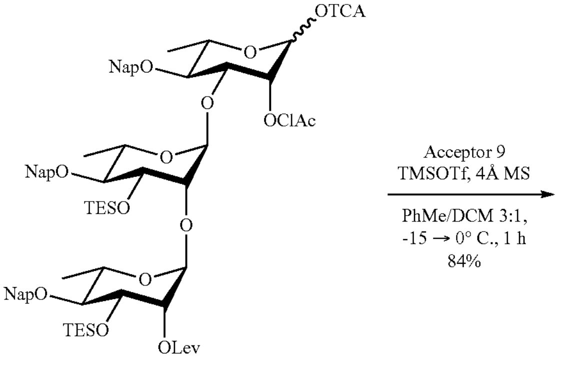

18

-continued

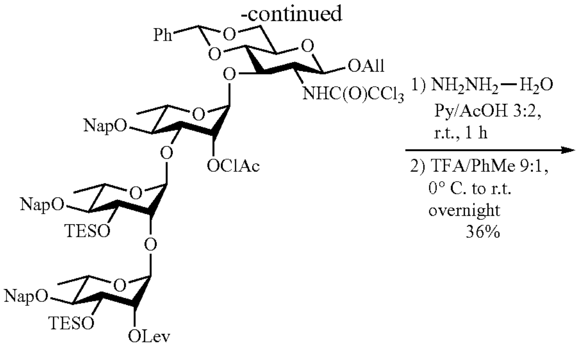

20

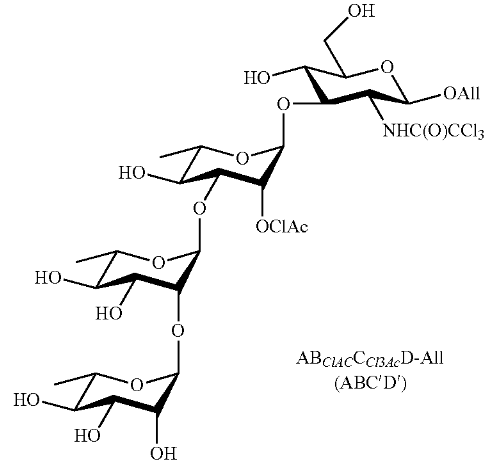

$AB_{ClAc}C_{Cl3Ac}D$-All
(ABC'D')

21

$AB_{ClAc}C_{Cl3Ac}D$-All may also be obtained through the alternative route A as defined in the overview scheme below.

$AB_{ClAc}C_{Cl3Ac}D$-All may also be obtained through the alternative route B as defined below, whereby the protecting group differ from that shown above and are: $R^1$=PMB, $R^3$=$R^4$=Nap, $R^6$=TES, $R^2$=ClAc, $R^5$=Lev, $R^8$=All, $R^9$=Cl3Ac).

SELECTED EXAMPLES

Allyl 2-O-levulinyl-4-O-(2-naphtylmethyl)-3-O-triethylsilyl-α-L-rhamnopyranosyl-(1→2)-4-O-(2-naphtylmethyl)-3-O-triethylsilyl-α-L-rhamnopyranosyl-(1→3)-2-O-chloroacetyl-4-O-(2-naphtylmethyl)-α-L-rhamnopyranosyl-(1→3)-4,6-O-benzylidene-2-deoxy-2-N-trichloroacetyl-β-D-glucopyranoside (20)

A solution of the triosyl trichloroacetimidate 18 (924 mg, 649 μmol) and the D acceptor 9 (440 mg, 1.5 equiv) in toluene/DCM (3:1, 37 mL) containing 4 Å-MS (1.91 g) was stirred at room temperature for 15 min, then at −15° C. for 15 min. TBSOTf (22 μL, 0.15 equiv) was added to reaction mixture stirred at −15° C. and the bath was left to reach −0° C. in 1.3 h. A follow up by TLC (toluene/EtOAc 9:1) indicated consumption of the donor. $Et_3N$ was added to the suspension, the mixture was filtered through a pad of Celite®, and the filtrate was concentrated to dryness. Column chromatography gave the fully protected $AB_{ClAc}C_{Cl3Ac}D$ tetrasaccharide (20, 932 mg, 84%).

HRMS (ESI+): m/z 1729.6128 (calcd for $C_{88}H_{113}Cl_4N_2O_{21}Si_2$ $[M+NH_4]^+$) found m/z 1729.6161.

Allyl α-L-rhamnopyranosyl-(1→2)-α-L-rhamnopyranosyl-(1→3)-2-O-chloroacetyl-α-L-rhamnopyranosyl-(1→3)-2-deoxy-2-N-trichloroacetyl-β-D-glucopyranoside (21)

To a solution of the alcohol (222 mg, 137 μmol)—issued from the delevulinylation of the fully protected 20—in toluene stirred at 0° C. was added TFA to reach a TFA/toluene ratio of 9:1. The reaction mixture was stirred overnight, at which point a follow up by TLC indicated total consumption of the starting tetrasaccharide and the presence of a major more polar product. Volatiles were coevaporated twice with toluene, then once with acetonitrile and finally with MeOH. The crude material was purified by reverse phase flash chromatography ($H_2O$/MeCN 0→50%), then by RP-HPLC (MeCN/$H_2O$ 20.5%) to give the target $AB_{ClAc}C_{Cl3A}CD$-All 21 following freeze-drying (70 mg, 36%). RP-HPLC (C18® RP fusion (4.6×250 mm, 4.0 μm, 80 Å, $CH_3CN$ in $H_2O$ (30% for 4 min, then 30→40% over 7 min, at 1.0 mL·min$^{-1}$), 40° C., λ: 220 nm)=7.6 min.

$^1H$ NMR (800 MHz, $D_2O$), δ 5.84 (m, 1H, —CH═), 5.25 (m, 1H, $J_{trans}$=17.3 Hz, ═$CH_2$), 5.19 (m, 1H, $J_{cis}$=10.5 Hz, ═$CH_2$), 5.13 (dd, 1H, $J_{2,3}$=3.0 Hz, $J_{2,1}$=1.9 Hz, H-$2_C$), 5.11 (d, 1H, $J_{1,2}$=1.3 Hz, H-$1_B$), 4.86 (d, 1H, $J_{1,2}$=1.6 Hz, H-$1_C$), 4.86 (d, 1H, $J_{1,2}$=1.5 Hz, H-$1_A$), 4.66 (d, 1H, $J_{1,2}$=8.0 Hz, H-$1_D$), 4.28 (m, 1H, $H_{All}$), 4.27 (d, 1H, $J_{gem}$=15.4 Hz, $H_{ClAc}$), 4.23 (d, 1H, $J_{gem}$=15.4 Hz, $H_{ClAc}$), 4.12 (m, 1H, $H_{All}$), 4.05 (m, 1H, H-$5_C$), 3.99 (dd, 1H, $J_{2,3}$=3.3 Hz, $J_{2,1}$=1.7 Hz, H-$2_A$), 3.93 (dd, 1H, $J_{3,4}$=9.7 Hz, $J_{3,2}$=3.1 Hz, H-$3_C$), 3.89 (dd, 1H, $J_{2,3}$=4.7 Hz, $J_{2,1}$=1.7 Hz, H-$2_B$), 3.88 (d, 1H, $J_{6,5}$=2.1 Hz, H-$6b_D$), 3.86 (m, 1H, H-$2_D$), 3.72 (m, 2H, H-$3_D$, H-$3_A$), 3.71 (d, 1H, $J_{6,5}$=3.3 Hz, H-$6a_D$), 3.69 (m, 1H, H-$5_B$), 3.63 (dd, 1H, $J_{3,4}$=9.9 Hz, $J_{3,2}$=3.5 Hz, H-$3_B$), 3.62 (m, 1H, H-$5_A$), 3.54 (dd, 1H, $J_{4,5}$=9.9 Hz, $J_{4,3}$=9.9 Hz, H-$4_D$), 3.52 (dd, 1H, $J_{4,5}$=9.8 Hz, $J_{4,3}$=9.8 Hz, H-$4_C$), 3.42 (m, 1H, H-$5_D$), 3.38 (dd, 1H, $J_{4,5}$=9.8 Hz, $J_{4,3}$=9.8 Hz, H-$4_B$), 3.37 (dd, 1H, $J_{4,5}$=9.8 Hz, $J_{4,3}$=9.8 Hz, H-$4_A$), 1.25 (d, 3H, $J_{6,5}$=6.2 Hz, H-$6_B$), 1.20 (d, 3H, $J_{6,5}$=6.4 Hz, H-$6_A$), 1.19 (d, 3H, $J_{6,5}$=6.4 Hz, H-$6_C$).

$^{13}C$ NMR (800 MHz, $D_2O$), δ 168.6 ($CO_{ClAc}$), 164.7 ($CO_{NHC(O)CCl_3}$), 133.0 ($CH═_{All}$), 118.7 (═$CH_{2AB}$), 102.3 (C-$1_A$), 100.5 (C-$1_B$), 99.1 (C-$1_D$), 98.5 (C-$1_C$), 91.6 ($CCl_3$), 81.7 (C-$3_D$), 78.0 (C-$2_B$), 76.1 (C-$5_D$), 74.5 (C-$3_C$), 73.4 (C-$2_C$), 72.2 (C-$4_C$), 72.0 ($2_C$, C-$4_B$, C-$4_A$), 70.8 (—$CH_2$—$_{All}$), 70.0 (2C, C-$3_A$, C-$2_A$), 69.9 (C-$3_B$), 69.5 (C-$5_B$), 69.2 (C-$5_C$), 69.1 (C-$5_A$), 68.5 (C-$4_D$), 60.7 (C-$6_D$), 57.1 (C-$2_D$), 40.7 (—$CH_{2\text{-}ClAc}$), 16.7 (C-$6_B$), 16.6 (C-$6_A$), 16.2 (C-$6_C$).

HRMS (ESI+): m/z 895.1840 (calcd for $C_{31}H_{47}Cl_4NO_{19}NH_4$ [M+$NH_4$]$^+$) found m/z 895.1860.

Allyl α-L-rhamnopyranosyl-(1→2)-α-L-rhamnopyranosyl-(1→3)-2-O-chloroacetyl-α-L-rhamnopyranosyl-(1→3)-2-deoxy-2-N-trichloroacetyl-β-D-glucopyranoside (21a)

To a solution of the lightly protected tetrasaccharide $AB_{ClAc}C_{Cl3Ac}D$-All (21, 200 mg, 0.23 mmol) in anhydrous methanol (31 mL) was added MeONa (25% w/w in MeOH, 126 μL, 0.55 mmol, 2.4 equiv.). After stirring the reaction mixture for 3 h, a TLC follow up (cyclohexane/ethyl acetate 8:2) showed complete consumption of the starting material (Rf=0.15). Dowex $H^+$ was then added until neutralization and filtered off, volatiles were evaporated under reduced pressure. The residue was purified by reverse phase chromatography eluting from a C18 column (water/MeCN 1:0 to 6:4) to give, after lyophilization, tetrasaccharide $ABC_{Cl3Ac}D$-All 21a as a white powder (76 mg, 42%). RP-HPLC (C18 ® RP fusion (4.6×250 mm, 4.0 μm, 80 Å, $CH_3CN$ in $H_2O$ (30% for 4 min, then 30→40% over 7 min, at 1.0 mL·min$^{-1}$), 40° C., λ: 220 nm)=3.8 min.

HRMS (ESI$^+$): m/z 819.2124 (calcd for $C_{30}H_{46}Cl_3NO_{18}NH_4$ [M+$NH_4$]$^+$) found m/z 819.2745; m/z 824.1618 (calcd for $C_{30}H_{46}Cl_3NO_{18}Na$ [M+Na]$^+$) found m/z 824.2239.

Synthesis of an Alternative B Donor (25)

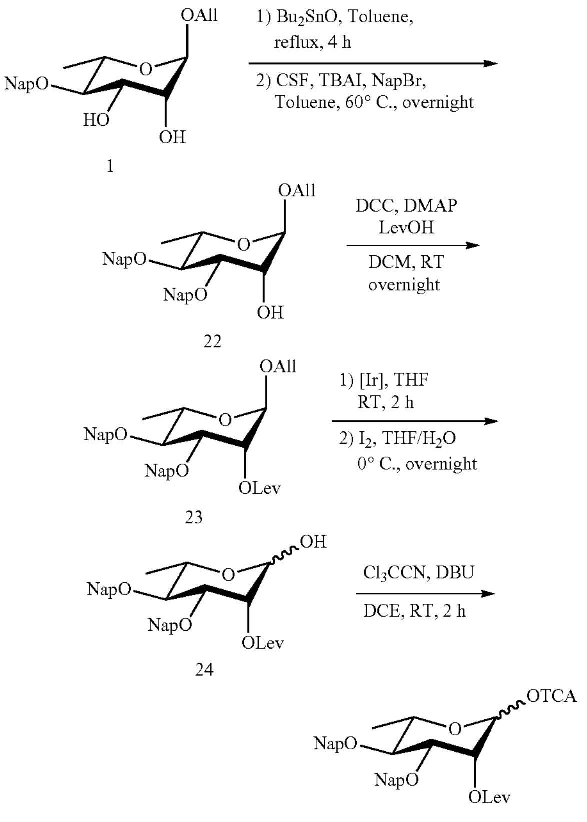

1
22
23
24
25

Allyl 3,4-di-O-(2-naphtylmethyl)-α-L-rhamnopyranoside (22)

Dibutyltin oxide (4.0 g, 1.1 equiv) was added to a solution of diol 1 (5.0 g, 15.0 mmol) in anhydrous toluene (100 mL). The mixture was stirred for 2 h at reflux using a Dean-Stark apparatus. After cooling to rt, dry CsF (2.2 g, 1.0 equiv), dry tetrabutylammonium iodide (6.97 g, 1.3 equiv) and 2-naphtylmethyl bromide (3.54 g, 1.1 equiv.) were successively added. After heated at 60° C. overnight, a TLC control (toluene/EtOAc 8:2) showed the total consumption of starting diol 1. After cooling to 0° C., salts were removed by filtration over a pad of Celite® and solvents were evaporated under reduced pressure. The crude was purified by flash chromatography to give alcohol 22 (5.02 g, 69%) as a brown oil.

$^1H$ NMR ($CDCl_3$) δ 7.81 (m, 8H, $H_{ArNap}$), 7.50 (m, 6H, $H_{ArNap}$), 5.93 (m, 1H, $J_{trans}$=17.1 Hz, $J_{gem}$=1.5 Hz, CH═$CH_2$), 5.31 (m, 1H, $J_{cis}$=10.4 Hz, CH═$CH_2$), 5.22 (m, 1H, CH═$CH_2$), 5.10 (d, 3H, J=11.2 Hz, $CH_{2Nap}$), 4.91 (m, 2H, $CH_{2Nap}$, H-1), 4.21 (m, 1H, $H_{All}$), 4.16 (m, 1H, H-2), 4.02 (m, 2H, $H_{All}$, H-3), 3.85 (m, 1H, H-5), 3.60 (pt, 1H, $J_{3,4}$=$J_{4,5}$=9.3 Hz, H-4), 2.58 (bs, 1H, $J_{2,OH}$=9.6 Hz, OH), 1.40 (d, 3H, $J_{5,6}$=6.3 Hz, H-6).

HRMS (ESI$^+$): m/z 502.2608 (calcd for $C_{31}H_{36}O_5N$ $[M+NH_4]^+$ m/z 502.2593)

Allyl 2-O-levulinyl-3,4-di-O-(2-naphtylmethyl)-α-L-rhamnopyranoside (23)

To a solution of alcohol 22 (5.02 g, 9.0 mmol) in anhydrous DCM (42 mL) stirred at room temperature were successively added DCC (3.16 g, 1.7 equiv), DMAP (440 mg, 0.4 equiv) and levulinic acid (1.94 mL, 4.2 equiv). After stirring the reaction mixture overnight at room temperature, TLC (toluene/EtOAc 7:3) showed complete consumption of the starting material. The reaction mixture was filtered over a pad of Celite®, and volatiles were evaporated under reduced pressure. The crude material was taken in ethyl acetate (50 mL) and the organic layer was washed thrice with 10% aqueous copper (II) sulfate (30 mL), water (30 mL), saturated aqueous sodium bicarbonate (30 mL) and brine (30 mL). The organic layer was dried by stirring over anhydrous sodium sulfate, filtered and concentrated under vacuum. The crude material was used as such in the next step.

2-O-Levulinyl-3,4-di-O-(2-naphtylmethyl)-α-L-rhamnopyranose (24)

To a solution of the fully protected 23 (from 22, 9.0 mmol) in anhydrous THF (50 mL) stirred at room temperature was added hydrogen-activated [Ir] (152 mg, 0.02 equiv) in anhydrous THF (10 mL). After stirring the reaction mixture for 2 hours at room temperature, another 0.02 equiv of hydrogen-activated [Ir] vas added and the reaction mixture was stirred overnight at room temperature. TLC (cyclohexane/EtOAc 6:4) showed that the starting allyl rhamnoside had been consumed. Iodine (2.74 g, 1.2 equiv) in water/THF (1:5, 72 mL). After stirring the reaction mixture for 1 h at this temperature, TLC (cyclohexane/EtOAc 6:4) showed complete conversion of the intermediate into a more polar product. 10% aqueous sodium metabisulfite was added. THF was evaporated under reduced pressure and DCM (50 mL) was added. The aqueous layer was extracted twice with DCM (30 mL) and the combined organic phases were washed with saturated aqueous sodium bicarbonate and then brine. The organic layer was dried over anhydrous sodium sulfate, filtered and concentrated under vacuum. The crude material was used as such in the next step.

2-O-Levulinyl-3,4-di-O-(2-naphtylmethyl)-α-L-rhamnopyranosyl trichloroacetimidate (25)

To a solution of hemiacetal 24 (from 22, 9.0 mmol) in anhydrous DCE (50 mL) stirred at room temperature were successively added $Cl_3CCN$ (2.7 mL, 3.0 equiv) and DBU (670 μL, 0.5 equiv). After stirring the reaction mixture for 2 h at room temperature, TLC (toluene/EtOAc7:3) showed complete consumption of the starting material. Volatiles were evaporated under reduced pressure. The residue was purified by chromatography eluting from a column of $Et_3N$-treated silica gel (toluene/EtOAc 95:5 to 8:2 containing $Et_3N$ 5%) to give donor 25 as a brown oil (5.05 g, 88% over three steps).

$^1$H NMR ($CDCl_3$) δ 8.67 (s, 1H, NH), 7.81 (m, 8H, $H_{ArNap}$), 7.49 (m, 6H, $H_{ArNap}$), 6.22 (d, 1H, H-1), 5.56 (dd, 1H, $J_{1,2}$=2.1 Hz, $J_{2,3}$=3.3 Hz, H-2), 5.14 (d, 1H, J=11.1 Hz, $CH_{2Nap}$), 4.92 (d, 1H, J=11.4 Hz, $CH_{2Nap}$), 4.87 (d, 1H, $CH_{2Nap}$), 4.77 (d, 1H, $CH_{2Nap}$), 4.10 (dd, 1H, H-3), 4.00 (m, 1H, H-5), 3.62 (pt, 1H, $J_{3,4}$=$J_{4,5=9.5}$ Hz, H-4), 2.78 (m, 4H, $CH_{2Lev}$), 2.18 (s, 3H, $CH_{3Lev}$), 1.40 (d, 3H, $J_{5,6}$=6.2 Hz, H-6)

$^{13}$C NMR ($CDCl_3$) δ 206.0 ($CO_{Lev}$), 171.9 ($CO_{2Lev}$), 160.1 (NHCO), 135.6-133.2 (6C, $C_{IV}$), 128.2-126.1 (14C, $C_{ArNap}$), 95.2 (C-1, $J_{C\text{-}H}$=179.5 Hz), 79.4 (C-4), 77.1 (C-3), 75.7 ($C_{Nap}$), 72.0 ($C_{Nap}$), 70.8 (C-5), 67.9 (C-2), 38.0 ($CH_{2Lev}$), 29.8 ($CH_{3Lev}$), 28.1 ($CH_{2Lev}$), 18.1 (C-6).

HRMS (ESI$^+$): m/z 703.1744 (calcd for $C_{35}H_{38}Cl_3NO_7$ $[M+NH_4]^+$ m/z 703.1749)

Synthesis of an Alternative C Acceptor (28)

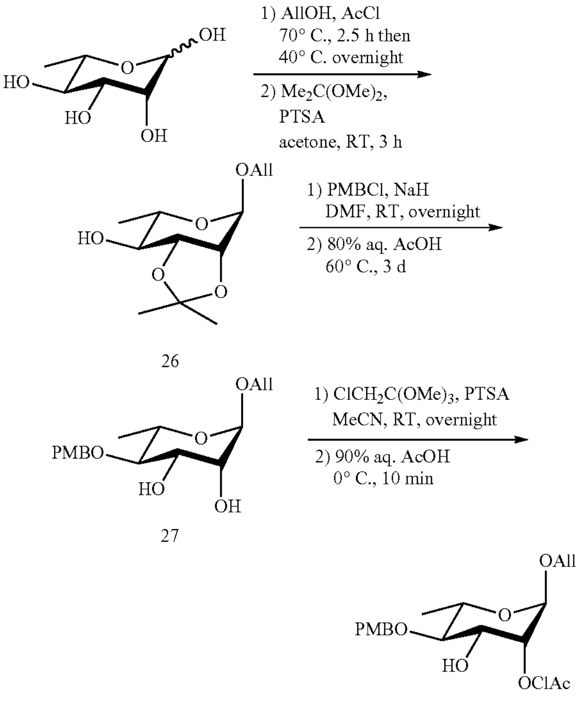

26

27

28

Allyl 4-O-para-methoxybenzyl-α-L-rhamnopyranoside (27)

Crude allyl 2,3-O-isopropylidene-α-L-rhamnopyranoside (26, from L-rhamnose, 110 mmol) was dissolved in DMF (320 mL) under Argon, the bath temperature was cooled to −5° C. and NaH (60% oil dispersion, 10.6 g, 2.4 equiv.) was added portionwise to this suspension. The mixture was stirred for 2 h at rt, then para-methoxybenzyl chloride (17.9 mL, 1.2 equiv.) was added dropwise at −5° C. and the reaction mixture was stirred at rt overnight. Follow up by TLC (toluene/EtOAc 8:2) indicated the total conversion of the intermediate alcohol into a less polar product. The reaction was quenched at 0° C. by addition of MeOH (20 mL). Solvents were eliminated under reduced pressure and volatiles were co-evaporated with toluene. The residue was taken up in EtOAc (200 mL) and washed with $H_2O$ (3×120 mL) and brine (120 mL). The organic phase was dried over anhydrous $Na_2SO_4$, filtered, and concentrated to dryness to give the fully protected intermediate.

The crude intermediate was dissolved in 80% aq. AcOH (200 mL) and the solution was stirred for 3 d at 60° C. Follow up by TLC (toluene/EtOAc 7:3) indicated the total conversion of the intermediate acetal into a more polar product. Solvents were removed under vacuum and traces of AcOH were eliminated by co-evaporation with cyclohexane (2×100 mL) to give a brown solid. Crystallization from cyclohexane and column chromatography of the mother liquor eluting with toluene/EtOAc 8:2 to 6:4) gave diol 28 (27.9 g, 78% over four steps), m.p.=72° C. (cyclohexane).

$^1$H NMR ($CDCl_3$) δ 7.30 (m, 2H, $H_{ArPMB}$), 6.91 (m, 2H, $H_{ArPMB}$), 5.89 (m, 1H, CH═$CH_2$), 5.29 (m, 1H, $J_{trans}$=17.2 Hz, $J_{gem}$=1.6 Hz, CH═$CH_2$), 5.20 (m, 1H, $J_{trans}$=10.4 Hz, CH═$CH_2$), 4.81 (d, 1H, $J_{1,2}$=1.1 Hz, H-1), 4.69 (m, 2H, $CH_{2PMB}$), 4.17 (m, 1H, $H_{All}$), 3.97 (m, 3H, H-All, H-2, H-3), 3.82 (s, 3H, $CH_{3PMB}$), 3.75 (m, 1H, H-5), 3.35 (pt, 1H, $J_{3,4}$=$J_{4,5}$=9.2 Hz, H-4), 2.45 (bs, 2H, OH), 1.36 (d, 3H, $J_5$,6=6.3 Hz, H-6).

Allyl 2-O-chloroacetyl-4-O-para-methoxybenzyl-α-L-rhamnopyranoside (28)

Diol 27 (1.0 g, 3.0 mmol) was solubilized in anhydrous acetonitrile (MeCN, 5 mL). To the solution was added trimethylchloroorthoacetate (1.39 mL, 3.0 equiv) and APTS (59 mg, 0.1 equiv). The solution was stirred at room temperature for 1 hour (reaction followed by TLC toluene/EtOAc 7:3). To the reaction medium cooled to 0° C. was added a 90% aqueous TFA (2.0 mL) and the reaction mixture was stirred at room temperature for 10 min. Water was added until the mixture became completely cloudy. The product was extracted with DCM (2×25 mL). The organic phase was washed with saturated aqueous $NaHCO_3$ (2×25 mL) and brine (25 mL). The aqueous phase was extracted with DCM (2×12.5 mL). The combined organic phases were dried over $Na_2SO_4$, filtered, evaporated and finally co-evaporated with toluene to yield alcohol 28 as a mixture of regioisomers. The crude material is used as such in the next step.

Synthesis of $_{Cl3Ac}$DAB$_{ClAc}$C-All $_{Cl3Ac}$DAB$_{ClAc}$C-All is obtained following route B' as defined below.

In particular, it can be obtained from donor 12 or its 4,6-O-benzylidene analog and the ABC trioside acceptor 29 following conventional delevulinylation at position $2_A$ of the fully protected precursor 16. A synthesis is highlighted in the scheme below whereby $R^1$=$R^4$=Nap, $R^3$=$R^6$=TES, $R^2$=ClAc, $R^5$=Lev, $R^7$=TBS, $R^8$=All, $R^9$=Cl3Ac).

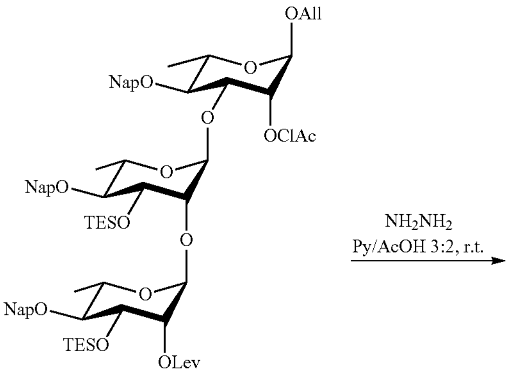

16

-continued

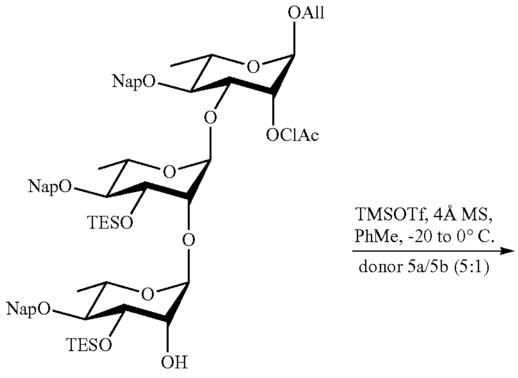

29

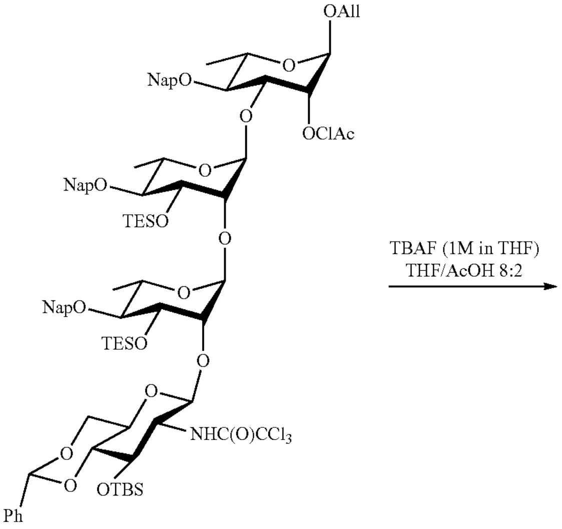

30

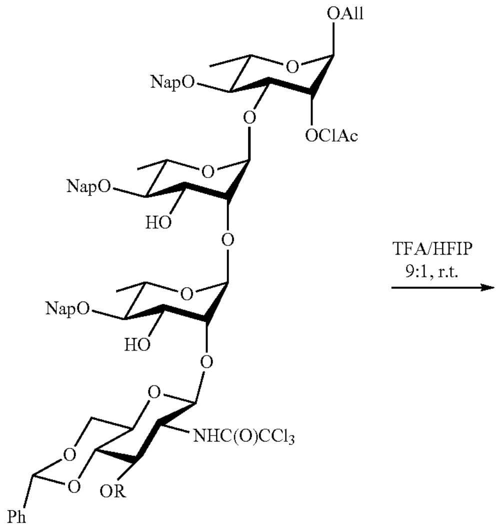

2:1 31 R = H
32 R = TBS

-continued

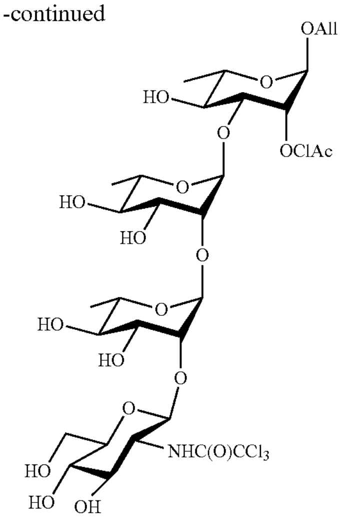

33

Allyl 4,6-O-benzylidene-3-O-tert-butyldimethylsilyl-2-deoxy-2-trichloroacetamido-β-D-glucopyranosyl-(1-2)-4-O-(2-naphtylmethyl)-α-L-rhamnopyranosyl-(1-2)-4-O-(2-naphtylmethyl)-α-L-rhamnopyranosyl-(1→3)-2-O-chloroacetyl-4-O-(2-naphtylmethyl)-α-L-rhamnopyranoside (32) and allyl 4,6-O-benzylidene-2-deoxy-2-trichloroacetamido-$-D-glucopyranosyl-(1→2)-4-O-(2-naphtylmethyl)-α-L-rhamnopyranosyl-(1→2)-4-O-(2-naphtylmethyl)-α-L-rhamnopyranosyl-(1→3)-2-O-chloroacetyl-4-O-(2-naphtylmethyl)-α-L-rhamnopyranoside (31)

To a solution of crude tetrasaccharide 30 (1.48 mmol) in THF/AcOH (4:1, 74 mL) was slowly added 1M TBAF in THF (14.8 mL, 14.8 mmol, 10.0 equiv.). After stirring the reaction mixture overnight at rt, were added TBAF (1M solution in THF, 14.8 mL, 14.8 mmol, 10.0 equiv.) and AcOH (14.8 mL). After stirring the reaction mixture for 2 days at rt, a TLC follow up (cyclohexane/ethyl acetate 7:3) showed the presence of a complex mixture of products (Rf=0.05, 0.25, 0.35, 0.45 and 0.55). Distilled water (20 mL) and toluene (50 mL) were added. The organic layer was washed with satd aq. $NaHCO_3$ (20 mL) and brine (20 mL). The organic layer was dried over anhydrous sodium sulfate, filtered and concentrated and co-evaporated with toluene under vacuum. The residue was purified by chromatography eluting from a column of silica gel (toluene/ethyl acetate 95:5 to 4:6) to give by order of elution diol 32 (820 mg, 37%) and triol 31 (334 mg, 16%).

Allyl 2-deoxy-2-trichloroacetamido-β-D-glucopyranosyl-(1→2)-α-L-rhamnopyranosyl-(1→2)-α-L-rhamnopyranosyl-(1→3)-2-O-chloroacetyl-α-L-rhamnopyranoside (33)

A solution of tetrasaccharide 31 (334 mg, 0.24 mmol) in trifluoroacetic acid/1,1,1,3,3,3-hexafluoro-2-propanol (9:1, 3.0 mL) is stirred at rt for 2 h. Toluene (10 mL) was added and volatiles were evaporated and co-evaporated with toluene (five times) under reduced pressure. The residue was dissolved in water (10 mL) and dichloromethane (5 mL). The organic phase was washed with water (10 mL) and the aq. phases were freeze-dried and lyophilized. The residue was purified by reverse phase chromatography eluting from a C18 column ($H_2O$/MeCN 0→40%) to give the lightly protected tetrasaccharide D'ABC'-All (33) as a white powder (74 mg, 35%). RP-HPLC (C18® RP fusion (4.6×250 mm, 4.0 μm, 80 Å, $CH_3CN$ in $H_2O$ (30% for 4 min, then 30→40% over 7 min, at 1.0 mL·min$^{-1}$), 40° C., λ: 220 nm)=10.2 min.

HRMS (ESI+): m/z 900.1394 (calcd for $C_{31}H_{47}Cl_4NO_9Na$ $[M+Na]^+$) found m/z 900.1246.

Example 2: Enzymatic α-D-Glucosylation of a Compound of Formula (I) with Branching Sucrases Enzymes Table 1 presents some enzymes that were used in the context of the present invention.

| Enzyme accronym | Osidic linkage on natural acceptor | Source organism | References |
|---|---|---|---|
| BRS-B | α-1,3 | *Leuconostoc citreum* NRRL-B 742 | US2016136199 (A1), Route B' WO2016146764 (A1) Vuillemin et al. (JBC, 2016) |
| BRS-C | | *Leuconostoc fallax* KCTC 3537 | US2016136199 (A1), WO2016146764 (A1) Vuillemin et al. (JBC, 2016) |
| BRS-E | | *Leuconostoc mesenteroides* KFRI-MG | |
| BRS-A | α-1,2 | *Leuconostoc citreum* NRRL-B 1299 | US2017152489 (A1), US2017101484 (A1), ES2398227 (T3) Vuillemin et al. (JBC, 2016) |
| BRS-D | | *Lactobacillus kunkei* EFB6 | US2017152489 (A1), US2017101484 (A1), ES2398227 (T3) Vuillemin et al. (JBC, 2016) |
| GBD-CD2 | | From truncated DSR-E *Leuconostoc citreum* NRRL-B 1299 | US2017152489 (A1), US2017101484 (A1), ES2398227 (T3) Fabre et al. (J. Bact, 2004), Brison et al. (JBC, 2012) |
| GBD-CD2 W2135V*<br>GBD-CD2 W2135C-F2136I*<br>GBD-CD2 W2135S-F2136L*<br>GBD-CD2 W2135I-F2136C*<br>GBD-CD2 W2135N-F2136Y*<br>GBD-CD2 W2135N*<br>GBD-CD2 W2135I-F2136Y*<br>GBD-CD2 W2135L*<br>GBD-CD2 W2135C*<br>GBD-CD2 W2135N-F2136H*<br>GBD-CD2 W2135L-F2136L*<br>GBD-CD2 | | GBD-CD2 mutants | Yannick Malbert. Flavonoid glucodiversification with engineered sucrose-active enzymes. Biotechnology. INSA Toulouse (PhD, 2014) |

-continued

| Enzyme accronym | Osidic linkage on natural acceptor | Source organism | References |
|---|---|---|---|
| W2135F-F2136I* | | | |
| GBD-CD2 W2135C-F2136N* | | | |
| GBD-CD2 W2135G* | | | |
| GBD-CD2 W2135F* | | | |
| GBD-CD2 F2163G* | | | |
| GBD-CD2 L2166I* | | | |
| GBD-CD2 F2163H* | | | |
| GBD-CD2 F2163G L2166I* | | | |
| GBD-CD2 A2162E F2163L* | | | |
| GBD-CD2 F2163L* | | | |
| GBD-CD2 F2163I-D2164E-L2166I* | | | |

*The mutations are given relatively to the sequence of the GBD-CD2 wild type.

The sequence of said enzymes is as follows:
SEQ ID NO: 1 (BRS-E)
SEQ ID NO: 2 (BRS-A)
SEQ ID NO: 3 (BRS-B-D1)
SEQ ID NO: 4 (BRS-B-D2)
SEQ ID NO: 5 (BRS-C)
SEQ ID NO: 6 (BRS-D)
SEQ ID NO: 7 (GBD-CD2).

| | |
|---|---|
| BRS-E (*L. Mesenteroides* KFRI-MG) | MAHHHHHHVTSLYKKAGSAAAPFTMQQNNATLQVSPTKNDNSVAKNTTS<br>TANVAKVDITTDNTRDISSANNVNNLITNQYKENSNGSWSYYDNNGQIVKG<br>LQTINGNIQYFDSTTGEQVKGQTLTIDGVIYSFDKDSGNGTKTEVASLPTTGS<br>YATKDGSNWQYEDQQQQ PIKGLYTDKG NLRYFNETDG TQVKGTVVSV<br>DNNTYYFDKDSGNGQLVPSVTGGQYGTIQLNNQTVWVYRNANGEIVKGLQ<br>NINGNIQYFDPNTGEQLKGKVATVNGVTYY FEASDGNLVG TVSDGLVTVN<br>GQIQYFDPATGEQAKNKQVI VNNVTYYFDDNGYGQYLFTNAILSTTPDAY<br>SAHTQAYNTDQSSFTNVVDGFLTADSWYRPKEVIADATGS AWQTSSENDY<br>RPIITVWWPNKNVEVNYLKLMQDNDLLSTQ TQFTIFSDQY TLNEAAQAAQ<br>NEIEKRIYREKSTDWLKDLLFEAHGDTPSF VKQQFIWNKD SEYQGAGGGN<br>LWSLQGGYLK YVNDSETSWS DSTSRKHDYY EYLLGNDIDN SNPQVIAENI<br>NWLYYLMNFGSLTGNDDTANFDGVRMDAVIYMKGEASTKVYQFLHKSDE<br>L TKNEKIANEH ISIVEDGTDETTKNNSALIV SKWNENIASS LAKIASGKDT<br>SLEALVKTDE KTSVSRIMNS SVESDVNPNY SMIRSHDRGS QDEVINASKV<br>ANNDQSIALD NINLNQLENG LKLYYEDQAS PTKNYNYYNI PASYALLLSN<br>KDTVPRLYYSDMYQDYDQNPDTPQQYMSKP TIYYSAIDAL LKARIKYVAG<br>GQSMAVEKVGDNKDQEVLTSVRYGKNVMTATDTGTVESRTEGMGVIVSN<br>NTKLKLSTTDQIVLHMGAAHANQAYQALMLINDEGIQLYNDNAPVVWTD<br>HNGDLVFNGNDINGQKNTSIKGYFNPQVAGYLAVWVPVGATDTQDARTK<br>ASTNATTDGKVFHSNAALDSNVIYEGFSNFQPIARNHNDFSNVKIAENVDLF<br>KKWGITSFELAPQYRSADVSDLVGSTFVDVVTKNGYGLSDRYDLGFVTPTK<br>YGSDSDLRNAISSLHAQGIQAMADFVGNQIYALNDGQEVVTAQRSDMENN<br>TLNNAFGTELYVVNSIGGGKYQAKYGGNYLEEIASLYPDLFTNQDGTKIDIN<br>TKIKQWSAKYMNGTNVLGRGMGYVLKDWNTATYFKLDGEHTVLPAALTL<br>SGLKVENGVTYYYKNNERQTGTQTVDDVTYFFDPKTGAMKKDYFDFTAD<br>NKVYYYGKGGRADPAFLYKV VSAWSHPQFE K |
| BRS-A, 1878 amino acids (*L. citreum* NRRL B-1299) | MRQKETITRKKLYKSGKSWVAAATAFAVMGVSAVTTVSADTQTPVGTTQS<br>QQDLTGQRGQDKPTTKEVIDKKEPVPQVSAQNAGDLSADAKTTKADDKQD<br>TQPTNAQLPDQGNKQTNSNSDKGVKESTTAPVKTTDVPSKSVTPETNTSING<br>GQYVEKDGQFVYIDQSGKQVSGLQNIEGHTQYFDPKTGYQTKGELKNIDDN<br>AYYFDKNSGNGRTFTKISNGSYSEKDGMWQYVDSHDKQPVKGLYDVEGN<br>LQYFDLSTGNQAKHQIRSVDGVTYYFDADSGNATAFKAVINGRYAEQT<br>TKDKDGNETSYWAYLDNQGNAIKGLNDVNGEIQYFDEHTGEQLKGHTATL<br>DGTTYYFEGNKGNLVSVVNTAPTGQYKINGDNVYYLDNNNEAIKGLYGIN<br>GNLNYFDLATGIQLKGQAKNIDGIGYYFDKDTGNGSYQYTLMAPSNKNDY<br>TQHNVVNNLSESNFKNLVDGFLTAETWYRPAQILSHGTDWVASTDKDFRPL<br>ITVWWPNKDIQVNYLRLMQNEGVLNQSAVYDLNTDQLLLNEAAQQAQIGI<br>EKKISQTGNTDWLNNVLFTTHDGQPSFIKQQYLWNSDSEYHTGPFQGGY<br>LKYQNSDLTPNVNSKYRNADNSLDFLLANDVDNSNPIVQAEDLNWLYYLL<br>NFGSITTQGKENNSNFDSIRIDAVDFVSNDLIQRTYDYLRAAYGVDKNDKEA<br>NAHLSLVEAGLDAGTTTIHQDALIESDIREAMKKSLINGPGSNISLSNLIQDK<br>EGDKLIADRANNSTENVAIPNYSIIHAHDKDIQDKVGAAITDATGADWTNFT<br>PEQLQKGLSLYYEDQRKIEKKYNQYNIPSAYALLLTNKDTVPRVYYGDMY<br>QDDGQYMQKQSLYFDTITALMEARKQFVAGGQTINVDDNGVLTSVRFGKG<br>AMTANDIGTNETRTQGIGVVIANDPSLKLSKDSKVTLHMGAAHRNQNYRA<br>LLLTTDNGIDSYSSSKNAPVIKTDDNGDLVFSNQDINDQLNTKVHGFLNSEV<br>SGYLSAWVPLDATEQQDARTLPSEKSVNDGKVLHSNAALDSNLIYEAFSNF<br>QPMPTNRNEYTNVVIADKADTFKSWGITSFEMAPQYRSSQDKTFLDSTIDN<br>GYAFTDRYDLGFEKPTKYGNDEDLRQAIKQLHSSGMQVMADVVANQIYNL<br>PGKEVASTNRVDWNGNNLSTPFGTQMYVVNTVGGGKYQNKYGGEFLDKL<br>KAAYPDIFRSKNYEYDVKNYGGNGTGSVYYTVDSKTRAELDTDTKIKEWS |

-continued

AKYMNGTNVLGLGMGYVLKDWQTGQYFNVSNQNMKFLLPSDLISNDITV
QLGVPVTDKKIIFDPASAYNMYSNLPEDMQVMDYQDDKKSTPSIKPLSSYN
NKQVQVTRQYTDSKGVSWNLITFAGGDLQGQKLWVDSRALTMTPFKTMN
QISFISYANRNDGLFLNAPYQVKGYQLAGMSNQYKGQQVTIAGVANVSGK
DWSLISFNGTQYWIDSQALNTNFTHDMNQKVFVNTTSNLDGLFLNAPYRQP
GYKLAGLAKNYNNQTVTVSQQYFDDQGTVWSQVVLGGQTVWVDNHALA
QMQVRDTNQQLYVNSNGRNDGLFLNAPYRGQGSQLIGMTADYNGQHVQV
TKQGQDAYGAQWRLITLNNQQVWVDSRALSTTIMQAMNDDMYVNSSQRT
DGLWLNAPYTMSGAKWAGDTRSANGRYVHISKAYSNEVGNTYYLTNLNG
QSTWIDKRAFTATFDQVVALNATIVARQRPDGMFKTAPYGEAGAQFVDYV
TNYNQQTVPVTKQHSDAQGNQWYLATVNGTQYWIDQRSFSPVVTKVVDY
QAKIVPRTTRDGVFSGAPYGEVNAKLVNMATAYQNQVVHATGEYTNASGI
TWSQFALSGQEDKLWIDKRALQA

BRS-B

MEMKETITRKKLYKSGKSWVAAATAFAVMGVSAVTTVSADTQTPVGTTQS
QQDLTGQTGQDKPTTKEVIDKKEPVPQVSAQNVGDLSADAKTPKADDKQD
TQPTNAQLPDQGNKQTNSNSDKGVKESTTAPVKTTDVPSKSVAPETNTSIN
GGQYVEKDGQFVYIDQSGKQVSGLQNIEGHTQYFDPKTGYQTKGELKNIDD
NAYYFDKNSGNGRTFTKISNGSYSEKDGMWQYVDSHDKQPVKGLYDVEG
NLQYFDLSTGNQAKHQIRSVDGVTYYFDADSGNATAFKAVTNGRYAEQTT
KDKDGNETSYWAYLDNQGNAIKGLNDVNGEIQYFDEHTGEQLKGHTATV
DGTTYYFEGNKGNLVSVVNTAPTGQYKINGDNVYYLDNNNEAIKGLYGIN
GNLNYFDLATGIQLKGQAKNIDGIGYYFDQNNGNGEYRYSLTGPVVKDVY
SQHNAVNNLSANNFKNLVDGFLTAETWYRPAQILSHGTDWVASTDKDFRP
LITVWWPNKDIQVNYLKLMQQIGILDNSVVFDTNNDQLVLNKGAESAQIGI
EKKVSETGNTDWLNELLFAPNGNQPSFIKQQYLWNVDSEYPGGWFQGGYL
AYQNSDLTPYANTNPDYRTHNGLEFLLANDVDNSNPVVQAEQLNWLYYL
MNFGQITANDSNANFDSMRIDAISFVDPQIAKKAYDLLDKMYGLTDNEAV
ANQHISIVEAPKGETPITVEKQSALVESNWRDRMKQSLSKNATLDKLDPDPA
INSLEKLVADDLVNRSQSSDKDSSTIPNYSIVHAHDKDIQDTVIHIMKIVNNN
PNISMSDFTMQQLQNGLKAFYEDQHQSVKKYNQYNIPSAYALLLTNKDTVP
RVFYGDMYQDYGDDLDGGQYMATKSIYYNAIEQMMKARLKYVAGGQIM
AVTKIKNDGINKDGTNKSGEVLTSVRFGKDIMDAQGQGTAESRNQGIGVIV
SNSSGLELKNSDSITLHMGIAHKNQAYRALMLTNDKGIVNYDQDNNAPIAW
TNDHGDLIFTNQMINGQSDTAVKGYLNPEVAGYLAVWVPVGANDNQDAR
TVTTNQKNTDGKVLHTNAALDSKLMYEGFSNFQKMPTRGNQYANVVITKN
IDLFKSWGITDFELAPQYRSSDGKDITDRFLDSIVQNGYGLSDRYDLGFKTPT
KYGTDQDLRKAIERLHQAGMSVMADFVANQIYGLHADKEVVSAQHVNIN
GDTKLVVDPRYGTQMTVVNSVGGGDYQAKYGGEYLDTISKLYPGLLLDSN
GQKIDLSTKIKEWSAKYLNGSNIPQVGMGYVLKDWNNGQYFHILDKEGQY
SLPTQLVSNDPETQIGESVNYKYFIGNSDATYNMYHNLPNTVSLINSQEGQI
KTQQSGVTSDYEGQQVQVTRQYTDSKGVSWNLITFAGGDLQGQKLWVDS
RALTMTPFKTMNQISFISYANRNDGLFLNAPYQVKGYQLAGMSNQYKGQQ
VTIAGVANVSGKDWSLISFNGTQYWIDSQALNTNFTHDMNQKVFVNTTSNL
DGLFLNAPYRQPGYKLAGLAKNYNNQTVTVSQQYFDDQGTVWSEVVLGG
QTVWVDNHALAQMQVSDTSQQLYVNSNGRNDGLFLNAPYRGQGSQLIGM
TADYNGQHVQVTKQGQDAYGAQWRLITLNNQQVWVDSRALSTTIVQAMN
DDMYVNSNQRTDGLWLNAPYTMSGAKWAGDTRSANGRYVHISKAYSNEV
GNTYYLTNLNGQSTWIDKRAFTATFDQVVALNATIVARQRPDGMFKTAPY
GEAGAQFVDYVTNYNQQTVPVTKQHSDAQGNQWYLATVNGTQYWIDQRS
FSPVVTKVVDYQAKIVPRTTRDGVFSGAPYGEVNAKLVNMATAYQNQVV
HATGEYTNASGITWSQFALSGQEDKLWIDKRALQA

BRS-B-D1 (*L. citreum* NRRL B-742)

DTQTPVGTTQSQQDLTGQTGQDKPTTKEVIDKKEPVPQVSAQNVGDLSADA
KTPKADDKQDTQPTNAQLPDQGNKQTNSNSDKGVKESTTAPVKTTDVPSK
SVAPETNTSINGGQYVEKDGQFVYIDQSGKQVSGLQNIEGHTQYFDPKTGY
QTKGELKNIDDNAYYFDKNSGNGRTFTKISNGSYSEKDGMWQYVDSHDKQ
PVKGLYDVEGNLQYFDLSTGNQAKHQIRSVDGVTYYFDADSGNATAFKAV
TNGRYAEQTTKDKDGNETSYWAYLDNQGNAIKGLNDVNGEIQYFDEHT
GEQLKGHTATVDGTTYYFEGNKGNLVSVVNTAPTGQYKINGDNVYYLDN
NNEAIKGLYGINGNLNYFDLATGIQLKGQAKNIDGIGYYFDQNNGNGEYRY
SLTGPVVKDVYSQHNAVNNLSANNFKNLVDGFLTAETWYRPAQILSHGTD
WVASTDKDFRPLITVWWPNKDIQVNYLKLMQQIGILDNSVVFDTNNDQLV
LNKGAESAQIGIEKKVSETGNTDWLNELLFAPNGNQPSFIKQQYLWNVDSE
YPGGWFQGGYLAYQNSDLTPYANTNPDYRTHNGLEFLLANDVDNSNPVV
QAEQLNWLYYLMNFGQITANDSNANFDSMRIDAISFVDPQIAKKAYDLLDK
MYGLTDNEAVANQHISIVEAPKGETPITVEKQSALVESNWRDRMKQSLSKN
ATLDKLDPDPAINSLEKLVADDLVNRSQSSDKDSSTIPNYSIVHAHDKDIQD
TVIHIMKIVNNNPNISMSDFTMQQLQNGLKAFYEDQHQSVKKYNQYNIPSA
YALLLTNKDTVPRVFYGDMYQDYGDDLDGGQYMATKSIYYNAIEQMMKA
RLKYVAGGQIMAVTKIKNDGINKDGTNKSGEVLTSVRFGKDIMDAQ
GQGTAESRNQGIGVIVSNSSGLELKNSDSITLHMGIAHKNQAYRALMLTND
KGIVNYDQDNNAPIAWTNDHGDLIFTNQMINGQSDTAVKGYLNPEVAGYL
AVWVPVGANDNQDARTVTTNQKNTDGKVLHTNAALDSKLMYEGFSNFQK
MPTRGNQYANVVITKNIDLFKSWGITDFELAPQYRSSDGKDITDRFLDSIVQ
NGYGLSDRYDLGFKTPTKYGTDQDLRKAIERLHQAGMSVMADFVANQIYG
LHADKEVVSAQHVNINGDTKLVVDPRYGTQMTVVNSVGGGDYQAKYGG
EYLDTISKLYPGLLLDSNGQKIDLSTKIKEWSAKYLNGSNIPQVGMGYVLKD
WNNGQYFHILDKEGQYSLPTQL

-continued

| | |
|---|---|
| BRS-B-D2 (*L. citreum* NRRL B-742) | MASQYVEKDGQFVYIDQSGKQVSGLQNIEGHTQYFDPKTGYQTKGELKNID DNAYYFDKNSGNGRTFTKISNGSYSEKDGMWQYVDSHDKQPVKGLYDVE GNLQYFDLSTGNQAKHQIRSVDGVTYYFDADSGNATAFKAVTNGRYAEQT TKDKDGNETSYWAYLDNQGNAIKGLNDVNGEIQYFDEHTGEQLKGHTATV DGTTYYFEGNKGNLVSVVNTAPTGQYKINGDNVYYLDNNNEAIKGLYGIN GNLNYFDLATGIQLKGQAKNIDGIGYYFDQNNGNGEYRYSLTGPVVKDVY SQHNAVNNLSANNFKNLVDGFLTAETWYRPAQILSHGTDWVASTDKDFRP LITVWWPNKDIQVNYLKLMQQIGILDNSVVFDTNNDQLVLNKGAESAQIGI EKKVSETGNTDWLNELLFAPNGNQPSFIKQQYLWNVDSEYPGGWFQGGYL AYQNSDLTPYANTNPDYRTHNGLEFLLANDVDNSNPVVQAEQLNWLYYL MNFGQITANDSNANFDSMRIDAISFVDPQIAKKAYDLLDKMYGLTDNEAVA NQHISIVEAPKGETPITVEKQSALVESNWRDRMKQSLSKNATLDKLDPDPAI NSLEKLVADDLVNRSQSSDKDSSTIPNYSIVHAHDKDIQDTVIHIMKIVNNNP NISMSDFTMQQLQNGLKAFYEDQHQSVKKYNQYNIPSAYALLLTNKDTVP RVFYGDMYQDYGDDLDGGQYMATKSIYYNAIEQMMKARLKYVAGGQIM AVTKIKNDGINKDGTNKSGEVLTSVRFGKDIMDAQGQGTAESRNQGIGVIV SNSSGLELKNSDSITLHMGIAHKNQAYRALMLTNDKGIVNYDQDNNAPIAW TNDHGDLIFTNQMINGQSDTAVKGYLNPEVAGYLAVWVPVGANDNQDAR TVTTNQKNTDGKVLHTNAALDSKLMYEGFSNFQKMPTRGNQYANVVITKN IDLFKSWGITDFELAPQYRSSDGKDITDRFLDSIVQNGYGLSDRYDLGFKTPT KYGTDQDLRKAIERLHQAGMSVMADFVANQIYGLHADKEVVSAQHVNIN GDTKLVVDPRYGTQMTVVNSVGGGDYQAKYGGEYLDTISKLYPGLLLDSN GQKIDLSTKIKEWSAKYLNGSNIPQVGMGYVLKDWNNGQYFHILDKEGQY SLPTQLKGGRADPAFLYKVVHHHHHH |
| BRS-C (GH_Leuconostoc_fallax_KCTC3537_1) | MKQQESITRKKLYKAGKSWVVAATLFAATLFAAMGAAGATTVASADVQK DTVVVTADKNTTDKDKEPIKTAGANVVDKGVAQTTDTNTTDKKTIEVGKS VDMSATDKKVTETVKSVDTSATDKKTTEAVKPVDTNATDKKATEAVKPV DTNATDKKTTEAVKPVDTNTTDKKVTEAIKPVNTNADDKTAEPVKTISATK DTVKTIANKQKGATEEQAVITEGHYEAQGDGFVYITKDGKQLTGLQNINGN TQYFDPATGQQLKGDIKAVAGTVYYFDKNSGNARVYQKVADGTYSENNE HWQYISKVDNKPVEGLYNVQGNLQYFDMSTGNQVKNDIRSVDGVTYYFD KDSGNGSAFNALSAGEYVEKKETDAQGNQNSYWTYSGLDGNPVKGLYDIN GSLQYFDEKNGAQLKGGTATVNGVTYYFEQDKGNLISVVNSVESGQYKID NDNVYYIDNQGNTLKGLYAINGQLNYFDMSTGVQLKGASENANGVGYYF DKDKGNGQYQYSLITSTLANAFSKHNAANDYTQSSFTHTVDGFLTADTWY RPTEILKNGTTWVASTSQDLRPMITVWWPNKNVQLNYLKLMQTEGLLDSG QVYDLNSDQALLNQAAQTVQVNIEKRITKAGNSDWLNDLLYNSHGETPSF VKQQAIWNADSEYHGGWFQGGYLAYRNSDLTPYANSSYRHYTGMEFLLA NDVDNSNPIVQAEDLNWLYYLMNFGTETGNDPQANFDSIRIDAISFVDKQV AKKAYELLHDMYGLSASDAVANKHVSIVEASADQTPVTTENHDALIESYW RDTMKNSLSKDASIDSSAGSLSAMINDGNVDRANDSTTESSIFPNYTIVHAH DKDIQDAVSNVMKIVNNDPSISLDGFTMEQLEKGLSAFYADQRSAVKQYN QYNIPSAYAVMLTNKDTVPRTFYGDMYQDDGQYMANKSLYYDAIDTMMK ARLKYVSGGQTMSVTKINNANSQKSGEVLTSVRFGKGVMDATDAGSAESR TQGIGVVVSNSSGLQLNDNDKIVLHMGAAHKNQEYRALMLTINDGIKSFN NDEAPINYTDDNGDLIFDGHNIDGQENTAIRGYLNPQVAGYLAVWVPTGAK DDQDARTQPSNEKSTDGKVLHTNAALDSELIYEGFSNFQPMPTTKDEYTNV MIAKNIDLFKSWGITNFELAPQYRSSDGKNINDRFIDSLVQNGYGLSDRY DLGFETPTKYGTDQDLRTAIKTLHQAGMTVMADYVANQIYGLNTSQEVVD AQRVNSDNNAVEVRYGQHLNVVNSIGGGEYQNLYGGKYLEILNKLYPDLL VDENGNKIDIDTKIKQWSAKYLNGSNVTGLGMGYVLKDWSNGQYFNISNT DGKVMLPEQLVKHMPAVEIGTQTNYTAYISSTIRRDGLYNNMPWGVTATG QDGNEIKWERQGSTSDYNHQKVQVNRQYVDKQGVVWNLIN FDDKDLWVDSNALVTVNFTSQKPTKHFVQFGMRQGKYDGFYLSAPYKQTE SKWVASTRTHQGQLLEVVGQYTTGSGSRKVTWYLVGLDGKQVWVDSRAV GTNFSHKTNINLLINSATRNDGMYLNAPYGQKGYKRETSSRFYNEKLVTVS QQYYDNKGVIWNLITLNGKKLWVDSRAFATVIDKKVNQSLYINSRNDGMY LNAPYRAQGAKRYASTKTYTGQRVQVTLQRKDTHGVTWYLTKVDSKQLW VDSHAFAPTFTRNVSLNVKVNSSKRNDGIYLNAPYGNKKAKRIASTKAYNG KRVKASKEYKDAKGVTWYLVNLNNKQVWIDKRAF |
| Brs-D (Lb kunkei EFB6) | MNINSNERKVRFKMYKSGKQWIVAGLTTAVISIAVYGGSSIANGGIEAKAD AQNAATSSIVNTNNSTNSSNANSIASLPQNGTYSTNDNGQTWKYVSQNKDI QGLYKDNNDQLRYFNEYDGTQAKGDIVNVNNDNYYFDKDSGQGHKIDSY TGGSYSESKVNNQDGWIYKSSDNNDVKGVATVDGNIQYFDQNTGLQLKGG SAQIGGVDYYFDPNKGNLVGKVDQVVNSNDYSDNKLLDSNKNVVKGLVV NNGQLQFFDTSNGNQAKNKQVIANGITYYFDTNGNGQYLFTNTGKSAVDD FTQRNAANSVNPSDYKNVVDGFFTADTWYRPKQILDNGTTWRNSNSNELR PMITAWWPNKDVQVNYLKLMQNNGLLDKSNSYSIQSDQQTLNQAAQKAQ VNIEKKISQTGNTDWLNDLLFKGNGDNPSFVKQQYIWSSDSESPWQGDAWF QGGYLKYGNSVMTPNTNSNYRDSNNLFDFLLANDVDNSNPAVQAEDLNW LYYLTNFGTITANDSNANFDSIRIDAVDFISNDIIQRSYDYLRQKFNLMQSDA NADSHISLVEGGVDAGTTSYSNDGLVEAPFRLDAYPLLHKQDGDVFKNLID EEDSGIDISNHNGETNTNNTIGGITLSGGKPNYSIVHAHDKDVQEKVGQAIID TTGIKDWTDFTPSQLAQGLETFYNDQRQTVKKYNDYNVPSAYAIMLINKG TVPRIYYGDMYQDDGQFMQKKSLYYDDIANLMTARKKYVSGGQSMVDNN GILTSVRFGKGANTVSDSGTEDTRNQGIGLIVGSAPKKVLNDGDTVVLHMG |

-continued

| | |
|---|---|
| | AAHKNQKYRALMLTTENGIQNYNSDDNAPVAETDDNGDLVFSNKDINGQA<br>NTAIKQVANPEVNGYLAAWVPVGASDDQDSRTAPSTSQNNDGNVLHENDA<br>LDSNLIFEGFSNFQPTPTNHDEYANVVIAKNASLFKDWGVTSFEMAPQYRSS<br>QDHTFVDSTIDNGYAFSDRYDLGFGTPTKYGTDEDLRNAIKSLHDNGMQV<br>MADVVYNQLYNLPGQEVVSATRAGVTGNTNALPFGTQLYVVNTIGGGDY<br>QKKYGGAFLNELQEQYPSLFKSQKYKYYYKNYANNGAGPGYLTVNDAER<br>SDIPYNQPITEWSAKYMNGTNILGRGMGYVLKDWNTGDYFKLSGSDSTLPS<br>SLTYKSGWVENPDSTWSYYEKNNIDKLTGSQVINEERVFFDNNGIQVKGGW<br>VKNSNGTYSYYDKNSGNILTGDQLIDGEHFFFDNNGVQVKGKWIKNSDGS<br>KSYYDSHLGKLIKTDKKVSSNARKKKSKEELLYENALKVLRKDKKRLDKN<br>KTKANIRKYNKSLKKYRKAKKKLLAITKNRVANARKAIKIAKKVLSKRKNI<br>NNEKRYYKALKEYYVAEKSYLKITGNYNKKYYYEFDKLTPKVKVVKNIYS<br>YKSRHFTKKNRVKKIKKGTLVRVKSIVRSGKVARINIGNGHFITSSKDFIKMF<br>K |
| GBD-CD2<br>(*L. citreum*<br>NRRL B-1299<br>(tronqué<br>depuis DSR-E) | AQAGHYITKNGNDWQYDTNGELAKGLRQDSNGKLRYFDLTTGIQAKGQFV<br>TIGQETYYFSKDHGDAQLLPMVTEGHYGTITLKQGQDTKTAWVYRDQNNT<br>ILKGLQNINGTLQFFDPYTGEQLKGGVAKYDDKLFYFESGKGNLVSTVAGD<br>YQDGHYISQDGQTRYADKQNQLVKGLVTVNGALQYFDNATGNQIKNQQVI<br>VDGKTYYFDDKGNGEYLFTNTLDMSTNAFSTKNVAFNHDSSSFDHTVDGF<br>LTADTWYRPKSILANGTTWRDSTDKDMRPLITVWWPNKNVQVNYLNFMK<br>ANGLLTTAAQYTLHSDQYDLNQAAQDVQVAIERRIASEHGTDWLQKLLFES<br>QNNNPSFVKQQFIWNKDSEYHGGGDAWFQGGYLKYGNNPLTPTTNSDYR<br>QPGNAFDFLLANDVDNSNPVVQAENLNWLHYLMNFGTITAGQDDANFDSI<br>RIDAVDFIHNDTIQRTYDYLRDAYQVQQSEAKANQHISLVEAGLDAGTSTIH<br>NDALIESNLREAATLSLTNEPGKNKPLTNMLQDVDGGTLITDHTQNSTENQ<br>ATPNYSIIHAHDKGVQEKVGAAITDATGADWTNFTDEQLKAGLELFYKD<br>QRATNKKYNSYNIPSIYALMLTNKDTVPRMYYGDMYQDDGQYMANKSIY<br>YDALVSLMTARKSYVSGGQTMSVDNHGLLKSVRFGKDAMTANDLGTSAT<br>RTEGLGVIIGNDPKLQLNDSDKVTLDMGAAHKNQKYRAVILTTRDGLATFN<br>SDQAPTAWTNDQGTLTFSNQEINGQDNTQIRGVANPQVSGYLAVWVPVG<br>ASDNQDARTAATTTENHDGKVLHSNAALDSNLIYEGFSNFQPKATTHDELT<br>NVVIAKNADVFNNWGITSFEMAPQYRSSGDHTFLDSTIDNGYAFTDRYDLG<br>FNTPTKYGTDGDLRATIQALHHANMQVMADVVDNQVYNLPGKEVVSATR<br>AGVYGNDDATGFGTQLYVTNSVGGGQYQEKYAGQYLEALKAKYPDLFEG<br>KAYDYWYKNYANDGSNPYYTLSHGDRESIPADVAIKQWSAKYMNGTNVL<br>GNGMGYVLKDWHNGQYFKLDGDKSTLPQIKGELKLEGKPIPNPLLGLDSTR<br>TGHHHHHH |

Table 2 presents some mutants of BRS-B-D2 that were used in the context of the present invention.

| Mutant | Sequence |
|---|---|
| M6 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGAFQGGYLAYQNSDLTPYANTNPDYRTHNGIKVLLANDVDNSNPVVQAEQL<br>NWLYYLMNFGQITANDSNANFDSMRIDGLAFVDPQIAKKAYDLLDKMYGLTDNE<br>AVANQHISIVEAPKGETPITVEKQSALVESNWIDRMLQSLSKNATLDKLDPDPAINS<br>LEKLVADDLVNRSQSSDKDSSTIPNYSIVHAHDLLLVDTVIHIMKIVNNNPNISMSDF<br>TMQQLQNGLKAFYEDQHQSVKKYNQYNIPSAYALLLTNKDTVPRVFYGDMYQDY<br>GDDLDGGQYMATKSIYYNAIEQMMKARLKYVAGGQIMAVTKIKNDGINKDGTNK<br>SGEVLTSVRFGKDIMDAQGQGTAESRNQGIGVIVSNSSGLELKNSDSITLHMGIAHK<br>NQAYRALMLTNDKGIVNYDQDNNAPIAWTNDHGDLIFTNQMINGQSDTAVKGYL<br>NPEVAGYLAVWVPVGANDNQDARTVTTNQKNTDGKVLHTNAALDSKLMYEGFS<br>NFQKMPTRGNQYANVVITKNIDLFKSWGITDFELAPQYRSSDGKDITDRFLDSIVQN<br>GYGLSDRYDLGFKTPTKYGTDQDLRKAIERLHQAGMSVMADFVANQIYGLHADK<br>EVVSAQHVNINGDTKLVVDPRYGTQMTVVNSVGGGDYQAKYGGEYLDTISKLYP<br>GLLLDSNGQKIDLSTKIKEWSAKYLNGSNIPQVGMGYVLKDWNNGQYFHILDKEG<br>QYSLPTQLKGGRADPAFLYKVVHHHHHH |
| M14 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGMMQGGYLAYQNSDLTPYANTNPDYRTHNGVKFMLANDVDNSNPVVQAEQ |

-continued

| Mutant | Sequence |
|---|---|
| | LNWLYYLMNFGQITANDSNANFDSMRIDGMWLVDPQIAKKAYDLLDKMYGLTDN |
| | EAVANQHISIVEAPKGETPITVEKQSALVESNWVDRMLQSLSKNATLDKLDPDPAIN |
| | SLEKLVADDLVNRSQSSDKDSSTIPNYSIVHAHDLNLVDTVIHIMKIVNNNPNISMS |
| | DFTMQQLQNGLKAFYEDQHQSVKKYNQYNIPSAYALLLTNKDTVPRVFYGDMYQ |
| | DYGDDLDGGQYMATKSIYYNAIEQMMKARLKYVAGGQIMAVTKIKNDGINKDGT |
| | NKSGEVLTSVRFGKDIMDAQGQGTAESRNQGIGVIVSNSSGLELKNSDSITLHMGIA |
| | HKNQAYRALMLTNDKGIVNYDQDNNAPIAWTNDHGDLIFTNQMINGQSDTAVKG |
| | YLNPEVAGYLAVWVPVGANDNQDARTVTTNQKNTDGKVLHTNAALDSKLMYEG |
| | FSNFQKMPTRGNQYANVVITKNIDLFKSWGITDFELAPQYRSSDGKDITDRFLDSIV |
| | QNGYGLSDRYDLGFKTPTKYGTDQDLRKAIERLHQAGMSVMADFVANQIYGLHA |
| | DKEVVSAQHVNINGDTKLVVDPRYGTQMTVVNSVGGGDYQAKYGGEYLDTISKL |
| | YPGLLLDSNGQKIDLSTKIKEWSAKYLNGSNIPQVGMGYVLKDWNNGQYFHILDK |
| | EGQYSLPTQLKGGRADPAFLYKVVHHHHHH |
| M18 | MASQYVEKDGQFVYIDQSGKQVSGLQNIEGHTQYFDPKTGYQTKGELKNIDDNAY |
| | YFDKNSGNGRTFTKISNGSYSEKDGMWQYVDSHDKQPVKGLYDVEGNLQYFDLS |
| | TGNQAKHQIRSVDGVTYYFDADSGNATAFKAVTNGRYAEQTTKDKDGNETSYWA |
| | YLDNQGNAIKGLNDVNGEIQYFDEHTGEQLKGHTATVDGTTYYFEGNKGNLVSVV |
| | NTAPTGQYKINGDNVYYLDNNNEAIKGLYGINGNLNYFDLATGIQLKGQAKNIDGI |
| | GYYFDQNNGNGEYRYSLTGPVVKDVYSQHNAVNNLSANNFKNLVDGFLTAETWY |
| | RPAQILSHGTDWVASTDKDFRPLITVWWPNKDIQVNYLKLMQQIGILDNSVVFDTN |
| | NDQLVLNKGAESAQIGIEKKVSETGNTDWLNELLFAPNGNQPSFIKQQYLWNVDSE |
| | YPGGLFQGGYLAYQNSDLTPYANTNPDYRTHNGIRYLLANDVDNSNPVVQAEQLN |
| | WLYYLMNFGQITANDSNANFDSMRIDAPDWVDPQIAKKAYDLLDKMYGLTDNEA |
| | VANQHISIVEAPKGETPITVEKQSALVESNWIDRMLQSLSKNATLDKLDPDPAINSLE |
| | KLVADDLVNRSQSSDKDSSTIPNYSIVHAHDINVLDTVIHIMKIVNNNPNISMSDFT |
| | MQQLQNGLKAFYEDQHQSVKKYNQYNIPSAYALLLTNKDTVPRVFYGDMYQDYG |
| | DDLDGGQYMATKSIYYNAIEQMMKARLKYVAGGQIMAVTKIKNDGINKDGTNKS |
| | GEVLTSVRFGKDIMDAQGQGTAESRNQGIGVIVSNSSGLELKNSDSITLHMGIAHKN |
| | QAYRALMLTNDKGIVNYDQDNNAPIAWTNDHGDLIFTNQMINGQSDTAVKGYLN |
| | PEVAGYLAVWVPVGANDNQDARTVTTNQKNTDGKVLHTNAALDSKLMYEGFSN |
| | FQKMPTRGNQYANVVITKNIDLFKSWGITDFELAPQYRSSDGKDITDRFLDSIVQNG |
| | YGLSDRYDLGFKTPTKYGTDQDLRKAIERLHQAGMSVMADFVANQIYGLHADKE |
| | VVSAQHVNINGDTKLVVDPRYGTQMTVVNSVGGGDYQAKYGGEYLDTISKLYPG |
| | LLLDSNGQKIDLSTKIKEWSAKYLNGSNIPQVGMGYVLKDWNNGQYFHILDKEGQ |
| | YSLPTQLKGGRADPAFLYKVVHHHHHH |
| M21 | MASQYVEKDGQFVYIDQSGKQVSGLQNIEGHTQYFDPKTGYQTKGELKNIDDNAY |
| | YFDKNSGNGRTFTKISNGSYSEKDGMWQYVDSHDKQPVKGLYDVEGNLQYFDLS |
| | TGNQAKHQIRSVDGVTYYFDADSGNATAFKAVTNGRYAEQTTKDKDGNETSYWA |
| | YLDNQGNAIKGLNDVNGEIQYFDEHTGEQLKGHTATVDGTTYYFEGNKGNLVSVV |
| | NTAPTGQYKINGDNVYYLDNNNEAIKGLYGINGNLNYFDLATGIQLKGQAKNIDGI |
| | GYYFDQNNGNGEYRYSLTGPVVKDVYSQHNAVNNLSANNFKNLVDGFLTAETWY |
| | RPAQILSHGTDWVASTDKDFRPLITVWWPNKDIQVNYLKLMQQIGILDNSVVFDTN |
| | NDQLVLNKGAESAQIGIEKKVSETGNTDWLNELLFAPNGNQPSFIKQQYLWNVDSE |
| | YPGGLFQGGYLAYQNSDLTPYANTNPDYRTHNGLEFLLANDVDNSNPVVQAEQLN |
| | WLYYLMNFGQITANDSNANFDSMRIDAIDFVDPQIAKKAYDLLDKMYGLTDNEAV |
| | ANQHISIVEADKGETPITVEKQSALVESNWWLRMKQSLSKNATLDKLDPDPAINSL |
| | EKLVADDLVNRSQSSDKDSSTIPNYSIVHAHDLDIQETVVHIMKIVNNNPNISWTDF |
| | TMQQLQNGLKAFYEDQHQSVKKYNQYNIPSAYALLLTNKDTVPRVFYGDMYQDY |
| | GDDLDGGQYMATKSIYYNAIEQMMKARLKYVAGGQIMAVTKIKNDGINKDGTNK |
| | SGEVLTSVRFGKDIMDAQGQGTAESRNQGIGVIVSNSSGLELKNSDSITLHMGIAHK |
| | NQAYRALMLTNDKGIVNYDQDNNAPIAWTNDHGDLIFTNQMINGQSDTAVKGYL |
| | NPEVAGYLAVWVPVGANDNQDARTVTTNQKNTDGKVLHTNAALDSKLMYEGFS |
| | NFQKMPTRGNQYANVVITKNIDLFKSWGITDFELAPQYRSSDGKDITDRFLDSIVQN |
| | GYGLSDRYDLGFKTPTKYGTDQDLRKAIERLHQAGMSVMADFVANQIYGLHADK |
| | EVVSAQHVNINGDTKLVVDPRYGTQMTVVNSVGGGDYQAKYGGEYLDTISKLYP |
| | GLLLDSNGQKIDLSTKIKEWSAKYLNGSNIPQVGMGYVLKDWNNGQYFHILDKEG |
| | QYSLPTQLKGGRADPAFLYKVVHHHHHH |
| M23 | MASQYVEKDGQFVYIDQSGKQVSGLQNIEGHTQYFDPKTGYQTKGELKNIDDNAY |
| | YFDKNSGNGRTFTKISNGSYSEKDGMWQYVDSHDKQPVKGLYDVEGNLQYFDLS |
| | TGNQAKHQIRSVDGVTYYFDADSGNATAFKAVTNGRYAEQTTKDKDGNETSYWA |
| | YLDNQGNAIKGLNDVNGEIQYFDEHTGEQLKGHTATVDGTTYYFEGNKGNLVSVV |
| | NTAPTGQYKINGDNVYYLDNNNEAIKGLYGINGNLNYFDLATGIQLKGQAKNIDGI |
| | GYYFDQNNGNGEYRYSLTGPVVKDVYSQHNAVNNLSANNFKNLVDGFLTAETWY |
| | RPAQILSHGTDWVASTDKDFRPLITVWWPNKDIQVNYLKLMQQIGILDNSVVFDTN |
| | NDQLVLNKGAESAQIGIEKKVSETGNTDWLNELLFAPNGNQPSFIKQQYLWNVDSE |
| | YPGGPFQGGYLAYQNSDLTPYANTNPDYRTHNGLEFLLANDVDNSNPVVQAEQLN |
| | WLYYLMNFGQITANDSNANFDSMRIDAIMFVDPQIAKKAYDLLDKMYGLTDNEA |
| | VANQHISIVEADKGETPITVEKQSALVESNWLLRMKQSLSKNATLDKLDPDPAINSL |
| | EKLVADDLVNRSQSSDKDSSTIPNYSIVHAHDKDILETVTHIMKIVNNNPNISDTDFT |
| | MQQLQNGLKAFYEDQHQSVKKYNQYNIPSAYALLLTNKDTVPRVFYGDMYQDYG |
| | DDLDGGQYMATKSIYYNAIEQMMKARLKYVAGGQIMAVTKIKNDGINKDGTNKS |
| | GEVLTSVRFGKDIMDAQGQGTAESRNQGIGVIVSNSSGLELKNSDSITLHMGIAHKN |
| | QAYRALMLTNDKGIVNYDQDNNAPIAWTNDHGDLIFTNQMINGQSDTAVKGYLN |
| | PEVAGYLAVWVPVGANDNQDARTVTTNQKNTDGKVLHTNAALDSKLMYEGFSN |

-continued

| Mutant | Sequence |
|---|---|
| | FQKMPTRGNQYANVVITKNIDLFKSWGITDFELAPQYRSSDGKDITDRFLDSIVQNG<br>YGLSDRYDLGFKTPTKYGTDQDLRKAIERLHQAGMSVMADFVANQIYGLHADKE<br>VVSAQHVNINGDTKLVVDPRYGTQMTVVNSVGGGDYQAKYGGEYLDTISKLYPG<br>LLLDSNGQKIDLSTKIKEWSAKYLNGSNIPQVGMGYVLKDWNNGQYFHILDKEGQ<br>YSLPTQLKGGRADPAFLYKVVHHHHHH |
| M28 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGMFQGGYLAYQNSDLTPYANTNPDYRTHNGLEFLLANDVDNSNPVVQAEQL<br>NWLYYLMNFGQITANDSNANFDSMRIDAIMFVDPQIAKKAYDLLDKMYGLTDNE<br>AVANQHISIVEDSKGETPITVEKQSALVESNWWLRMKQSLSKNATLDKLDPDPAIN<br>SLEKLVADDLVNRSQSSDKDSSTIPNYSIVHAHDLDILETVVHIMKIVNNNPNISWT<br>DFTMQQLQNGLKAFYEDQHQSVKKYNQYNIPSAYALLLTNKDTVPRVFYGDMYQ<br>DYGDDLDGGQYMATKSIYYNAIEQMMKARLKYVAGGQIMAVTKIKNDGINKDGT<br>NKSGEVLTSVRFGKDIMDAQGQGTAESRNQGIGVIVSNSSGLELKNSDSITLHMGIA<br>HKNQAYRALMLTNDKGIVNYDQDNNAPIAWTNDHGDLIFTNQMINGQSDTAVKG<br>YLNPEVAGYLAVWVPVGANDNQDARTVTTNQKNTDGKVLHTNAALDSKLMYEG<br>FSNFQKMPTRGNQYANVVITKNIDLFKSWGITDFELAPQYRSSDGKDITDRFLDSIV<br>QNGYGLSDRYDLGFKTPTKYGTDQDLRKAIERLHQAGMSVMADFVANQIYGLHA<br>DKEVVSAQHVNINGDTKLVVDPRYGTQMTVVNSVGGGDYQAKYGGEYLDTISKL<br>YPGLLLDSNGQKIDLSTKIKEWSAKYLNGSNIPQVGMGYVLKDWNNGQYFHILDK<br>EGQYSLPTQLKGGRADPAFLYKVVHHHHHH |
| M30 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGLFQGGYLAYQNSDLTPYANTNPDYRTHNGLEFLLANDVDNSNPVVQAEQLN<br>WLYYLMNFGQITANDSNANFDSMRIDAISWVDPQIAKKAYDLLDKMYGLTDNEA<br>VANQHISIVEALKGETPITVEKQSALVESNWMQRMKQSLSKNATLDKLDPDPAINS<br>LEKLVADDLVNRSQSSDKDSSTIPNYSIVHAHDVDIVETVTHIMKIVNNNPNISMTD<br>FTMQQLQNGLKAFYEDQHQSVKKYNQYNIPSAYALLLTNKDTVPRVFYGDMYQD<br>YGDDLDGGQYMATKSIYYNAIEQMMKARLKYVAGGQIMAVTKIKNDGINKDGTN<br>KSGEVLTSVRFGKDIMDAQGQGTAESRNQGIGVIVSNSSGLELKNSDSITLHMGIAH<br>KNQAYRALMLTNDKGIVNYDQDNNAPIAWTNDHGDLIFTNQMINGQSDTAVKGY<br>LNPEVAGYLAVWVPVGANDNQDARTVTTNQKNTDGKVLHTNAALDSKLMYEGF<br>SNFQKMPTRGNQYANVVITKNIDLFKSWGITDFELAPQYRSSDGKDITDRFLDSIVQ<br>NGYGLSDRYDLGFKTPTKYGTDQDLRKAIERLHQAGMSVMADFVANQIYGLHAD<br>KEVVSAQHVNINGDTKLVVDPRYGTQMTVVNSVGGGDYQAKYGGEYLDTISKLY<br>PGLLLDSNGQKIDLSTKIKEWSAKYLNGSNIPQVGMGYVLKDWNNGQYFHILDKE<br>GQYSLPTQLKGGRADPAFLYKVVHHHHHH |
| M31 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVINGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGLFQGGYLAYQNSDLTPYANTNPDYRTHNGLEFLLANDVDNSNPVVQAEQLN<br>WLYYLMNFGQITANDSNANFDSMRIDAISWVDPQIAKKAYDLLDKMYGLTDNEA<br>VANQHISIVEALKGETPITVEKQSALVESNWMERMKQSLSKNATLDKLDPDPAINSL<br>EKLVADDLVNRSQSSDKDSSTIPNYSIVHAHDIDIILTVWHIMKIVNNNPNISVTDFT<br>MQQLQNGLKAFYEDQHQSVKKYNQYNIPSAYALLLTNKDTVPRVFYGDMYQDYG<br>DDLDGGQYMATKSIYYNAIEQMMKARLKYVAGGQIMAVTKIKNDGINKDGTNKS<br>GEVLTSVRFGKDIMDAQGQGTAESRNQGIGVIVSNSSGLELKNSDSITLHMGIAHKN<br>QAYRALMLTNDKGIVNYDQDNNAPIAWTNDHGDLIFTNQMINGQSDTAVKGYLN<br>PEVAGYLAVWVPVGANDNQDARTVTTNQKNTDGKVLHTNAALDSKLMYEGFSN<br>FQKMPTRGNQYANVVITKNIDLFKSWGITDFELAPQYRSSDGKDITDRFLDSIVQNG<br>YGLSDRYDLGFKTPTKYGTDQDLRKAIERLHQAGMSVMADFVANQIYGLHADKE<br>VVSAQHVNINGDTKLVVDPRYGTQMTVVNSVGGGDYQAKYGGEYLDTISKLYPG<br>LLLDSNGQKIDLSTKIKEWSAKYLNGSNIPQVGMGYVLKDWNNGQYFHILDKEGQ<br>YSLPTQLKGGRADPAFLYKVVHHHHHH |

-continued

| Mutant | Sequence |
|---|---|
| M34 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGLFQGGYLAYQNSDLTPYANTNPDYRTHNGLEFLLANDVDNSNPVVQAEQLN<br>WLYYLMNFGQITANDSNANFDSMRIDAISWVDPQIAKKAYDLLDKMYGLTDNEA<br>VANQHISIVEALKGETPITVEKQSALVESNWMARMKQSLSKNATLDKLDPDPAINS<br>LEKLVADDLVNRSQSSDKDSSTIPNYSIVHAHDVDILETVVHIMKIVNNNPNISPTDF<br>TMQQLQNGLKAFYEDQHQSVKKYNQYNIPSAYALLLTNKDTVPRVFYGDMYQDY<br>GDDLDGGQYMATKSIYYNAIEQMMKARLKYVAGGQIMAVTKIKNDGINKDGTNK<br>SGEVLTSVRFGKDIMDAQGQGTAESRNQGIGVIVSNSSGLELKNSDSITLHMGIAHK<br>NQAYRALMLTNDKGIVNYDQDNNAPIAWTNDHGDLIFTNQMINGQSDTAVKGYL<br>NPEVAGYLAVWVPVGANDNQDARTVTTNQKNTDGKVLHTNAALDSKLMYEGFS<br>NFQKMPTRGNQYANVVITKNIDLFKSWGITDFELAPQYRSSDGKDITDRFLDSIVQN<br>GYGLSDRYDLGFKTPTKYGTDQDLRKAIERLHQAGMSVMADFVANQIYGLHADK<br>EVVSAQHVNINGDTKLVVDPRYGTQMTVVNSVGGGDYQAKYGGEYLDTISKLYP<br>GLLLDSNGQKIDLSTKIKEWSAKYLNGSNIPQVGMGYVLKDWNNGQYFHILDKEG<br>QYSLPTQLKGGRADPAFLYKVVHHHHHH |
| M35 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGAFQGGYLAYQNSDLTPYANTNPDYRTHNGLEFMLANDVDNSNPVVQAEQL<br>NWLYYLMNFGQITANDSNANFDSMRIDAISFVDPQIAKKAYDLLDKMYGLTDNEA<br>VANQHISIVEAPKGETPITVEKQSALVESNWRDRMKQSLSKNATLDKLDPDPAINSL<br>EKLVADDLVNRSQSSDKDSSTIPNYSIVHAHDADVQVTVIGTMKIVNNNPNISHTDF<br>TMQQLQNGLKAFYEDQHQSVKKYNQYNIPSAYALLLTNKDTVPRVFYGDMYQDY<br>GDDLDGGQYMATKSIYYNAIEQMMKARLKYVAGGQIMAVTKIKNDGINKDGTNK<br>SGEVLTSVRFGKDIMDAQGQGTAESRNQGIGVIVSNSSGLELKNSDSITLHMGIAHK<br>NQAYRALMLTNDKGIVNYDQDNNAPIAWTNDHGDLIFTNQMINGQSDTAVKGYL<br>NPEVAGYLAVWVPVGANDNQDARTVTTNQKNTDGKVLHTNAALDSKLMYEGFS<br>NFQKMPTRGNQYANVVITKNIDLFKSWGITDFELAPQYRSSDGKDITDRFLDSIVQN<br>GYGLSDRYDLGFKTPTKYGTDQDLRKAIERLHQAGMSVMADFVANQIYGLHADK<br>EVVSAQHVNINGDTKLVVDPRYGTQMTVVNSVGGGDYQAKYGGEYLDTISKLYP<br>GLLLDSNGQKIDLSTKIKEWSAKYLNGSNIPQVGMGYVLKDWNNGQYFHILDKEG<br>QYSLPTQLKGGRADPAFLYKVVHHHHHH |
| M40 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN<br>NDQLVLNKGAESAQIGIEKKVSETGNTDWLNELLFAPNGNQPSFIKQQYLWNVDSE<br>YPGGDFQGGYLAYQNSDLTPYANTNPDYRTHNGLEFLMANDVDNSNPVVQAEQL<br>NWLYYLMNFGQITANDSNANFDSMRIDAISFVDPQIAKKAYDLLDKMYGLTDNEA<br>VANQHISIVEAPKGETPITVEKQSALVESNWRDRMKQSLSKNATLDKLDPDPAINSL<br>EKLVADDLVNRSQSSDKDSSTIPNYSIVHAHDVDITITVVSLMKIVNNNPNISSTDFT<br>MQQLQNGLKAFYEDQHQSVKKYNQYNIPSAYALLLTNKDTVPRVFYGDMYQDYG<br>DDLDGGQYMATKSIYYNAIEQMMKARLKYVAGGQIMAVTKIKNDGINKDGTNKS<br>GEVLTSVRFGKDIMDAQGQGTAESRNQGIGVIVSNSSGLELKNSDSITLHMGIAHKN<br>QAYRALMLTNDKGIVNYDQDNNAPIAWTNDHGDLIFTNQMINGQSDTAVKGYLN<br>PEVAGYLAVWVPVGANDNQDARTVTTNQKNTDGKVLHTNAALDSKLMYEGFSN<br>FQKMPTRGNQYANVVITKNIDLFKSWGITDFELAPQYRSSDGKDITDRFLDSIVQNG<br>YGLSDRYDLGFKTPTKYGTDQDLRKAIERLHQAGMSVMADFVANQIYGLHADKE<br>VVSAQHVNINGDTKLVVDPRYGTQMTVVNSVGGGDYQAKYGGEYLDTISKLYPG<br>LLLDSNGQKIDLSTKIKEWSAKYLNGSNIPQVGMGYVLKDWNNGQYFHILDKEGQ<br>YSLPTQLKGGRADPAFLYKVVHHHHHH |
| M41 | MASQYVEKDGQFVYIDQSGKQVSGLQNIEGHTQYFDPKTGYQTKGELKNIDDNAY<br>YFDKNSGNGRTFTKISNGSYSEKDGMWQYVDSHDKQPVKGLYDVEGNLQYFDLS<br>TGNQAKHQIRSVDGVTYYFDADSGNATAFKAVTNGRYAEQTTKDKDGNETSYWA<br>YLDNQGNAIKGLNDVNGEIQYFDEHTGEQLKGHTATVDGTTYYFEGNKGNLVSVV<br>NTAPTGQYKINGDNVYYLDNNNEAIKGLYGINGNLNYFDLATGIQLKGQAKNIDGI<br>GYYFDQNNGNGEYRYSLTGPVVKDVYSQHNAVNNLSANNFKNLVDGFLTAETWY<br>RPAQILSHGTDWVASTDKDFRPLITVWWPNKDIQVNYLKLMQQIGILDNSVVFDTN |

-continued

| Mutant | Sequence |
|---|---|
| | NDQLVLNKGAESAQIGIEKKVSETGNTDWLNELLFAPNGNQPSFIKQQYLWNVDSE<br>YPGGLMQGGYLAYQNSDLTPYANTNPDYRTHNGLEFLLANDVDNSNPVVQAEQL<br>NWLYYLMNFGQITANDSNANFDSMRIDAISFVDPQIAKKAYDLLDKMYGLTDNEA<br>VANQHISIVEAPKGETPITVEKQSALVESNWRDRMKQSLSKNATLDKLDPDPAINSL<br>EKLVADDLVNRSQSSDKDSSTIPNYSIVHAHDLDLEDTVVSLMKIVNNNPNISMTDF<br>TMQQLQNGLKAFYEDQHQSVKKYNQYNIPSAYALLLTNKDTVPRVFYGDMYQDY<br>GDDLDGGQYMATKSIYYNAIEQMMKARLKYVAGGQIMAVTKIKNDGINKDGTNK<br>SGEVLTSVRFGKDIMDAQGQGTAESRNQGIGVIVSNSSGLELKNSDSITLHMGIAHK<br>NQAYRALMLINDKGIVNYDQDNNAPIAWTNDHGDLIFTNQMINGQSDTAVKGYL<br>NPEVAGYLAVWVPVGANDNQDARTVTTNQKNTDGKVLHTNAALDSKLMYEGFS<br>NFQKMPTRGNQYANVVITKNIDLFKSWGITDFELAPQYRSSDGKDITDRFLDSIVQN<br>GYGLSDRYDLGFKTPTKYGTDQDLRKAIERLHQAGMSVMADFVANQIYGLHADK<br>EVVSAQHVNINGDTKLVVDPRYGTQMTVVNSVGGGDYQAKYGGEYLDTISKLYP<br>GLLLDSNGQKIDLSTKIKEWSAKYLNGSNIPQVGMGYVLKDWNNGQYFHILDKEG<br>QYSLPTQLKGGRADPAFLYKVVHHHHHH |

Isolation of brsE Gene

The brsE gene was identified in *Leuconostoc mesenteroides* KFRI-MG genome (NCBI Reference Sequence: CP000574) by performing a nucleotide BLAST against a GH70 α-transglucosylase encoding gene database. The protein sequence of BRS-E is deposited under the GenBank accession number AHF19404.1.

Recombinant Expression of BRS-E in *E. coli*

A synthetic brsE gene was designed in order to optimize its expression in *E. coli* (Biomatik, Cambridge, ON, Canada), and cloned in pET28b vector.

The gene was then amplified by PCR from pET28b/BrsE plasmid DNA template using the forward primer 5'-atgggctacaaggccgg-3' and the reverse primer 5'-accataataatacaccttattatcggc-3'. The PCR product was then inserted into the pENTR/D-TOPO vector (Life Technologies). From a positive entry clone, LR recombination (Gateway LR Clonase II enzyme mix, Life technologies) was performed with pET-55-DEST destination vector (Merck Millipore). Expression clones were selected on LB agar plates supplemented with 100 μg ml-1 of ampicillin. Plasmids were then extracted using the GenElute HP Plasmid Miniprep kit (Sigma-Aldrich), verified by restriction analyses and sequenced (GATC Biotech). *E. coli* TOP10 competent cells (Life Technologies) were used for all cloning experiments.

For enzyme production, *E. coli* BL21*DE3 cells were freshly transformed by 55/brsE. Twenty milliliters of LB medium, supplemented with ampicillin (100 μg $mL^{-1}$), were inoculated with 100 μL of transformation mix and incubated overnight at 37° C. under agitation (200 rpm). Then, Erlenmeyer flasks culture containing a modified ZYM5052 medium with 100 μg mL ampicillin, 0.1% lactose, 0% glucose and 1% glycerol were inoculated with the starter culture at an OD600 nm of 0.05. Cultures were incubated at 21° C. under agitation (150 rpm). After 26-hour incubation, cells were harvested by centrifugation, dispersed in 50 mM sodium acetate buffer (pH 5.75) at a final OD600 nm of 80 and disrupted by sonication. The recombinant enzymes were recovered in the soluble fraction after centrifugation (11,000 g, 30 min, 8° C.) of the crude cell extract.

Enzyme Production

Cloning of branching sucrase genes in inducible vectors (pET53, pET55 or pBAD49, Life technologies) for heterologous expression in *E. coli* cells was previously described (Vuillemin et al., J Biol Chem. 2016; 291(14):7687-702). *E. coli* BL21*DE3 and *E. coli* BL21 AI cells were freshly transformed by pET53-55/brsB Δ2, brsC, brsD, brsE and pBAD49/brsA, respectively. Twenty milliliters of LB medium, supplemented with ampicillin (100 g $mL^{-1}$), were inoculated with 100 μL of transformation mix and incubated overnight at 37° C. under agitation (200 rpm).

Enzyme production were performed in Erlenmeyer flasks with modified ZYM5052 medium that contains i) 0% lactose, 0% glucose, 0.5% glycerol and 0.01% L-arabinose for BRS-A production, ii) 0.1% lactose, 0% glucose and 1% glycerol for BRS-B-Δ2, BRS-C, BRS-D, BRS-E production or iii) 0.75% lactose, 0.05% glucose and 1.5% glycerol for GBD-CD2 (wild type and mutants) production. All culture media were supplemented with ampicillin (100 μg $mL^{-1}$) and inoculated with the corresponding starter culture at an $OD_{600\ nm}$ of 0.05. Cultures were incubated at 21° C. or 23° C. under agitation (150 rpm). After 26-hour incubation, cells were harvested by centrifugation, dispersed in 50 mM sodium acetate buffer (pH 5.75) at a final $OD_{600\ nm}$ of 80 for BRS-A, BRS-B-A2, BRS-C, BRS-D, BRS-E, and an $OD_{600\ nm}$ of 30 for GBD-CD2 and mutants. Cells were disrupted by sonication. The recombinant enzymes were recovered in the soluble fraction after centrifugation (11,000 g, 30 min, 8° C.) of the crude cell extract.

Enzyme Purification by Affinity Chromatography

Recombinant enzymes are produced in fusion with a 6×His tag allowing purification by affinity chromatography. For that purpose, cells were centrifuged and resuspended in binding buffer (20 mM phosphate sodium buffer, pH 7.4, 500 mM NaCl, 20 mM imidazole, 2.5% (v/v) glycerol) at a final $OD_{600\ nm}$ of 200 for BRS-B productions, and 30 for GBD-CD2 and mutants productions. After disruption by sonication, centrifugation (18,000 g, 30 min, 4° C.) and filtration through a 0.22 μm cartridge, lysates were applied at 10° C. onto a 1 ml HisTrap HP® column that had been equilibrated with the binding buffer, using an AKTAXpress system (GE Healthcare). The proteins were eluted by imidazole gradient from 10 to 500 mM, over 25 minutes. Eluate fractions of 3 mL were desalted onto 10-DG column (Biorad, Hercules, CA, USA), with 50 mM sodium acetate buffer at pH 5.75 with 100 mM NaCl, or purified for a second round by gel-filtration on a Superose12 resin.

Enzymatic Activity Assay

One unit of branching sucrase (wild-type and mutants) is defined as the amount of enzyme which catalyzes the production of one micromole of fructose per min, at 30° C., in 50 mM sodium acetate buffer at pH 5.1 or pH 5.75 depending on the enzyme, and from 292 mM sucrose. The enzyme activities were determined by measuring the amount of reducing sugars using the dinitrosalycilic acid (DNS) method (G. L. Miller, *Anal. Chem.* 1959, 31, 426-428).

Glucosylation of Tetrasaccharide Using Branching Sucrases

Transglucosylation assays were performed at a temperature between 20 to 37° C. in 50 mM sodium acetate buffer, pH 5.0 to 6.0, supplemented with 0.05 to 5 U·mL$^{-1}$ of enzyme, 50 mM to 1 M sucrose, and 10 mM to 100 mM tetrasaccharide of formula (Ia), in particular $AB_{ClAc}C_{Cl3Ac}D$-All (also referred as ABC'D'). Reactions were incubated in glass tubes for 8 to 24 h.

Specifically, the pentasaccharides were produced in the following conditions:

Pentasaccharide 1 (P1) was produced in particular by BRS-B-Δ2 in a 500 μL scale reaction using 200 μL of ABC'D' acceptor preparation at 110 g·L$^{-1}$, 206 μL of sucrose at 830 g·L$^{-1}$, 50 μL of sodium acetate buffer 500 mM at pH 5.1, 9.62 μL of purified enzyme BRS-B-Δ2 at 52 U/mL and $H_2O$ to 500 μL.

Pentasaccharides 2 (P2) and 2' (2') were produced in particular by GBD-CD2 F2163G in a 2 mL scale reaction using 800 μL of ABC'D' acceptor preparation at 110 g·L$^{-1}$, 823 μL of sucrose at 830 g·L$^{-1}$, 200 μL of sodium acetate buffer 500 mM at pH 5.1, 130.7 μL of purified enzyme GBD-CD2 F2163G at 15.3 U/mL and $H_2O$ to 2 mL.

Pentasaccharide 3 (P3) was produced in particular by GBD-CD2 W2135S-F2136L or GBD-CD2 W2135I-F2136C in a 2 mL scale reaction using 800 μL of ABC'D' acceptor preparation at 110 g·L$^{-1}$, 823 μL of sucrose at 830 g·L$^{-1}$ 200 μL of sodium acetate buffer 500 mM at pH 5.1, 130.7 μL of purified enzyme at 15.3 U/mL and $H_2O$ to 2 mL.

Methods for Separation, Detection and Purification of the Compounds of Interest:

The presence of residual acceptor ABC'D' and glucosylated products (pentasaccharides P1 and P2, P2' and P3) was determined by HPLC-MS (High performance Liquid Chromatography coupled with Mass Spectrometry) using a C18RP Fusion (4 μm, 80 Å, 250×4.6 mm) analytical column placed in an oven at 40° C. and eluting with a 20-minute $H_2O$/acetonitrile gradient from 70:30 to 60:40 at a flow of 1 mL·min$^{-1}$. Reaction media were diluted 10 times in $H_2O$/acetonitrile (70:30, v/v)+0.08% trifluoroacetic acid (TFA) before injection of 20 μL samples. UV Detection was carried out at 220 nm wavelength. The mass of the different compounds was determined by mass spectrometry with a 0.5 s full scan (m/z 200-1950) both in positive and negative modes. Needle was set on 3.5 kV, cone on 60 V, and the probe temperature was maintained at 450° C.

Pentasaccharides P1, P2, P2' and P3 were purified by automatic fractionation on an Agilent 1260 Infinity HPLC, during 20 min of separation (same method as above). Several rounds of purification were performed if necessary. Products detected by UV-RI peaks were collected, and reanalyzed by HPLC. Fractions containing single peak products were pooled, concentrated to dryness using a SpeedVac before exchange in $D_2O$ for NMR analyses.

NMR Analyses for Pentasaccharides Structure Elucidation:

The samples were dissolved in DCl-containing $D_2O$ at pH 4.9 For NMR studies, the samples were lyophilized three times and dissolved in 180 μL of 99.9% DCl-containing $D_2O$.

All NMR spectra were recorded on a Bruker Avance spectrometer operating at a proton frequency of 950 MHz and at a carbon frequency of 238 MHz with a 5-mm gradient indirect cryoprobe. All spectra were processed and analyzed with Topspin software (Bruker).

$^{1}H$ and $^{13}C$ 1D NMR spectra were accumulated at 30° C., 65536 data points were acquired with 32 and 2048 scans respectively for proton and carbon experiments.

$^{1}H$-$^{13}C$ HSQC (Heteronuclear Single Quantum Coherence spectroscopy), HMBC (Heteronuclear_single_quantum_coherence_spectroscopy) and Double Quantum Filtered COrrelation SpectroscopY (QDF COSY) experiments were performed at 30° C. Homo and heteronuclear spectra were recorded under the following experimental conditions: 512 increments of 2048 complex points are acquired with an accumulation of 16 scans. Spectral widths were 16025 Hz for proton dimension and 44267 Hz for carbon dimension.

Results

The structure of Pentasaccharide P1 was determined by NMR spectroscopy (950 MHz), revealing an α-1,6 glucosylation of D', characteristic of *S. flexneri* serotype 4a.

The structure of Pentasaccharide P2 was determined by NMR spectroscopy (950 MHz), revealing an α-1,3 glucosylation of A, characteristic of *S. flexneri* serotype 3a.

The structure of Pentasaccharides P2' and P3 were also determined by NMR spectroscopy (950 MHz), revealing respectively an α-1,4 glucosylation of residue A and an α-1,4 glucosylation of residue B.

P1

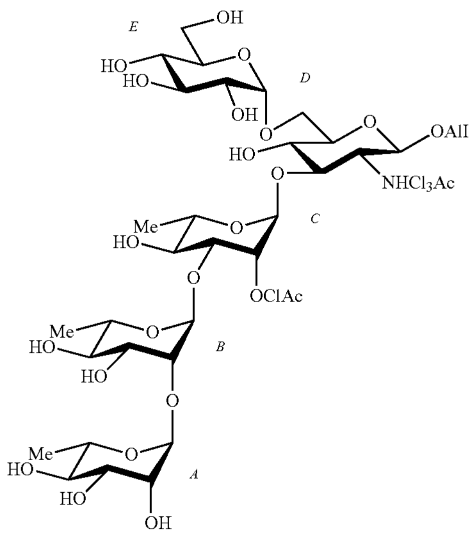

P2

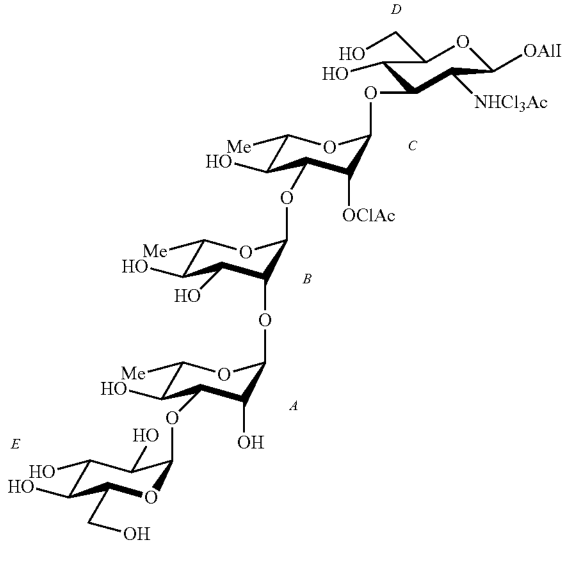

-continued

P2'

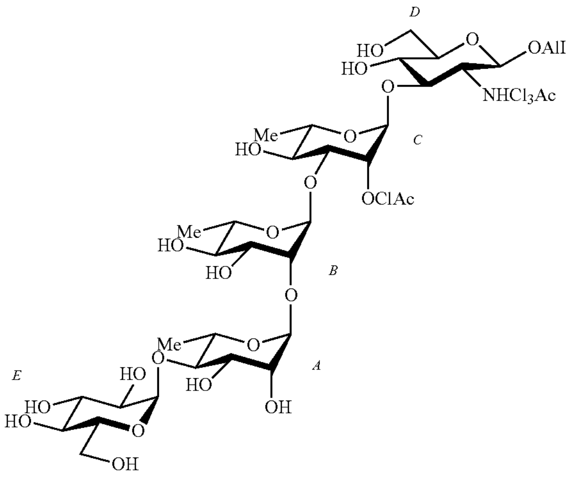

P3

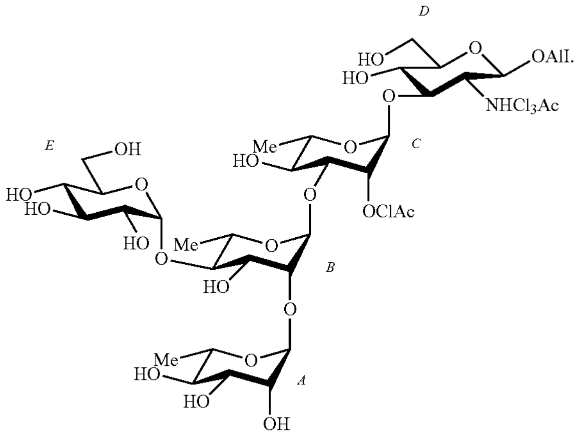

We claim:

1. A compound of one of the following formulae:

$((E1\rightarrow 2)_a(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ ClAc}C((E1\rightarrow 2)_a(E1\rightarrow 4)_a(E1\rightarrow 6)_{b\ Cl3Ac}D)_y$-All;

$((E1\rightarrow 2)_a(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_eC((E1\rightarrow 2)_a(E1\rightarrow 4)_a(E1\rightarrow 6)_{b\ Cl3Ac}D)_y$-All;

$((E1\rightarrow 2)_a(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ Ac}C((E1\rightarrow 2)_a(E1\rightarrow 4)_a(E1\rightarrow 6)_{b\ Cl3Ac}D)_y$-All;

$((E1\rightarrow 2)_a(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ Ac}C((E1\rightarrow 2)_a(E1\rightarrow 4)_a(E1\rightarrow 6)_{b\ Cl3Ac}D)_y$;

$((E1\rightarrow 2)_a(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ ClAc}C((E1\rightarrow 2)_a(E1\rightarrow 4)_a(E1\rightarrow 6)_{b\ Cl3Ac}D)_y$;

$((E1\rightarrow 2)_a(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_eC((E1\rightarrow 2)_a(E1\rightarrow 4)_a(E1\rightarrow 6)_{b\ Cl3Ac}D)_y$;

$((E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ ClAc}C((E1\rightarrow 4)_a(E1\rightarrow 6_b)_{Cl3Ac}D)_y$-All;

$((E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_eC((E1\rightarrow 4)_a(E1\rightarrow 6)_{b\ Cl3Ac}D)_y$-All;

$(E1\rightarrow 4)_a(E1\rightarrow 6)_{bCl3Ac}D)_x(E1\rightarrow 3)_c(E1\rightarrow 4)_cA(E1\rightarrow 4)_dB(E1\rightarrow 4)_{e\ Ac}C((E1\rightarrow 4)_a(E1\rightarrow 6)_{b\ Cl3Ac}D)_y$-All;

$(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ Ac}C((E1\rightarrow 4)_a(E1\rightarrow 6)_{b\ Cl3Ac}D)_y$;

$(E1\rightarrow 4)_a(E1\rightarrow 6)_{bCl3Ac}D)_x(E1\rightarrow 3)_c(E1\rightarrow 4)_cA(E1\rightarrow 3)_d(E1\rightarrow 4)_dB(E1\rightarrow 4)_{e\ ClAc}C((E1\rightarrow 4)_a(E1\rightarrow 6)_{b\ Cl3Ac}D)_y$;

$(E1\rightarrow 4)_a(E1\rightarrow 6)_{bCl3Ac}D)_x(E1\rightarrow 3)_c(E1\rightarrow 4)_cA(E1\rightarrow 4)_d(E1\rightarrow 4)_dB(E1\rightarrow 4)_eC((E1\rightarrow 4)_a(E1\rightarrow 6)_{b\ Cl3Ac}D)_y$;

$(E1\rightarrow 4)_a(E1\rightarrow 6)_{bCl3Ac}D)_x(E1\rightarrow 3)_cA(E1\rightarrow 3)_dB(E1\rightarrow 4)_{eClAc}C((E1\rightarrow 4)_a(E1\rightarrow 6)_{b\ Cl3Ac}D)_y$-All;

$(E1\rightarrow 4)_a(E1\rightarrow 6)_{bCl3Ac}D)_x(E1\rightarrow 3)_cA(E1\rightarrow 3)_dB(E1\rightarrow 4)_eC((E1\rightarrow 4)_a(E1\rightarrow 6)_{b\ Cl3Ac}D)_y$-All;

$(E1\rightarrow 4)_a(E1\rightarrow 6)_{bCl3Ac}D)_x(E1\rightarrow 3)_cA(E1\rightarrow 3)_dB(E1\rightarrow 4)_{e\ Ac}C((E1\rightarrow 4)_a(E1\rightarrow 6)_{b\ Cl3Ac}D)_y$-All;

$(E1\rightarrow 4)_a(E1\rightarrow 6)_{bCl3Ac}D)_x(E1\rightarrow 3)_cA(E1\rightarrow 3)_dB(E1\rightarrow 4)_{e\ Ac}C((E1\rightarrow 4)_a(E1\rightarrow 6)_{b\ Cl3Ac}D)_y$;

$(E1\rightarrow 4)_a(E1\rightarrow 6)_{bCl3Ac}D)_x(E1\rightarrow 3)_cA(E1\rightarrow 3)_dB(E1\rightarrow 4)_{eClAc}C((E1\rightarrow 4)_a(E1\rightarrow 6)_{b\ Cl3Ac}D)_y$;

$(E1\rightarrow 4)_a(E1\rightarrow 6)_{bCl3Ac}D)_x(E1\rightarrow 3)_cA(E1\rightarrow 3)_dB(E1\rightarrow 4)_eC((E1\rightarrow 4)_a(E1\rightarrow 6)_{b\ Cl3Ac}D)_y$;

$AB_{ClAC}C(E1\rightarrow 6)_{Cl3Ac}D$-All;

$ABC(E1\rightarrow 6)_{Cl3AcD}$-All;

$AB_{ClAc}C(E1\rightarrow 6)_{Cl3Ac}D$;

$AB_{Ac}C(E1\rightarrow 6)_{Cl3Ac}D$-All;

$AB_{Ac}C(E1\rightarrow 6)_{Cl3Ac}D$;

$ABC(E1\rightarrow 6)_{Cl3Ac}D$;

$(E1\rightarrow 3)AB_{ClAc}C_{Cl3Ac}D$-All;

$(E1\rightarrow 3)AB_{CCl3Ac}D$-All;

$(E1\rightarrow 3)AB_{Ac}C_{Cl3Ac}D$-All;

$(E1\rightarrow 3)AB_{Ac}C_{Cl3Ac}D$;

$(E1\rightarrow 3)AB_{ClAc}C_{Cl3Ac}D$;

$(E1\rightarrow 3)ABC_{Cl3Ac}D$;

$(E1\rightarrow 4)AB_{ClAc}C_{Cl3Ac}D$-All;

$(E1\rightarrow 4)ABC_{Cl3Ac}D$-All;

$(E1\rightarrow 4)AB_{Ac}C_{Cl3Ac}D$-All;

$(E1\rightarrow 4)AB_{Ac}C_{Cl3Ac}D$;

$(E1\rightarrow 4)AB_{ClAc}C_{Cl3Ac}D$;

$(E1\rightarrow 4)ABC_{Cl3Ac}D$;

$A(E1\rightarrow 4)B_{ClAc}C_{Cl3Ac}D$-All;

$A(E1\rightarrow4)BC_{Cl3Ac}D$-All;

$A(E1\rightarrow4)B_{Ac}C_{Cl3Ac}D$-All;

$A(E1\rightarrow4)B_{Ac}C_{Cl3Ac}D$;

$A(E1\rightarrow4)B_{ClAc}C_{Cl3Ac}D$;

$A(E1\rightarrow4)BC_{Cl3Ac}D$;

wherein:
Cl3Ac is $Cl_3C$—C(O)—;
ClAc is $ClCH_2$—C(O)—;
All is allyl;
x and y are 0 or 1, providing x+y=1;
A is 2)-α-L-Rhap-(1→;
B is 2)-α-L-Rhap-(1→;
C is 3)-α-L-Rhap-(1→;
D is 3)-α-D-GlcpN-(1→or 3)-β-D-GlcpN-(1→;
E represents a residue α-D-Glcp-;
a is 0 or 1;
a' is:
–0 or 1 when a is 1;
–0 when a is 0;
e is 0 or 1;
c' is 0 or 1;
d and d' are 0 or 1, providing d+d'=0 or 1;
c is at each occurrence independently 0 or 1, providing c+c'=0 or 1;
b is at each occurrence independently 0 or 1, providing a +b=0 or 1;
or of one of the following formulae:

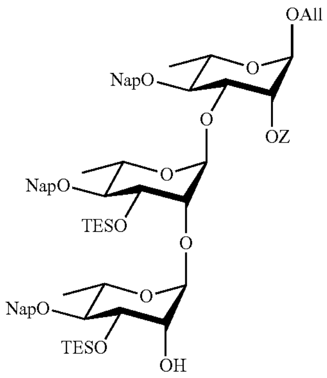

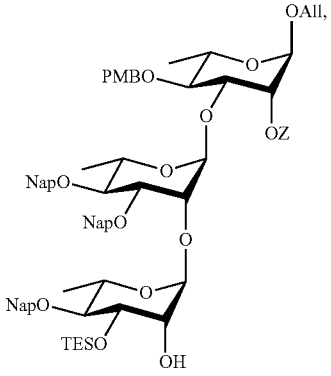

-continued

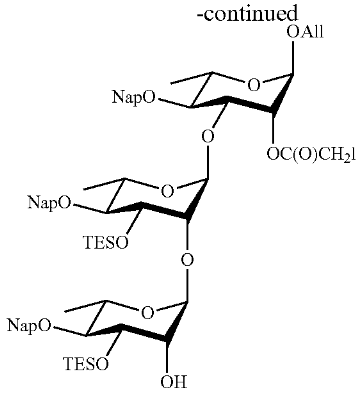

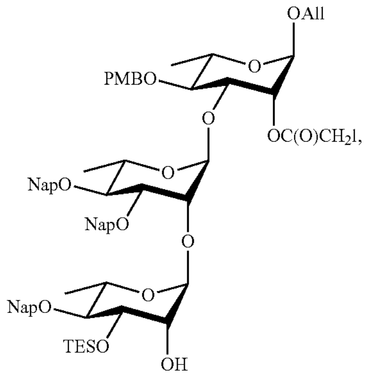

at least one of the TES groups or each TES group being optionally independently replaced by a group chosen from TBS, TIPS, PMB or Nap;

at least one of the Nap groups or each Nap group being optionally independently replaced by a group chosen from TBS, TIPS or PMB;

wherein:

All is allyl;

Z is ClAc or BrAc;

Nap is 2-naphtylmethyl;

TES is triethylsilyl;

TBS is tert-butyldimethylsilyl;

TIPS is triisopropylsilyl;

PMB is para-methoxybenzyl;

PTFA represents N-phenyltrifluoroacetimidyl;

TCA represents trichloroacetimidyl.

* * * * *